United States Patent [19]

Levitt et al.

[11] 4,310,346
[45] Jan. 12, 1982

[54] N(SUBSTITUTED PHENYLSULFONYL) N'(SUBSTITUTED CYUMIDIN-2-yl) UREAS

[75] Inventors: George Levitt, Wilmington; Richard F. Sauers, Hockessin, both of Del.

[73] Assignee: E. I. Du Pont de Nemours and Company, Wilmington, Del.

[21] Appl. No.: 152,022

[22] Filed: May 30, 1980

Related U.S. Application Data

[63] Continuation-in-part of Ser. No. 130,342, Mar. 14, 1980, abandoned, which is a continuation-in-part of Ser. No. 59,153, Jul. 20, 1979, abandoned.

[51] Int. Cl.$^3$ .................... A01N 9/22; C07D 239/42
[52] U.S. Cl. ............................................. 71/92; 71/93;
544/113; 544/114; 544/182; 544/206; 544/208;
544/211; 544/321; 544/323; 544/332; 544/161;
546/229; 546/230; 546/232; 260/239 B;
260/243.3; 260/326.5 SF; 260/326.5 J;
260/326.82; 260/397.6; 260/397.7 R; 260/453
R; 260/453 AR; 260/465 F; 260/465 G;
260/465 E; 260/456 A; 260/545 R; 560/13
[58] Field of Search ..................... 71/92; 260/243.3;
544/114, 321, 323, 332

[56] References Cited
U.S. PATENT DOCUMENTS 4,169,719 10/1979 Levitt .................................. 544/332
4,190,432 2/1980 Levitt .................................. 544/323
4,214,890 7/1980 Levitt .................................... 71/92

*Primary Examiner*—Donald G. Daus
*Assistant Examiner*—James H. Turnipseed

[57] ABSTRACT

This invention relates to N(Substituted Phenylsulfonyl) N'(Substituted Pyrimidinyl) urea compounds having the formulae I and IA

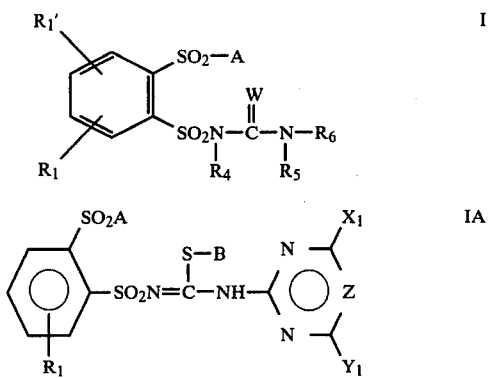

to agricultural compositions containing them and to their methods of use as general as well as selective pre- and post-emergence herbicides and as plant growth regulants.

34 Claims, No Drawings

N(SUBSTITUTED PHENYLSULFONYL) N'(SUBSTITUTED CYUMIDIN-2-yl) UREAS

RELATED APPLICATIONS

This application is a continuation-in-part of our co-pending application U.S. Ser. No. 130,342, now abandoned filed Mar. 14, 1980, which is a continuation-in-part of U.S. Ser. No. 059,153, filed July 20, 1979, now abandoned.

This invention relates to certain benzene-1,2-disulfonic acid derivatives that are useful as agricultural chemicals.

French Pat. No. 1,468,747 discloses the following para-substituted phenylsulfonamides, useful as anti-diabetic agents:

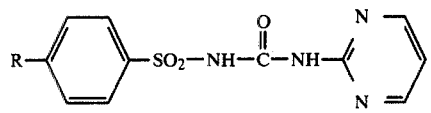

where R=H, halogen, $CF_3$ or alkyl.

Logemann et al., Chem. Ab., 53, 18052 g (1959), disclose a number of sulfonamides, including uracil derivatives and those having the formula:

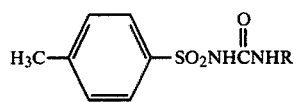

wherein R is butyl, phenyl or

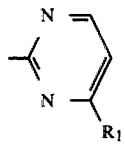

and $R_1$ is hydrogen or methyl. When tested for hypoglycemic effect in rats (oral doses of 25 mg/100 g), the compounds in which R is butyl or phenyl were most potent. The others were of low potency or inactive.

Wojciechowski, J. Acta. Polon. Pharm. 19, P. 121-5 (1962) [Chem. Ab., 59 1633 e] describes the synthesis of N-[(2,6-dimethoxypyrimidin-4-yl)aminocarbonyl]-4-methylbenzenesulfonamide:

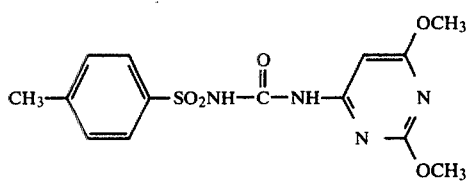

Based upon similarity to a known compound, the author predicted hypoglycemic activity for the foregoing compound.

Netherlands Pat. No. 121,788, published Sept. 15, 1966, teaches the preparation of compounds of Formula (i), and their use as general or selective herbicides:

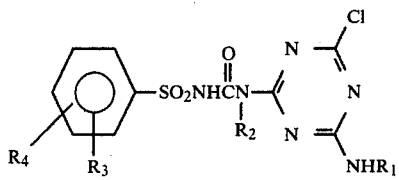

wherein $R_1$ and $R_2$ may independently be alkyl of 1-4 carbon atoms; and $R_3$ and $R_4$ may independently be hydrogen, chlorine or alkyl of 1-4 carbon atoms.

Compounds of Formula (ii), and their use as antidiabetic agents, are reported in J. Drug. Res. 6, 123 (1974):

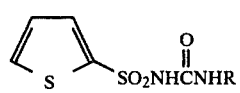

wherein R is pyridyl.

The presence of undesired vegetation causes substantial damage to useful crops, especially agricultural products that satisfy man's basic food needs, such as soybeans, wheat and the like. The current population explosion and concomitant world food shortage demand improvements in the efficiency of producing these crops. Prevention or minimizing the loss of a portion of such valuable crops by killing, or inhibiting the growth of undesired vegetation is one way of improving this efficiency.

A wide variety of materials useful for killing, or inhibiting (controlling) the growth of undesired vegetation is available; such materials are commonly referred to as herbicides. The need exists, however, for still more effective herbicides that destroy or retard weeds without causing significant damage to useful crops.

SUMMARY OF THE INVENTION

This invention relates to novel compounds of Formulae I and IA, to agricultural compositions containing them and to their methods of use as general as well as selective pre- and post-emergence herbicides and as plant growth regulants.

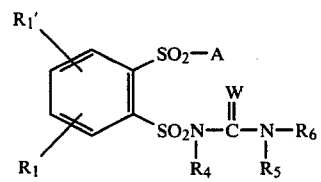

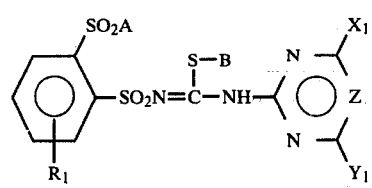

wherein
A is $NR_2R_3$, $OCH_2CCl_3$, $OCH_2CBr_3$ or

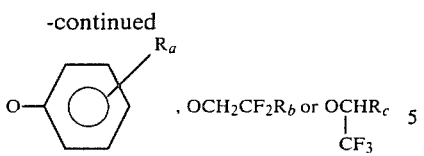, $OCH_2CF_2R_b$ or $OCHR_c$ 
$|$
$CF_3$ where $R_a$ is H, Cl, $CH_3$, $OCH_3$ or $NO_2$ and $R_b$ is H, F or $C_1$-$C_2$ alkyl with 0-5F and $R_c$ is $CH_3$ or $CF_3$; $R_1$ is H, Cl, Br, F, $C_1$-$C_3$ alkyl, $NO_2$, $OCH_3$,

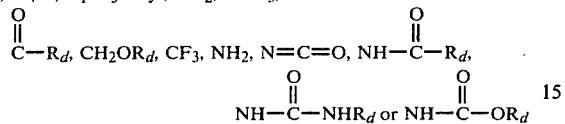

where $R_d$ is $C_1$-$C_3$ alkyl, or $R_1$ is $N(CH_3)_2$, CN, $CH_2S(O)_nCH_3$ or $S(O)_nCH_3$, where n is 0, 1 or 2;

$R_1'$ is H, Cl, F, Br, $CH_3$ or $OCH_3$;

$R_2$ is H, $C_1$-$C_6$ alkyl, $C_3$-$C_4$ alkenyl, $C_3$-$C_6$ cycloalkyl, $C_4$-$C_7$ cycloalkylalkyl, $C_5$-$C_6$ cycloalkenyl, $C_3$-$C_5$ alkynyl, $C_3$-$C_6$ cycloalkyl substituted with 1-2 $CH_3$ groups, $CF_2CF_2H$, $CF_2CHFCl$, $CF_2CHFBr$, $CF_2CHFCF_3$, $C(CH_3)_2CN$, $(CH_2)_mCN$, where m is 1 or 2, $CH_2CH_2OCH_3$, $CH_2CH(CH_3)OCH_3$, $(CH_2)_3OCH_3$, $CHR_7CO_2R_8$ or $CHR_7CON(R_8)_2$, where $R_7$ is H or $CH_3$ and $R_8$ is $C_1$-$C_3$ alkyl, $OCH_3$,

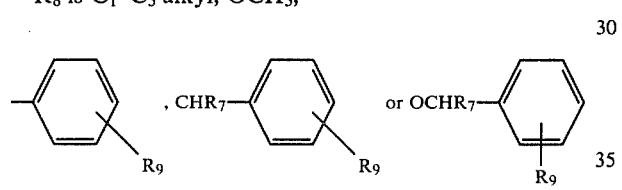

where $R_9$ is H, $CH_3$, Cl, Br or F;

$R_3$ is $C_1$-$C_4$ alkyl, $C_3$-$C_4$ alkenyl, $CH_2CH_2OCH_3$, $CH_2CH(CH)_3OCH_3$, $CH_2CF_3$, or $(CH_2)_mCN$, where m is 1 or 2, or $CHR_7CO_2R_8$, $NR_2R_3$ taken together are

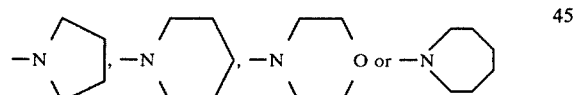

$R_4$ and $R_5$ are independently H or $CH_3$, but $R_4$ and $R_5$ cannot both be $CH_3$;

$R_6$ is

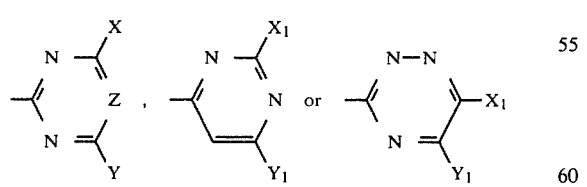

wherein

X is H, $CH_3$, $CH_3O$ or $CH_3CH_2O$;

Y is Cl, Br, H, $C_1$-$C_3$ alkyl, $CF_3$, $NHCH_3$, $N(CH_3)_2$, $OCH_2CF_3$, $OCH_3$, $OC_2H_5$, $SCH_3$, $O(CH_2)_pOR_{10}$, where p is 2 or 3 and $R_{10}$ is $CH_3$ or $C_2H_5$, $CH_2CH_2OCH_3$, $CH_2OCH_3$, $CH_2OCH_2CH_3$, $OCHR_7CO_2R_{11}$, $OCHR_7CON(R_8)_2$, $CO_2R_{11}$ and $CH_2CO_2R_{11}$, where $R_{11}$ is H or $C_1$-$C_3$ alkyl, $CH_2CN$, $NCH_3(CH_2CN)$, $CH_2CH_2CN$, $CH_2Cl$, $N_3$, $OCH_2CH=CH_2$ or $OCH_2C\equiv CH$;

$X_1$ is H, $OCH_3$ or $CH_3$;

$Y_1$ is H, $OCH_3$, $OCH_2CH_3$ or $CH_3$, provided that $X_1$ and $Y_1$ are not both H simultaneously;

Z is N or CH;

W is O or S; and

B is $C_1$-$C_6$ alkyl, $CH_2CH_2OCH_3$, $CH_2CH_2OCH_2CH_3$,
$CH_2CH_2CH_2OCH_3$, $CH_2Q$, $CH-Q$
$|$
$CH_3$ where Q is

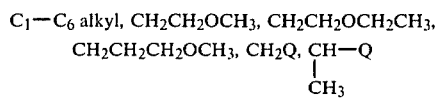

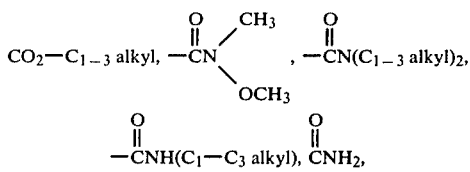

phenyl, phenyl substituted with chlorine, CN, $C_{2-4}$ alkenyl, $C_{2-4}$ alkynyl, $OR_{11}'$, where $R_{11}'$ is $C_1$-$C_4$ alkyl, $-CH_2OCH_2CH_2OCH_3$, or $-CH_2OCH_2C-H_2OCH_2CH_3$;

provided that:

(1) when $R_2$ is $OCH_3$, $R_3$ is $CH_3$;

(2) when $R_2$ is $CF_2CHFCl$, $CF_2CHFBr$, $CF_2CF_2H$ or $CF_2CHFCF_3$, then $R_3$ is $C_1$-$C_4$ alkyl;

and their agriculturally suitable salts.

Preferred in order of increasing preference for reasons of increased activity or ease of synthesis, or both, are (1) Compounds of Formula I.

(2) Compounds of preference (1), wherein $R_4+R_5+H$.

(3) Compounds of preference (2), wherein W=O.

(4) Compounds of preference (3), wherein $R_1'$=H.

(5) Compounds of preference (4), wherein $R_6$ is

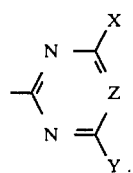

(6) Compounds of preference (5), wherein A is $OCH_2CF_3$ or $NR_2R_3$ and $R_2$ is $C_1$-$C_6$ alkyl, $C_3$-$C_4$ alkenyl, $OCH_3$, $CH_2CH_2OCH_3$, $CH_2CH(CH_3)OCH_3$ or $(CH_2)_3OCH_3$, or $NR_2R_3$ taken together are

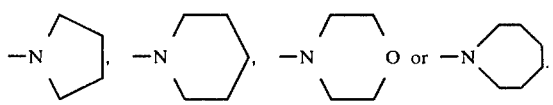

(7) Compounds of preference (5), wherein $R_3$ is $C_1$-$C_4$ alkyl or where $NR_2R_3$ taken together are

(8) Compounds of preference (6), wherein
R$_3$ is C$_1$-C$_4$ alkyl or where NR$_2$R$_3$ taken together are

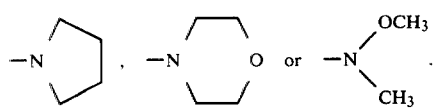

(9) Compounds of preference (8), wherein
R$_1$ is H, Cl, CF$_3$, NO$_2$, CH$_3$ or OCH$_3$.
(10) Compounds of preference (9), wherein
R$_2$ is C$_1$-C$_4$ alkyl or NR$_2$R$_3$ taken together are

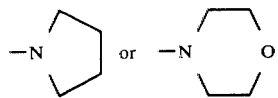

(11) Compounds of preference (10) in which
X is CH$_3$, OCH$_3$ or OCH$_2$CH$_3$; and
Y is H, CH$_3$, CH$_3$CH$_2$, OCH$_2$CF$_3$, OCH$_3$, OC$_2$H$_5$, OCH$_2$CH$_2$OCH$_3$, CH$_2$OCH$_3$, CH$_2$CH$_2$OCH$_3$, N(CH$_3$)CH$_2$CN, OCH$_2$CH=CH$_2$, or OCH$_2$C≡CH.
(12) Compounds of preference (11) in which
X is CH$_3$, OCH$_3$ or OCH$_2$CH$_3$; and
Y is CH$_3$, OCH$_2$CF$_3$, OCH$_3$ or OCH$_2$CH$_3$.

Specifically preferred for their high biological activity or favorable ease of synthesis, or both, are N'-[(4,6-Dimethoxypyrimidin-2-yl)aminocarbonyl]-N,N-dimethyl-1,2-benzenedisulfonamide.
N'-[(4,6-Dimethoxy-1,3,5-triazin-2-yl)aminocarbonyl]-N,N-dimethyl-1,2-benzenedisulfonamide.
N'-[(4-Methoxy-6-methylpyrimidin-2-yl)aminocarbonyl]-N,N-dimethyl-1,2-benzenedisulfonamide.
N'-[(4-Methoxy-6-methyl-1,3,5-triazin-2-yl)aminocarbonyl]-N,N-dimethyl-1,2-benzenedisulfonamide.
N'-[(4,6-Dimethyl-1,3,5-triazin-2-yl)aminocarbonyl]-N,N-dimethyl-1,2-benzenedisulfonamide.
N'-[(4,6-Dimethylpyrimidin-2-yl)aminocarbonyl]-N,N-dimethyl-1,2-benzenedisulfonamide.
N'-[(4-Methoxy-6-methylpyrimidin-2-yl)aminocarbonyl]-N,N-diethyl-1,2-benzenedisulfonamide.
N'-[(4,6-Dimethoxy-1,3,5-triazin-2-yl)aminocarbonyl]-N,N-diethyl-1,2-benzenedisulfonamide.
N'-[(4,6-Dimethoxypyrimidin-2-yl)aminocarbonyl]-N,N-diethyl-1,2-benzenedisulfonamide.
N'-(4,6-Dimethylpyrimidin-2-yl)aminocarbonyl]-N,N-diethyl-1,2-benzenedisulfonamide.
N'-[(4-Methoxy-6-methyl-1,3,5-triazin-2-yl)aminocarbonyl]-N,N-diethyl-1,2-benzenedisulfonamide.
N'-[(4,6-Dimethyl-1,3,5-triazin-2-yl)aminocarbonyl]-N,N-diethyl-1,2-benzenedisulfonamide.
N$^2$-[(4,6-Dimethoxypyrimidin-2-yl)aminocarbonyl]-N$^1$,N$^1$-dimethyl-4-(trifluoromethyl)-1,2-benzenesulfonamide.
4-Chloro-N$^2$-[(4-methoxy-6-methylpyrimidin-2-yl)aminocarbonyl]-N$^1$, N$^1$-dimethyl-1,2-benzenedisulfonamide.
(2,2,2-Trifluoroethyl) 2-[[(4,6-dimethoxypyrimidin-2-yl)aminocarbonyl]aminosulfonyl]benzenesulfonoate.
(2,2,2-Trifluoroethyl) 2-[[(4,6-dimethoxy-1,3,5-triazin-2-yl)aminocarbonyl]aminosulfonyl]benzenesulfonoate.
(2,2,2-Trifluoroethyl) 2-[[(4-methoxy-6-methylpyrimidin-2-yl)aminocarbonyl]aminosulfonyl]benzenesulfonoate.
(2,2,2-Trifluoroethyl) 2-[[(4-methoxy-6-methyl-1,3,5-triazin-2-yl)aminocarbonyl]aminosulfonyl]benzenesulfonoate.
N'[(4,6-Dimethylpyrimidin-2-yl)aminocarbonyl]-N-ethyl-N-methyl-1,2-benzenedisulfonamide.
N-Ethyl-N'[(4-methoxy-6-methylpyrimidin-2-yl)aminocarbonyl]-N-methyl-1,2-benzenedisulfonamide.
N'-[(4,6-Dimethoxypyrimidin-2-yl)aminocarbonyl]-N-ethyl-N-methyl-1,2-benzenedisulfonamide.
4-Chloro-N'-[(4-methoxy-6-methyl-1,3,5-triazin-2-yl)-aminocarbonyl]-N,N-dimethyl-1,2-benzenedisulfonamide.
N,N-Dimethyl-N'(([4-methyl-6-(2,2,2-trifluoroethoxy)-1,3,5-triazin-2-yl]aminocarbonyl))-1,2-benzenedisulfonamide.
N-Methyl-N(1-methylethyl)-N'-[(4,6-dimethoxypyrimidin-2-yl)aminocarbonyl]-1,2-benzenedisulfonamide.
N-Methyl-N(1-methylethyl)-N'-[(4-methyl-6-methoxypyrimidin-2-yl)aminocarbonyl]-1,2-benzenedisulfonamide.
N-Methyl-N(1-methylethyl)-N'-[4-methyl-6-methoxy-1,3,5-triazin-2-yl)aminocarbonyl]-1,2-benzenedisulfonamide.

This invention also relates to novel sulfonylisocyanate intermediates of Formula I-B

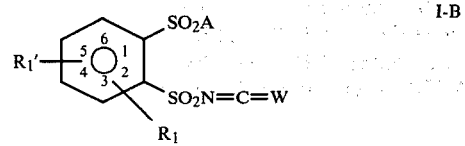

wherein
A is

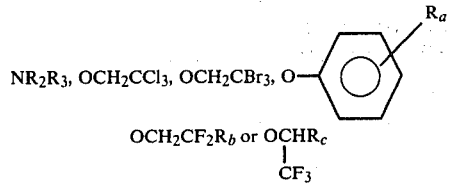

where R$_a$ is H, Cl, CH$_3$, OCH$_3$ or NO$_2$ and R$_b$ is H, F or C$_1$-C$_2$ alkyl with 0-5F and R$_c$ is CH$_3$ or CF$_3$;
R$_1$ is H, Cl, Br, F, C$_1$—C$_3$ alkyl, NO$_2$, OCH$_3$, $\overset{O}{\overset{\|}{C}}R_d$, CH$_2$OR$_d$, CF$_3$, N=C=O, N(CH$_3$)$_2$, CN, S(O)$_n$CH$_3$ or CH$_2$S(O)$_n$CH$_3$ where n is 0 or 2;
R$_1$' is H, Cl, F, Br, CH$_3$ or OCH$_3$; W is O or S;
R$_2$ is C$_1$-C$_6$ alkyl, C$_3$-C$_4$ alkenyl, C$_3$C$_6$ cycloalkyl, C$_5$-C$_6$ cycloalkenyl, C$_4$-C$_7$ cycloalkylalkyl, C$_3$-C$_6$ cycloalkyl substituted with 1-2 CH$_3$ groups, C$_3$-C$_5$ alkynyl, CF$_2$CF$_2$H, CF$_2$CHFCl, CF$_2$CHFBr, CF$_2$CHCF$_3$, $C(CH_3)_2CN$, $(CH_2)_mCN$, where m is 1 or 2, $CH_2CH_2OCH_3$, $CH_2CH(CH_3)OCH_3$, $(CH_2)OCH_3$, $CHR_7CO_2R_8$ or $CHR_7CON(R_8)_2$, where $R_7$ is H or $CH_3$ and $R_8$ is $C_1-C_3$ alkyl, $OCH_3$,

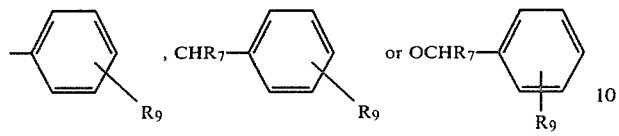

where
$R_9$ is H, $CH_3$, Cl, Br or F;
$R_3$ is $C_1-C_4$ alkyl, $C_3-C_4$ alkenyl, $CH_2CH_2OCH_3$, $CH_2CH(CH)_3OCH_3$, $CH_2CF_3$ or $(CH_2)_mCN$, where m is 1 or 2 or $CHR_7CO_2R_8$ or $NR_2R_3$ taken together are

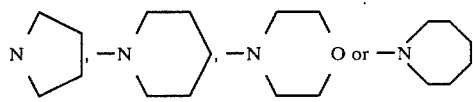

provided that:
(1) when $R_2$ is $OCH_3$, $R_3$ is $CH_3$;
(2) when $R_2$ is $CF_2CHFCl$, $CF_2CHFBr$, $CF_2CF_2H$ or $CF_2CHFCF_3$, then $R_3$ is $C_1-C_4$ alkyl;
(3) when $R_1$ is CN or N=C=O, it cannot be in the 3-position.

Preferred intermediates for reasons of higher activity and/or lower cost of derived herbicides of Formula I are:
(1) Compounds of Formula I-B in which W=O.
(2) Compounds of preference (1) in which $R_1'$=H.
(3) Compounds of preference (2) wherein A is $OCH_2CF_3$ or $NR_2R_3$ and $R_2$ is $C_1-C_6$ alkyl, $C_3-C_4$ alkenyl, $OCH_3$, $CH_2CH_2OCH_3$, $CH_2CH(CH_3)OCH_3$ or $(CH_2)_3OCH_3$, or $NR_2R_3$ taken together are

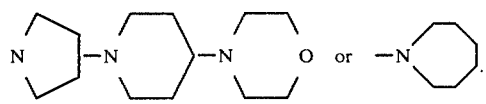

(4) Compounds of preference (3), wherein $R_3$ is $C_1-C_4$ alkyl or where $NR_2R_3$ taken together are

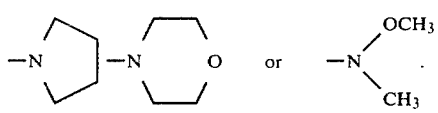

(5) Compounds of preference (4), wherein $R_1$ is H, Cl, $CF_3$, $NO_2$, $CH_3$ or $OCH_3$.
(6) Compounds of preference (5), wherein $R_2$ is $C_1-C_4$ alkyl or $NR_2R_3$ taken together are

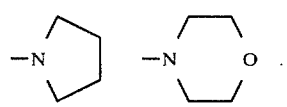

Specifically preferred intermediates for reasons of highest activity and/or lowest cost of desired herbicides of Formula I are:

N,N-Dimethyl-2-(isocyanatosulfonyl)benzenesulfonamide.
N-Ethyl-2-(isocyanatosulfonyl)-N-methylbenzenesulfonamide.
2-(Isocyanatosulfonyl)-N-methyl-N-(methylethyl)benzenesulfonamide.
N,N-Dimethyl-2-(isocyanatosulfonyl)-4-trifluoromethylbenzenesulfonamide.
2-[(2,2,2-Trifluoroethyl)sulfonyl]benzenesulfonyl isocyanate.

SYNTHESIS

Many of the compounds of Formula I may be prepared as shown in Equation 4 by the reaction of an appropriately substituted benzenesulfonyl isocyanate or isothiocyanate with an appropriate aminopyrimidine or aminotriazine. The benzenesulfonyl isocyanate and isothiocyanates are therefore important intermediates for the preparation of the compounds of this invention. The synthesis of these compounds is described in Equations 1-4.

Equation 1

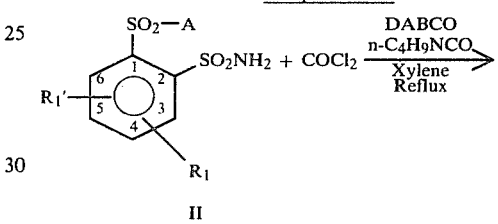

wherein
A is $NR_2R_3$, $OCH_2CCl_3$, $OCH_2CBr_3$,

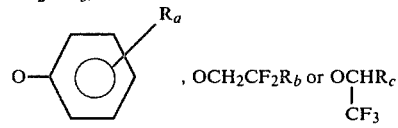, $OCH_2CF_2R_b$ or $OCHR_c$
                                                         |
                                                        $CF_3$ where $R_a$ is H, Cl, $CH_3$, $OCH_3$ or $NO_2$ and $R_b$ is H, F or $C_1-C_2$ alkyl with 0-5F and $R_c$ is $CH_3$ or $CF_3$.
$R_1$ is

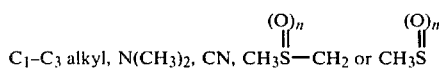

where $R_d$ is $C_1-C_3$ alkyl, $N(CH_3)_2$, CN, $CH_3S-CH_2$ or $CH_3S$ with $(O)_n$ above S where n is 0 or 2;
$R_1'$ is H, Cl, F, Br, $CH_3$ or $OCH_3$;
$R_2$ is $C_1-C_6$ alkyl, $C_3-C_4$ alkenyl, $C_3-C_6$ cycloalkyl, $C_5-C_6$ cycloalkenyl, $C_4-C_7$ cycloalkylalkyl, $C_3-C_6$ cycloalkyl substituted with 1-2 $CH_3$ groups, $C_3-C_5$ alkynyl, C(CH$_3$)$_2$CN, (CH$_2$)$_m$CN, where m is 1 or 2, CF$_2$CF$_2$H, CF$_2$CHFCl, CF$_2$CHFBr, CF$_2$CHFCF$_3$, CH$_2$CF$_3$, CH$_2$CH$_2$OCH$_3$, CH$_2$CH(CH$_3$)OCH$_3$, (CH$_2$)$_3$OCH$_3$, or OCH$_3$, provided that when R$_2$ is OCH$_3$, R$_3$ is CH$_3$, CH(R$_7$)CO$_2$R$_8$ or CH(R$_7$)CON(R$_8$)$_2$, where R$_7$ is H or CH$_3$, and R$_8$ is C$_1$-C$_3$ alkyl; or R$_2$ is

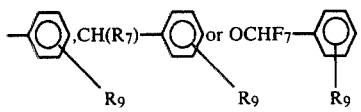

where
R$_9$ is H, CH$_3$, Cl, Br or F;
R$_3$ is C$_1$-C$_4$ alkyl, C$_3$-C$_4$ alkenyl, CH$_2$CH$_2$OCH$_3$, CH$_2$CH(CH$_3$)OCH$_3$, (CH$_2$)$_m$CN, where m is 1 or 2, CH(R$_7$)CO$_2$R$_8$, —CH$_2$CF$_3$, or NR$_2$R$_3$ taken together are

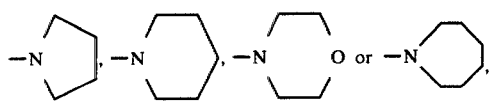

provided that when R$_2$ is CF$_2$CHFCl, CF$_2$CHFBr, CF$_2$CF$_2$H, or CF$_2$CHFCF$_3$, then R$_3$ is C$_{1-4}$ alkyl; Also provided that when R$_1$ is CN or N=C=O, it cannot be in the 3-position.

The above reaction is carried out by heating a mixture of the appropriate sulfonamide (II), an alkyl isocyanate such as butyl isocyanate and a catalytic amount of a tertiary amine such as 1,4-diaza[2,2,2]bicyclooctane (DABCO) in xylene, or other inert solvent of boiling point ≧135° to approximately 135°. Phosgene is then added to the mixture over a 1–6 hour period until an excess of phosgene is present as indicated by a drop in the boiling point to less than 130°. The mixture is cooled and filtered to remove a small amount of insoluble by-products. The solvent and the alkyl isocyanate are distilled off in-vacuo leaving a residue of the crude, sulfonyl isocyanate; IIa, which can be used without further purification.

The preparation of the sulfonamides, II, is described in Equation 8.

The sulfonyl isocyanates, IIa, can also be prepared, as shown in Equation 2, by first preparing the n-butylsulfonylureas III; and, reacting the compounds III with phosgene.

Equation 2

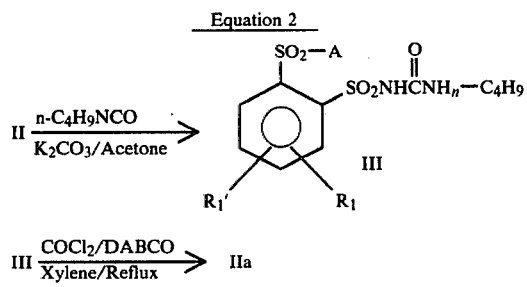

wherein A, R$_1$, R$_1'$, R$_2$ and R$_3$ are as defined in Equation 1.

The compounds III are conveniently prepared by stirring a mixture of the sulfonamides, II, anhydrous potassium carbonate, and n-butyl isocyanate in acetone or methyl ethyl ketone at 25°–80° until all of the isocyanate has reacted. The products are isolated by quenching in dilute mineral acid or by distilling off the solvent and recrystallizing the residue. The compounds III are treated with phosgene and a catalytic amount of DABCO in refluxing xylene or chlorobenzene in a manner analogous to that described in Equation 1.

Where W=S in Formula 1, the useful isothiocyanate intermediates, IV, are prepared according to Equation 3.

Equation 3

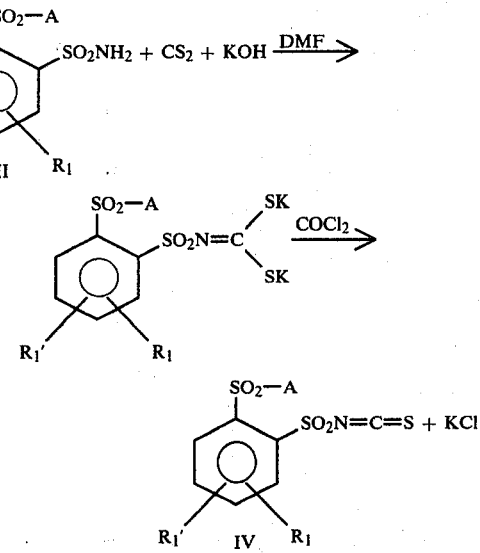

wherein A, R$_1$, R$_1'$, R$_2$ and R$_3$ are as defined in Equation 1.

The substituted sulfonamide is dissolved in dimethylformamide (DMF) with an equivalent amount of carbon disulfide, and two equivalents of potassium hydroxide are added in portions at room temperature. The mixture is stirred for 1–8 hours then diluted with ethyl acetate, ethyl ether, or other similar aprotic solvent to precipitate the dipotassium salt of the dithiocarbamic acid. The salt is isolated and suspended in an inert solvent such as xylene, chloroform, or carbon tetrachloride. Phosgene is added below room temperature and the mixture stirred at room temperature for 1–3 hours. The sulfonylisothiocyanate is isolated by filtering off the precipitated potassium chloride and concentrating the filtrate. These compounds tend to dimerize on standing and therefore should be used soon after preparation.

Compounds of Formula I can be prepared by the reaction described in Equation 4.

Equation 4

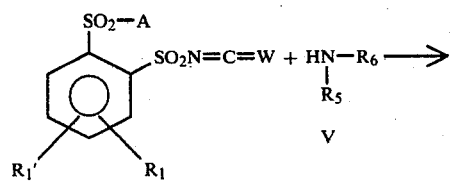

-continued
Equation 4

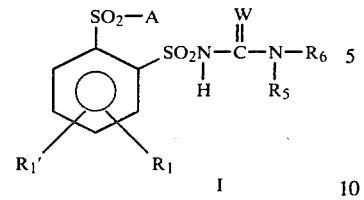

wherein
A, $R_1$, $R_1'$, $R_2$ and $R_3$ are as defined in Equation 1;
W is oxygen or sulfur;
$R_5$ is H or methyl;
$R_6$ is

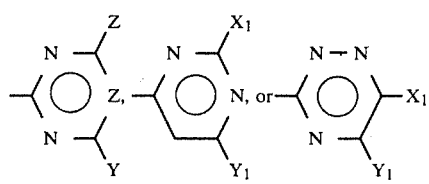

and
X is H, $CH_3$, $CH_3O$ or $CH_3CH_2O$;
Y is

Cl, Br, H, $C_1$-$C_3$ alkyl, $CF_3$, $NHCH_3$, $N(CH_3)_2$, $OCH_2CF_3$, $OCH_3$, $OCH_2CH_3$, $SCH_3$, $CH_2CN$, $NCH_2CN$, $CH_2CH_2CN$,
$\underset{CH_3}{|}$
$CH_2Cl$, $N_3$, $OCH_2CH=CH_2$, $OCH_2C\equiv CH$ or $O(CH_2)_pOR_{10}$, where
P is 2 or 3 and $R_{10}$ is $CH_3$ or $CH_3CH_2$, or
Y is $CH_2CH_2OCH_3$, $CH_2OCH_3$, $OCH(R_7)CO_2R_{11}$ or $OCH(R_7)CON(R_8)_2$, $CO_2R_{11}$ and $CH_2CO_2R_{11}$,
$R_7$ and $R_8$ are as previously defined; and
$R_{11}$ is H or $C_1$-$C_3$ alkyl;
$X_1$ is H, $OCH_3$ or $CH_3$;
$Y_1$ is H, $OCH_3$, $OCH_2CH_3$ or $CH_3$, provided that $X_1$ and $Y_1$ are not both H simultaneously; and
Z is N or CH.

The reaction of Equation 4 is best carried out in inert aprotic solvent such as methylene chloride, tetrahydrofuran, acetonitrile at a temperature between 20° and 80°. A catalytic amount of DABCO may be used to accelerate the reaction. In the cases in which the products are insoluble in the reaction solvent, they may be isolated by simple filtration. When the products are soluble in the reaction solvent they are isolated by evaporation of the solvent and trituration of the residue with solvents such as 1-chlorobutane ethylether, or methanol and filtration.

Compounds of Formula 1 in which W=S and $R_5$=H can also be prepared by the reaction shown in Equation 5.

Equation 5

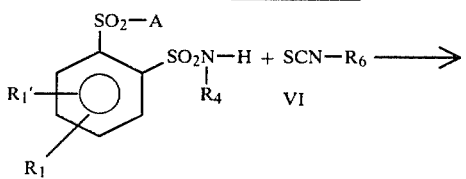

-continued
Equation 5

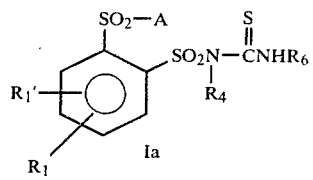

wherein A, $R_1$, $R_1'$, $R_2$, $R_3$ and $R_6$ are as defined in Equations 1-4, and $R_4$ is H or $CH_3$.

The reaction of Equation 5 is best carried out by suspending the sulfonamide, the isothiocyanate and an equivalent of a base such as anhydrous potassium carbonate in a solvent such as acetone, methyl ethyl ketone, acetonitrile or ethyl acetate. The reaction is stirred at 25°-80° for 1 to 24 hours. In some cases, the product precipitates from the reaction mixture and can be filtered off, suspended in dilute mineral acid, filtered again and washed with cold water. If the product does not precipitate, it can be isolated by evaporation of the solvent, trituration of the residue with dilute mineral acid and filtering off the insoluble product.

The heterocyclic isothiocyanates, VI, which are used in the procedure of Equation 5 are prepared according to the method of Japan Patent Application Pub. Kokai No. 51-143686, June 5, 1976; or that of W. Abraham and G. Barnikow, Tetrahedron 29, 691-7 (1973) both of which are herein incorporated by reference.

Compounds of Formula 1 in which W=S and $R_4$=H can also be prepared by the procedure shown in Equation 6.

Equation 6

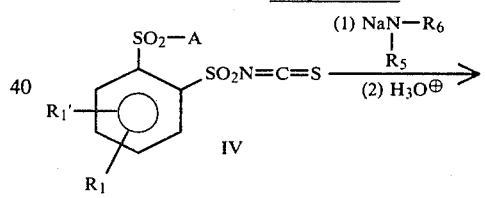

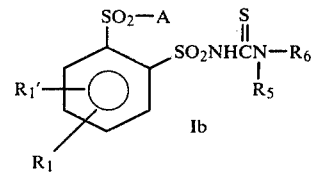

wherein A, $R_1'$, $R_1$-$R_6$ are as defined in Equations 1-5.

In the procedure of Equation 6, the aminotriazine or aminopyrimidine is added to a suspension of sodium hydride in dimethylformamide (DMF) or tetrahydrofuran (THF) and allowed to stir at room temperature for 1-4 hours. The resulting salt solution or suspension is then added to a solution of the sulfonyl isothiocyanate in DMF or THF and allowed to stir at room temperature for 1-4 hours. The product is isolated by quenching the reaction mixture in excess dilute mineral acid and filtering off the insoluble product; or by first evaporating the solvent off and triturating the residue in dilute mineral acid and collecting the solid product.

Alternatively, compounds of Formula I in which $R_4$ is a methyl group may be prepared by the procedure shown in Equation 7.

Equation 7

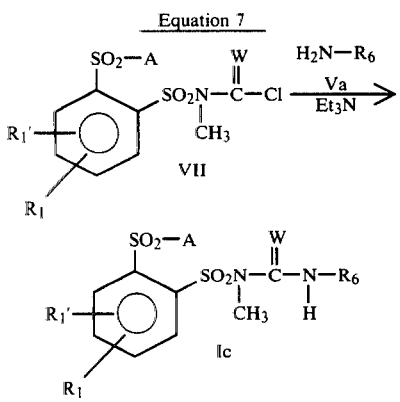

wherein A, $R_1'$, $R_1$–$R_6$ and W are as defined in Equations 1–6.

The reaction of Equation 7 can best be carried out by adding an equivalent of an acid acceptor, such as triethylamine, pyridine, or potassium carbonate, to a mixture of the chloride VII, and the aminoheterocyclic, Va, in an inert organic solvent such as tetrahydrofuran, methylene chloride or acetonitrile. Temperatures of 20°–80° may be employed. Soluble products can be isolated by filtering off the precipitated salts and concentration of the filtrate. Insoluble products can be filtered off and washed free of salts with water.

The chlorides of Formula VII can be prepared by phosgenation or thiophosgenation of the N-methylsulfonamide salts. The sulfonamide salt is added to an excess of phosgene or thiophosgene in an inert organic solvent, such as tetrahydrofuran or methylene chloride. After removal of the excess phosgene, the chloride VII can be isolated or reacted in-situ with the aminoheterocycle Va.

2-Aminopyrimidines are described by D. J. Brown in "The Pyrimidines", Vol. XVI of "The Chemistry of Heterocyclic Compounds", Interscience, New York, and London. The 2-amino-1,3,5-triazines are reviewed by K. R. Huffman, in "The Triazines" of this same series. The synthesis of triazines is also described in U.S. Pat. No. 3,154,547, and by H. R. Huffman and F. C. Schaeffer, J. Org. Chem. 28, 1816–1821 (1963). All of the above are herein incorporated by reference.

The benzenesulfonamides of Formula II; which are the starting materials in Equations 1, 2 and 3, can be prepared by the four step procedure described in Equation 8.

Equation 8

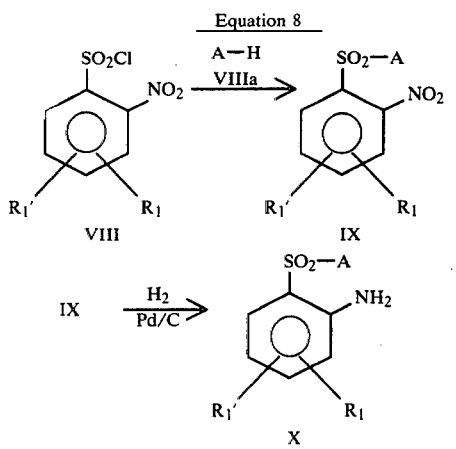

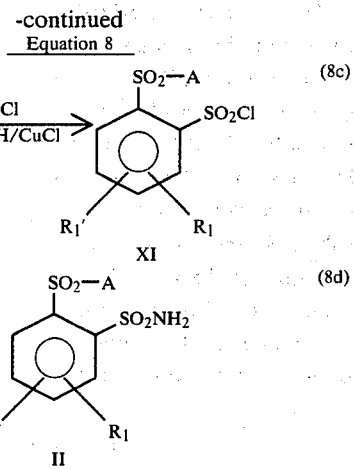

wherein A, $R_1'$, $R_1$, $R_2$, and $R_3$ are as defined in Equations 1–7, with the exception that $R_1$ cannot be $NO_2$.

In step 8a, the o-nitrobenzenesulfonyl chloride in Formula VIII, which are well-known in the art, are treated with an amine or an alcohol of Formula VIIIa in an inert organic solvent such as methylene chloride, ethyl ether, or tetrahydrofuran at 0°–50°. When VIIIa is an amine, it may be taken in excess to act as an acid acceptor; or, alternatively, a tertiary amine such as triethylamine or pyrimidine may be used as an acid acceptor. When VIIIa is an alcohol, a tertiary amine such as triethylamine or pyridine must be used as an acid acceptor. The by-product amine hydrochloride is filtered off or washed out of the solvent with water and the product isolated by evaporation of the solvent.

The reduction described in step 8b is accomplished by treating a solution of the compounds of Formula IX, in a solvent such as ethanol, ethyl acetate, or DMF, in a pressure vessel, with 100–1000 pounds per square inch of hydrogen at 80°–150° in the presence of a hydrogenation catalyst such as 5–10% palladium absorbed on carbon. When the theoretical amount of hydrogen has been absorbed, the solution is cooled and the catalyst is removed by filtration. The product is then isolated by evaporation of the solvent.

In the case where $R_1 = NO_2$, the reduction of step 8b can be accomplished using ammonium sulfide or sodium hydrosulfide instead of catalytic hydrogenation. This type of procedure is described in *Organic Synthesis* Coll. Vol. III, pgs. 242–3, John Wiley and Sons, Inc., New York and London (1955), the disclosure of which is herein incorporated by reference.

The diazotization and coupling with sulfur dioxide, described in step 8c, is accomplished in the following manner. A solution of the aniline of Formula X in a mixture of concentrated hydrochloric acid and glacial acetic acid is treated with a solution of sodium nitrite in water at −5° to 0°. After stirring for 10–15 minutes at 0° to insure complete diazotization, this solution is added to a mixture of an excess of sulfur dioxide, and a catalytic amount of cuprous chloride in glacial acetic acid at 0°–5°. The temperature is kept at 0°–5° for ¼ to 1 hour then raised to 20°–25° and held at that temperature for 2–4 hours. This solution is then poured into a large excess of ice water. The sulfonyl chloride products, XI, can be isolated by filtration or by extraction into a solvent such as ethyl ether or methylene chloride followed by evaporation of the solvent.

The amination described in step 8d is conveniently carried out by treating a solution of the sulfonyl chloride of Formula XI with an excess of anhydrous ammonia in a solvent such as ethyl ether or methylene chloride at 0°–25°. If the product sulfonamide, II, is insoluble it may be isolated by filtration followed by washing out the salts with water. If the product sulfonamide is soluble in the reaction solution, it may be isolated by filtering off the precipitated ammonium chloride and evaporation of the solvent.

Compounds of Formula 1 in which $R_1 = NH_2$ can be prepared by the reaction shown in Equation 9.

Equation 9

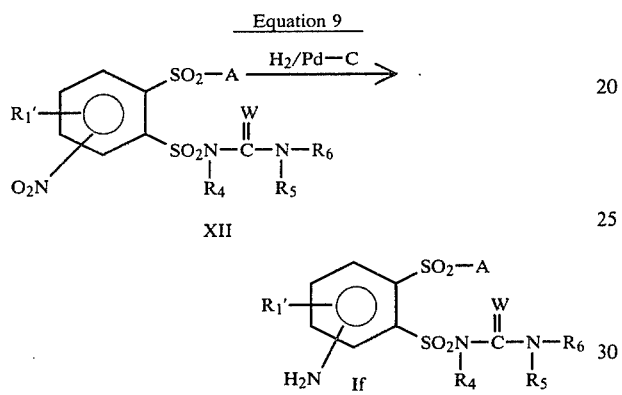

wherein A, $R_1'$, $R_2$–$R_6$ and W are as defined in Equations 1–8.

The reduction described in Equation 9 is accomplished by treating a solution of the compounds of Formula XII in a solvent such as ethyl acetate or DMF in a pressure vessel, with 100–1000 pounds per square inch of hydrogen at 80°–150° in the presence of a suitable hydrogenation catalyst such as 5–10% palladium absorbed on carbon. When the theoretical amount of hydrogen has been absorbed, the solution is cooled and the catalyst is removed by filtration. The product is then isolated by evaporation of the solvent.

Compounds of Formula I can also be prepared by the method described in Equation 10.

Equation 10

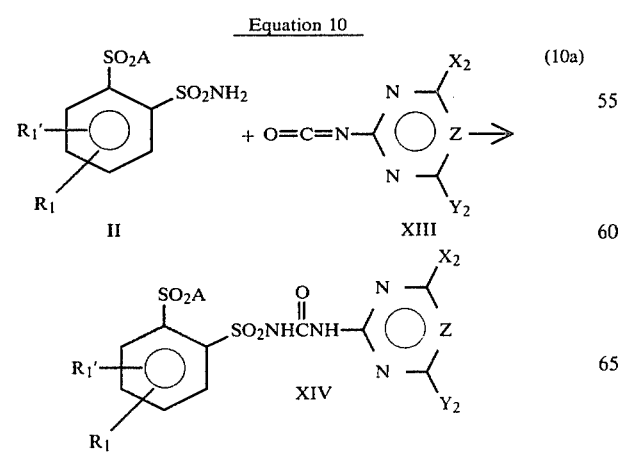

-continued
Equation 10

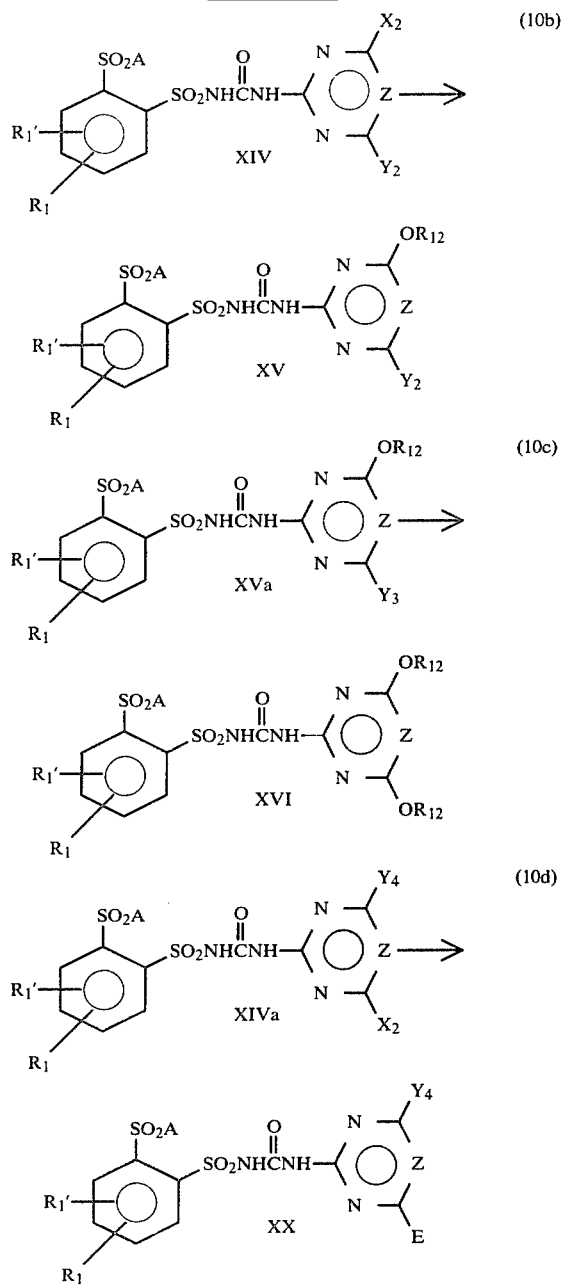

wherein
A, $R_1$, and $R_1'$ are as described in Equation 1;
$R_{12}$ is methyl, ethyl, $-\overset{\underset{|}{CH_3}}{C}HCO_2CH_3$ or $-CH_2CO_2CH_3$;

$R_{13}$ is methyl or ethyl;
$X_2$ is Cl or Br;
$Y_2$ is H, Cl, Br, methyl, ethyl or $CF_3$;
$Y_3$ is Cl or Br;
$Y_4$ is methyl, ethyl or $CF_3$; and
E is $(CH_3)_2N-$ or $CH_3S-$.

Reaction Step (10a)

In Reaction Step (10a), an aromatic sulfonamide of Formula II is contacted with a heterocyclic isocyanate of Formula XIII to yield an N-(haloheterocyclicaminocarbonyl)aromatic sulfonamide of Formula XIV.

The heterocyclic isocyanates used in Reaction (10a) may be prepared according to methods described in Swiss Pat. No. 579,062, U.S. Pat. No. 3,919,228, U.S. Pat. No. 3,732,223 and *Angew Chem. Int. Ed.* 10, 402 (1976), the disclosures of which are herein incorporated by reference.

The aromatic sulfonamide and the heterocyclic isocyanate are contacted in the presence of an inert organic solvent, for example, acetonitrile, tetrahydrofuran (THF), toluene, acetone or butanone. Optionally, a catalytic amount of a base, such as 1,4-diazabicyclo[2.2.2]octane (DABCO), potassium carbonate, sodium hydride or potassium tert-butoxide, may be added to the reaction mixture. The quantity of base constituting a catalytic amount would be obvious to one skilled in the art. The reaction mixture is preferably maintained at a temperature of about 25° to 110° C., and the product can generally be recovered by cooling and filtering the reaction mixture. For reasons of efficiency and economy, the preferred solvents are acetonitrile and THF, and the preferred temperature range is about 60° to 85° C.

Reaction Steps (10b) and (10c)

In Reaction Steps (10b) and (10c), one or two of the halogen atoms on the heterocyclic ring of the compound of Formula XIV is displaced by a nucleophilic species. Generally, this may be done by contacting the compound of Formula XIV either with alkanol, $R_{12}OH$, or with alkoxide, $-OR_{12}$, where $R_{12}$ is as defined above.

Thus, in Reaction Step (10b), a compound of Formula XIV, substituted with one displaceable group, can be contacted with at least one equivalent of alkanol, $R_{12}OH$. This reaction is sluggish, however, and it is preferred to contact the compound of Formula XIV with at least two equivalents of alkoxide, $-OR_{12}$. The alkoxide can be provided in a number of ways:

(a) The compound of Formula XIV can be suspended or dissolved in an alkanol solvent, $R_{12}OH$, in the presence of at least two equivalents of alkoxide, $-OR_{12}$. The alkoxide can be added directly as alkali metal or alkaline earth metal alkoxide or can be generated by the addition to the alkanol solvent of at least two equivalents of a base capable of generating alkoxide from the solvent. Suitable bases include, but are not limited to, the alkali and alkaline earth metals, their hydrides and tert-butoxides. For example, when $R_{12}$ is methyl, the compound of Formula XIV could be suspended or dissolved in methanol in the presence of two equivalents of sodium methoxide. Alternatively, two equivalents of sodium hydride could be used in place of the sodium methoxide.

(b) The compound of Formula XIV can be suspended or dissolved in an inert solvent in the presence of at least two equivalents of alkoxide, $-OR_{12}$. Suitable inert solvents include, but are not limited to, acetonitrile, THF and dimethylformamide. The alkoxide may be added directly as alkali metal or alkaline earth metal alkoxide or may be generated from alkanol and a base as described in (a) above. For example, when $R_{12}$ is methyl, the compound of Formula XIV could be suspended or dissolved in THF in the presence of two equivalents of sodium methoxide. Alternatively, two equivalents each of methanol and sodium hydride could be used instead of sodium methoxide.

For reasons of economy and efficiency, procedure (a) is the more preferred method.

It should be noted that two equivalents of alkoxide are required for Reaction Step (10b) whereas only one equivalent of alkanol is needed for the same process. This difference is due to the reaction which is believed to occur between the alkoxide and the sulfonyl nitrogen of the sulfonamide of Formula XIV. When alkoxide is used, the first equivalent of alkoxide removes a proton from the sulfonyl nitrogen, and it is only the second equivalent which effects displacement of the halogen. As a result, two equivalents of alkoxide are required. The resulting salt must be acidified, e.g., with sulfuric, hydrochloric or acetic acid, to yield a compound of Formula XV. Applicant, of course, does not intend to be bound by the mechanism described above.

In Reaction Step (10c) a compound of Formula XVa, substituted with at least one displacement group, is contacted with either one equivalent of alkanol, $R_{13}OH$, or with two equivalents of alkoxide, $-OR_{13}$ where $R_{13}$ is as described above. The compound of Formula XVa is prepared according to Reaction Step (10b) from a compound of Formula XV where $Y_2$ is Cl or Br. When alkoxide, $-OR_{13}$ is used it may be provided in either of the methods described above in connection with Reaction Step (10b), and the resulting salt can be acidified to yield a compound of Formula XVI.

When $R_{12}=R_{13}$, Reaction Steps (10b) and (10c) may be combined. Thus, a compound of Formula XIV may be contacted either with at least two equivalents of alkanol, $R_{13}OH$, or with at least three equivalents of alkoxide, $-OR_{13}$.

When a compound of Formula XIV contains two displaceable groups, i.e., both $X_2$ and $Y_2$ are Cl or Br, certain reaction conditions will favor displacement of only one of the group. These conditions are the use of low temperatures and, when alkoxide is used, the slow addition of the stoichiometric amount of alkoxide or alkoxide-generating base to the medium containing the compound of Formula XIV.

When alkoxide is used, both Reaction Steps (10b) and (10c) are preferably run at temperatures within the range of about $-10°$ to 80° C., the range of about 0° to 25° C. being more preferred. Reaction Steps (10b) and (10c) are more sluggish when alkanol is used instead of alkoxide, and more drastic conditions are required for the reaction to go to completion. Thus, higher temperatures, up to and including the boiling point of the alkanol itself, are required.

Reaction Step (10d)

Reaction Step (10d) involves the displacement of the halogen atom in a compound of Formula XIVa by dimethylamino or methylthio nucleophiles. The starting material, a compound of Formula XIVa, is prepared according to Reaction Step (10a), and $Y_4$ is limited to $C_1$-$C_2$ alkyl and $CF_3$.

For this reaction, the compound of Formula XIVa is suspended or dissolved in an inert solvent, such as acetonitrile or THF. At least one equivalent of the nucleophilic species and at least two equivalents of a base are then contacted with the starting material. The first equivalent of base is believed to neutralize the sulfonamido proton. The second equivalent of base generates mercaptide or —N(CH$_3$)$_2$ from the mercaptan or the dialkylamine. Suitable bases include sodium hydride, sodium methoxide and sodium hydroxide.

Suitable reaction temperatures are within the range of about −10° to 80° C., with a range of about 0° to 25° C. being preferred. The product may be isolated by dilution of the reaction mixture with water, mild acidification and filtration.

Compounds of Formula IX, which are intermediates in the preparation of the compounds of Formula II—as described in Equation 8, can also be prepared by the procedures shown in Equations 11 and 12.

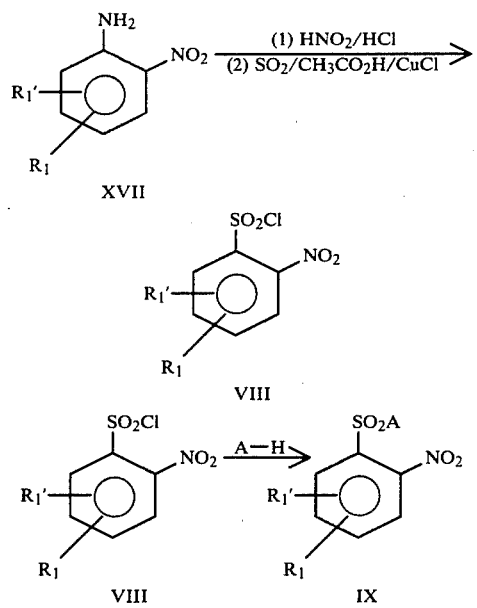

wherein A, R$_1$ and R$_1'$ are as described in Equation 1.

The o-nitroanilines of Formula XVII are well known in the art. The method of converting compounds XVII to compounds VIII is analogous to that described in Equation (8c). The procedures for converting compounds VIII to compounds IX are described in Equation (8a).

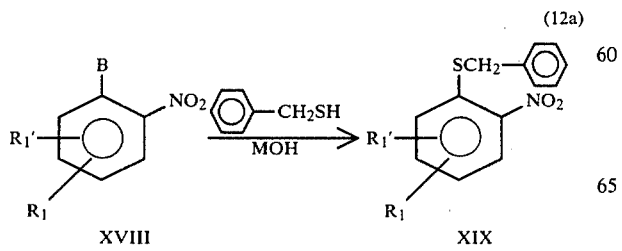

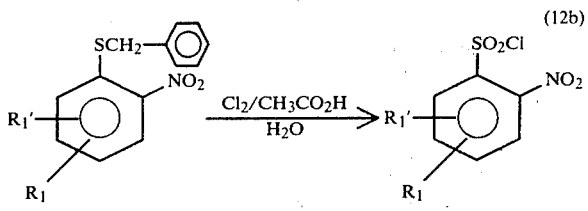

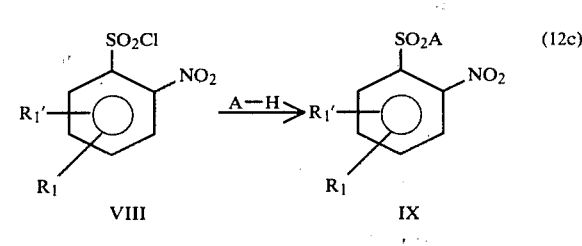

wherein
A, R$_1$, and R$_1'$ are as described in Equation 1;
B is Cl or Br; and
M is Na or K.

In Step (12a), the compounds of Formula XVIII, which are well known in the art, are reacted with benzyl mercaptan in the presence of an equivalent amount of a base such as sodium or potassium hydroxide. The preferred solvent for this reaction is an alcohol such as methyl, ethyl or isopropyl alcohol. The reaction can be carried out at temperatures between 25° and 80° but temperatures of 50°-80° C. are preferred. The products of Formula XIX are isolated by cooling the reaction mixture to 0°-20°, filtering off the precipitated product, and washing this solid with water to remove the by-product alkali halide.

In Step (12b), the compound of Formula XIX is suspended in a mixture of 85-95% acetic acid and 5-15% water. This suspension is treated with at least three molar equivalents of chlorine at 0°-20°. When a clear solution is obtained, the reaction solution is quenched in an excess of ice water and extracted with a solvent such as methylene chloride, chloroform or 1-chlorobutane. The products of Formula VIII are isolated by concentrating this solvent extract in vacuo to remove the solvent and the by-product benzyl chloride. The products are oils or low melting solids and may be used directly in the next step or recrystallized first from such solvents as cyclohexane or 1-chlorobutane.

Compounds of Formula IX, in which A includes certain fluoroalkylamine moieties can also be prepared by the procedure shown in Equation 12a.

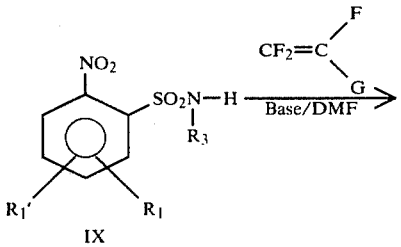

-continued
Equation 12a

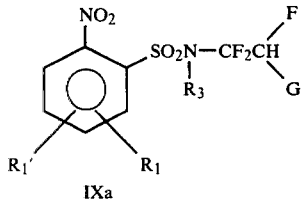
IXa wherein $R_1$ and $R_1'$ are as previously described; $R_3$ is $C_1$-$C_4$ alkyl, and G is F, Cl, Br or $CF_3$.

The reaction described in Equation 12a is accomplished by heating a mixture of the sulfonamide IX, one or two equivalents of the fluoroolefin and a catalytic amount of base in dimethylformamide solution in a pressure vesel at a temperature of between 60° and 130° until a pressure drop is no longer observed. Appropriate bases for this reaction include potassium hydroxide, sodium hydroxide, sodium hydride and sodium metal. The products of the reaction are isolated by quenching the reaction mixture in a large excess of water and extraction with n-butyl chloride or diethylether. Evaporation of the solvent yields the desired sulfonamides IXa as viscous oils.

Compounds of Formula IX in which A includes a benzyloxyamine group may also be prepared by the procedure described in Equation 12b.

Equation 12b

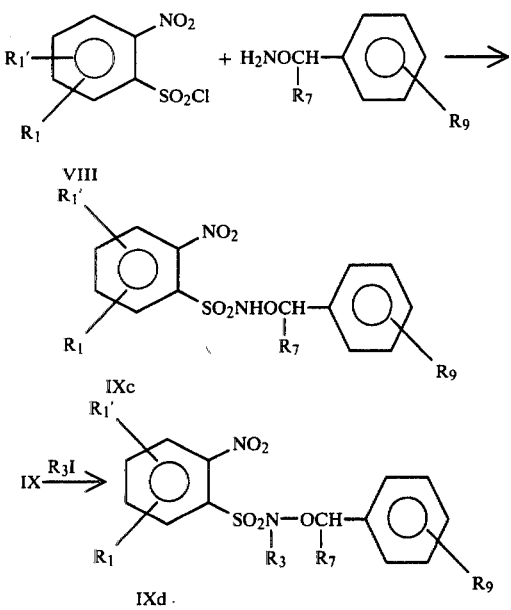

wherein $R_1$, $R_1'$, $R_3$, $R_7$ and $R_9$ are as previously described.

In the first step of Equation 12b, a sulfonyl chloride of Formula XIII is reacted with an appropriate benzyloxyamine, taken in excess to act as an acid acceptor, in diethyl ether or tetrahydrofuran solution at 0°-10°. The reaction is completed by stirring at ambient temperature for 4-24 hours. The solvent is evaporated and the product sulfonamide IXc purified by washing the residue with water to remove the byproduct amine hydrochloride.

In the second step of Equation 12b, the sulfonamide of Formula IXc is stirred at ambient temperature for 18-24 hours with an excess of both an alkyl iodide and anhydrous potassium carbonate or sodium carbonate in acetone or 2-butanone solution. The solvent is evaporated and the residue partitioned between methylene chloride and water. Concentration of the methylene chloride solution affords the compounds of Formula IXd as pale yellow oils.

The compounds of Formula IXd may be converted to compounds of Formula Xd by the procedure described in Equation 12c.

Equation 12c

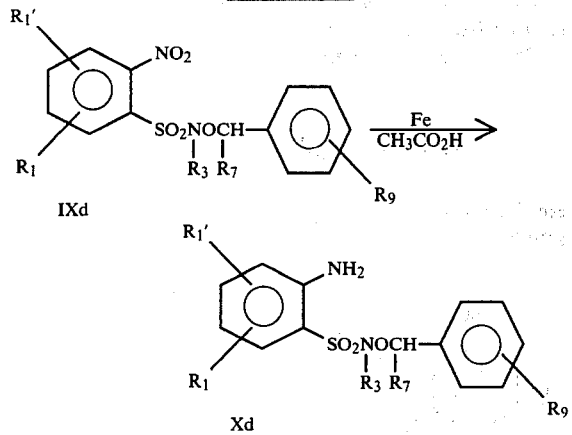

wherein $R_1$, $R_1'$, $R_3$, $R_7$ and $R_9$ are as previously described.

The conversion in Equation 12c is accomplished in the following manner: A solution of the nitro compound IXd in 90% aqueous acetic acid is treated with an excess of iron powder (5 g—atom/mole of IXd) at 80°-90° in several portions. After heating an additional 20 minutes, charcoal is added and the solution filtered through Celite ® and concentrated in-vacuo. The residue is made strongly alkaline with 20% sodium hydroxide then extracted with methylene chloride. Concentration of the organic solution yields the anilines of Formula Xd as viscous oils.

The compounds of Formula Xd may be converted to the compounds of Formula I by the procedures described in Equations 1-8.

Compounds of Formula I in which $R_2$ is hydrogen may be prepared by the procedure described in Equation 12d.

Equation 12d

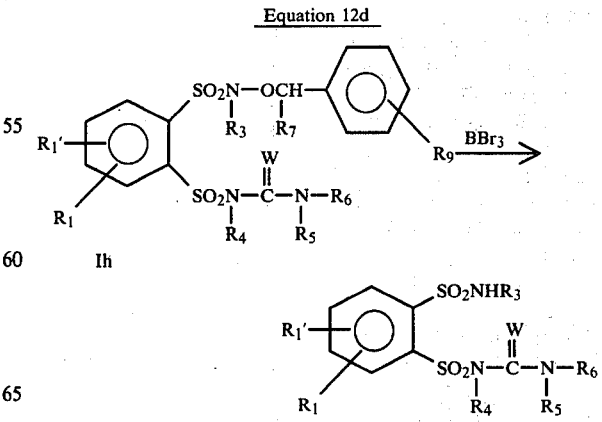

wherein $R_1$, $R_1'$, $R_5$–$R_9$ and W are as described previously.

In the reaction of Equation 12d, an excess of boron tribromide is added to a suspension of the compound of Formula Ih in a solvent such as benzene, toluene or xylene at ambient temperature. The reaction may be completed by stirring at room temperature or it may be necessary to heat the reaction mixture up to 138° for up to 24 hours. After completion, the reaction is quenched by the addition of water and the product triturated with hexane. The products of Formula 12i are solids and are isolated by filtration.

The conversion of compounds VIII to compounds IX is described in Equation (8a).

Compounds of Formula I in which $R_1$ is

$$-N=C=O, \; NHCNHR_d \; \text{and} \; NHCOR_d$$

can be prepared by the procedures described in Equation 13.

used to accelerate the reaction. The products are isolated by removing the solvent via concentration in vacuo.

In Step (13c) the compounds of Formula Id are reacted with amines or alcohols of Formula XXI in an inert solvent such as methylene chloride, chloroform, acetonitrile or tetrahydrofuran at 20°–80° over a period of two to twenty-four hours. The reaction may be accelerated by addition of a catalyst, such as DABCO, and by the use of two equivalents of the amine, XXI. The products, Ie, are isolated by removing the solvent via concentration in vacuo.

Compounds of Formula I in which $R_1$ is $$\underset{NHCR_d}{\overset{O}{\|}}$$

can be prepared by the reaction described in Equation 14.

Equation 13

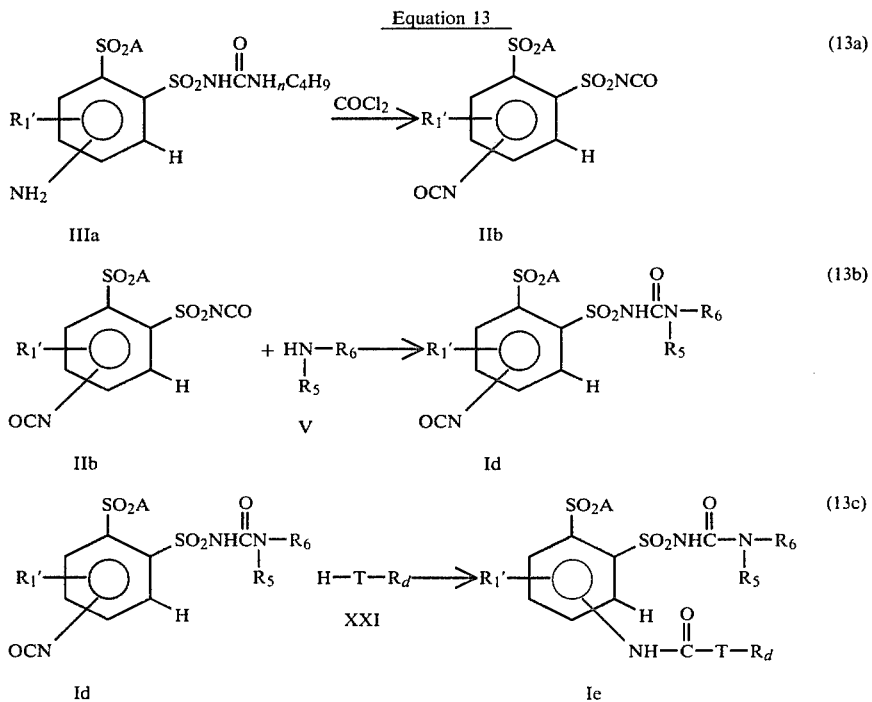

wherein
A, $R_1'$, $R_5$ and $R_6$ are as previously described;
$R_d$ is $C_1$–$C_3$ alkyl; and T is O or NH.

In Step (13a), the compounds of Formula IIIa, which are well known in the art, are added to at least two equivalents of phosgene in an inert solvent such as xylene or chlorobenzene at 0°–5°. A slow stream of phosgene is then introduced and the reaction temperature raised to 130° (reflux). Refluxing the reaction mixture for 1–2 hours, followed by purgation with nitrogen, filtration, and concentration yields the products of Formula IIb, as viscous oils. These compounds may be further purified by vacuum distillation.

In Step (13b), the compounds of Formula IIb are reacted with the aminoheterocycles of Formula V in an inert solvent such as methylene chloride, acetonitrile, or tetrahydrofuran at 20°–50° over a period of two to twenty-four hours. A catalyst, such as DABCO, may be Equation 14

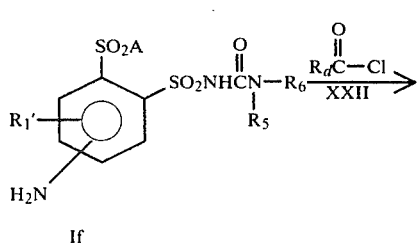

-continued

Equation 14

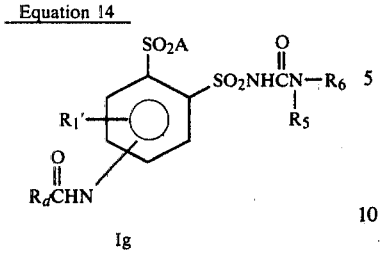

wherein A, $R_1'$, $R_d$, $R_5$ and $R_6$ are as previously described.

In the procedure described in Equation 14, the compounds of Formula If are reacted with an acid chloride of Formula XXII in an inert solvent such as chloroform, methylene chloride or tetrahydrofuran at ambient temperature in the presence of an acid acceptor such as pyridine or triethylamine. The reaction takes four to twenty-four hours for completion. Both the acid chloride, XXII, and the acid acceptor may be taken in excess to hasten the completion of the reaction. The products, Ig, are isolated by filtering-off the by-product amine hydrochloride and concentrating the filtrate in vacuo. The crude products thus obtained may be purified by recrystallization or by column chromatography.

The compounds of Formula IA can be prepared from the compounds of Formula I in which W is sulfur by the process described in Equation 15.

Equation 15

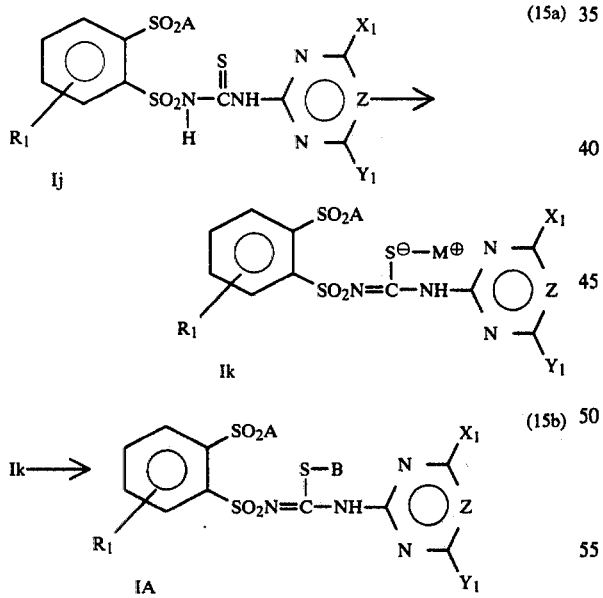

wherein

A, $R_1$, $X_1$, $Y_1$ and Z are as described previously and B is $C_1$-$C_6$ alkyl; $CH_2CH_2OCH_3$; $CH_2CH_2OCH_2CH_3$;

$CH_2CH_2CH_2OCH_3$; $CH_2Q$; $\underset{CH_3}{CH-Q}$;

where Q is

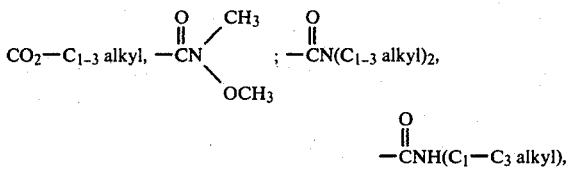

$CO_2$—$C_{1-3}$ alkyl, $-\overset{O}{\underset{\|}{C}}N\overset{CH_3}{\underset{OCH_3}{<}}$; $-\overset{O}{\underset{\|}{C}}N(C_{1-3}\text{ alkyl})_2$, $-\overset{O}{\underset{\|}{C}}NH(C_1-C_3\text{ alkyl})$, phenyl, phenyl substituted with chlorine, CN, $C_{2-4}$ alkenyl, $C_{2-4}$ alkynyl, $-OR_{11}'$, where $R_{11}'$ is $C_1$-$C_4$ alkyl, $-CH_2OCH_2CH_2OCH_3$ or $-CH_2OCH_2CH_2OCH_2CH_3$ and M is an alkali or alkaline earth metal.

In step (15a) the thiourea of Formula Ij is treated with an alkali or alkaline earth alkoxide, hydride, hydroxide or carbonate in tetrahydrofuran or diethyl ether suspension to obtain the salt Ik at ambient temperature up to 62°. In step (15b) the salt suspension as solution is treated with the appropriately substituted iodide or bromide at 35° to 62° for 1–4 hours. The reaction mixture is then cooled to ambient temperature. If the product is insoluble, it may be isolated by filtration from the reaction mixture. If the product is soluble in the reaction solvent, it may be isolated by the reaction solvent, it may be isolated by evaporating the solvent and triturating the residue with a solvent such as cyclohexane or 1-chlorobutane. The product Ia may be purified by recrystallization from a suitable solvent such as acetonitrile.

Agriculturally suitable salts of compounds of Formula I and Formula IA are also useful herbicides and can be prepared in a number of ways known to the art. For example, metal salts can be made by treating compounds of Formula 1 with a solution of an alkali or alkaline earth metal salt having a sufficiently basic anion (e.g. hydroxide alkoxide, carbonate or hydride) quaternary amine salts can be made by similar techniques. Detailed examples of such techniques are given in U.S. Pat. No. 4,127,405, the disclosure of which is herein incorporated by reference.

The compounds of this invention and their preparation are further illustrated by the following examples wherein temperatures are given in degrees centigrade and all parts are by weight unless otherwise indicated.

EXAMPLE 1 o-Nitro-N,N-diethylbenzenesulfonamide

To a solution of 132.6 g of o-nitrobenzenesulfonyl chloride in 700 ml of tetrahydrofuran was added 88.5 g of diethylamine at 5°–15°. The reaction mixture was stirred at room temperature for 1 hour before the precipitated diethylamine hydrochloride was removed by filtration. The filtrate was evaporated to dryness in-vacuo and the residue dissolved in 1-chlorobutane. The 1-chlorobutane solution was washed with water, dried over magnesium sulfate and evaporated in-vacuo to give 122.4 g of o-nitro-N,N-diethylbenzenesulfonamide as a dark oil.

NMR(CDCl$_3$)δ: 1.1–1.4 [t, 6.1H, (CH$_3$CH$_2$)$_2$N-]; 3.3–3.8 [qt, 3.8H, (CH$_3$CH$_2$)$_2$N-]; 8.0–8.6 (m, 4.1H, 4 aromatics).

EXAMPLE 2 o-Amino-N,N-diethylbenzenesulfonamide

In a pressure vessel a mixture of 133 g of o-nitro-N,N-diethylbenzenesulfonamide, 5 g of 10% palladium on carbon, and 500 ml of ethyl acetate was shaken at 130° under 500 psi hydrogen pressure until hydrogen was no longer absorbed. The reaction mixture was cooled and the catalyst filtered off. Evaporation of the solvent in-vacuo gave 123 g of o-amino-N,N-diethylbenzenesulfonamide as a viscous oil which slowly crystallized to a solid, m.p. 45°–51°.

NMR(CDCl$_3$)δ: 1.0–1.3 [t, 6.7H, (CH$_3$CH$_2$)$_2$N-]; 3.0–3.5 [qt, 3.6H, (CH$_3$CH$_2$)$_2$N-]; 4.8–5.2 (broad, 1.7H, NH$_2$); 6.5–7.7 (m, 4.0H, 4 aromatics).

EXAMPLE 3

N,N-Diethyl-1,2-benzenedisulfonamide

To a solution of 114 g of o-amino-N,N-diethylbenzenesulfonamide in a mixture of 400 ml of concentrated hydrochloric acid and 100 ml of glacial acetic acid was added a solution of 50 g of sodium nitrite in 130 ml of water at −5° to 0°. The solution was stirred at 0° for 15 minutes then poured into a mixture of 14 g of cuprous chloride and 100 ml of liquid sulfur dioxide in 550 ml of glacial acetic acid at 0°–5°. This mixture was stirred at 0° for 15 minutes then at room temperature for 3 hours before pouring into three liters of ice water. The crude sulfonyl chloride was filtered off and washed with water. It was then dissolved in 1 l of ethyl ether, washed with water and dried over magnesium sulfate. To this ether solution was added 20 ml of liquid anhydrous ammonia at 5°–15°. After stirring overnight at room temperature the solid was filtered off, washed with water, ethanol and then 1-chlorobutane, Oven drying at 60° gave 91.8 g N,N-diethyl-1,2-benzenedisulfonamide, m.p. 156°–9°.

NMR(DMSO)δ: 0.9–1.2 [t, 6.0H, (CH$_3$CH$_2$)$_2$N-]; 3.2–3.6 [qt, 3.8H, (CH$_3$CH$_2$)$_2$N-]; ~7.2 (broad singlet, 2.1H, NH$_2$); 7.7–8.4 (m, 4.1H, 4 aromatics).

EXAMPLE 4 o-N,N-Diethylsulfamoylbenzenesulfonyl isocyanate

A solution of 13.2 g of N,N-diethyl-1,2-benzenedisulfonamide, 4.5 g of n-butylisocyanate, and 0.2 g of 1,4-diaza[2,2,2]bicyclooctane (DABCO) in 90 ml of mixed xylenes was heated to 135°. To this solution ws added 3.3 ml of liquid phosgene at such a rate that the temperature was maintained between 125° and 135° (about 2 hours). The temperature was kept at 130° for ½ hour after the addition. The solution was cooled and filtered to remove a small amount of insoluble solid then concentrated at 60°–70° in-vacuo. The residue of o-N,N-diethylsulfamoylbenzenesulfonyl isocyanate was an oil weighing 16.8 g and was sufficiently pure for further reaction.

EXAMPLE 5

N,N-Diethyl-N′-[(4-methoxy-6-methylpyrimidin-2-yl)aminocarbonyl]-1,2-benzenedisulfonamide A mixture of 0.8 g of 2-amino-4-methoxy-6-methylpyrimidine, 2.8 g of the crude sulfonyl isocyanate from Example 4 and a few crystals of DABCO in 25 ml of acetonitrile was stirred at room temperature for 16 hours. A small amount of unreacted aminopyrimidine was filtered off and the filtrate concentrated in-vacuo to give a hard glass. Crystallization from methanol gave 0.9 g of N,N-diethyl-N′[(4-methoxy-6-methylpyrimidin-2-yl)aminocarbonyl]-1,2-benzenedisulfonamide as a white solid, m.p. 170°–2°.

Anal. Calcd. for C$_{17}$H$_{23}$N$_5$O$_6$S$_2$: C, 44.62; H, 5.07; N, 15.31. Found: C, 44.5, 44.4; H, 5.09, 5.09; N, 15.4, 15.5.

NMR(DMSO-d$_6$)δ: 0.9–1.2 [t,6.0H, (CH$_3$CH$_2$)$_2$N-]; 2.3 (S, 2.8H, Het—CH$_3$); 3.1–3.5 [qt, 4.3H, (CH$_3$CH$_2$)$_2$N-]; 3.9 (S, 3.0H, Het—OCH$_3$); 6.5 (S, 0.9H, Het—H); 7.7–8.5 (m, 4.3H, 4 aromatics); 10.6 (S, 1.0H, NH); 13.4 (S, 0.8H, NH).

EXAMPLE 6

N,N-Diethyl-N′-[(4,6-dimethoxy-1,3,5-triazin-2-yl)aminocarbonyl]-1,2-benzenedisulfonamide A mixture of 0.9 g of 2-amino-4,6-dimethoxy-1,3,5-triazine, 2.8 g of the crude sulfonyl isocyanate from Example 4 and a few crystals of DABCO in 25 ml of acetonitrile was stirred at room temperature for 16 hours. A small amount of untreated triazine was filtered off and the filtrate concentrated in-vacuo to a hard glass. Crystallization from methanol gave 0.6 g of N,N-diethyl-N′[(4,6-dimethoxy-1,3,5-triazin-2-yl)aminocarbonyl]-1,2-benzenedisulfonamide as a white solid, m.p. 175°–7°.

NMR(DMSO-d$_6$)δ: 0.9–1.2 [t, 6.0H, (CH$_3$CH$_2$)$_2$N-]; 3.1–3.5 [qt, 4.3H, (CH$_3$CH$_2$)$_2$N-]; 3.95 (S, 5.5H, —OCH$_3$'s); 7.9–8.5 (m, 4.1H, 4 aromatics); 11.2 (S, 0.9H, NH); 12.4 (S, 1.1H, NH).

EXAMPLE 7

2-Nitro-1-[(phenylmethyl)thio]-4-trifluoromethylbenzene

To a mixture of 225.6 g of 4-chloro-3-nitrobenzotrifluoride and 136 g of benzyl mercaptan in 1.5 l of ethyl alcohol, at reflux, was added a solution of 72.5 g of 85% KOH in 120 ml of water over a 45 minute period. Reflux was continued for an additional three hours. The reaction mixture was cooled to 5° C. The precipitate was filtered off, washed with ethanol and water and dried to give 273.2 g of 2-nitro-1-[(phenylmethyl)thio]-4-trifluoromethylbenzene as a bright yellow solid, m.p. 132°–136°.

NMR(DMSO-d$_6$)δ: 4.45 (s, 1.9H, SCH$_2$φ); 7.2–7.7 (m, 5.0H, 5 aromatics); 7.9–8.2 (m, 2.1H, 2 aromatics); 8.5 (s, 1.0H, 1 aromatic).

EXAMPLE 8

N,N-Dimethyl-2-nitro-4-(trifluoromethyl)benzenesulfonamide

To a suspension of 156.5 g of 2-nitro-1-[(phenylmethyl)thio]-4-trifluoromethylbenzene in a mixture of 800 ml of acetic acid and 100 ml of water was added 78 ml of liquid chlorine at 10°–18° over a 1 hour period as the suspension gradually turned into a clear solution. The solution was stirred at 18°–25° for 2 hours, then poured into 1 l of ice water. The mixture was extracted with 1-chlorobutane and the 1-chlorobutane extract washed well with water. The solution was dried over MgSO$_4$ and stripped finally at 70°–80°/1–2 mm, to give 164 g of crude sulfonyl chloride as a light yellow oil. This oil was dissolved in 600 ml of methylene chloride, cooled to 5°, and treated with 75 ml of liquid dimethylamine at 5°–15°. After stirring at 25° for 1 hour, the reaction mixture was washed with water, dried over MgSO$_4$, and stripped in vacuo to give a crude solid. This solid was slurried in ethanol, filtered and washed with ethanol, and dried to give 109.1 g of N,N-dimethyl-2-nitro-4-(trifluoromethyl)benzenesulfonamide, m.p. 102°–104.5°.

NMR(DMSO-d$_6$)δ: 2.9 (s, 6.1H, NMe$_2$); 8.3 (s, 2.0H, 2 aromatics); 8.7 (s, 0.9H, 1 aromatic).

Anal. Calcd. for $C_9H_9F_3N_2O_4S$: C, 36.25; H, 3.04; N, 9.39; S, 10.75. Found: C, 36.4, 3.65; H, 3.00, 3.04; N, 9.58, 9.52; S, 11.1, 11.0.

EXAMPLE 9

2-Amino-N,N-dimethyl-4-(trifluoromethyl)benzenesulfonamide

In a pressure vessel, 109 g of N,N-dimethyl-2-nitro-4-(trifluoromethyl)benzenesulfonamide, 250 ml of ethyl acetate and 5 g of 10% palladium-on-carbon were shaken at 130° under 500 psi hydrogen pressure until no more hydrogen was absorbed, as determined by no additional pressure drop. The reaction mixture was cooled and the catalyst filtered off. The solution was stripped in vacuo to give 95.2 g of 2-amino-N,N-dimethyl-4-(trifluoromethyl)benzenesulfonamide as a slowly crystalizing oil, m.p. 65°-70° C.

NMR(CDCl$_3$)δ: 2.8 (s, 5.8H, NMe$_2$); 5.1–5.6 (broad, 2.2H, NH$_2$); 6.9–7.9 (m, 3.0H, 3 aromatics).

EXAMPLE 10

$N^1,N^1$-Dimethyl-4-(trifluoromethyl)-1,2-benzenedisulfonamide

To a suspension of 38.0 g, of 2-amino-N,N-dimethyl-4-(trifluoromethyl)benzenesulfonamide in a mixture of 115 ml of concentrated hydrochloric acid and 40 ml of glacial acetic acid was added a solution of 14.0 g of sodium nitrite in 40 ml of water at −5° to 0° over a 30 minute period. The resulting diazonium solution was stirred at 0° for 15 minutes. This diazonium solution was then added to a solution of 4.0 g of cuprous chloride and 26 ml of liquid sulfur dioxide in 175 ml of glacial acetic acid at 5° over a 10 minute period. The resulting mixture was stirred at 0° for 1 hour and at 25° for 2 hours before pouring into 1 l of ice water. The precipitated sulfonyl chloride which formed was filtered off and washed well with water. The still-wet sulfonyl chloride was suspended in 350 ml of diethyl ether, cooled to 5° and treated with 7.0 ml of liquid ammonia. The reaction mixture was stirred at room temperature for 1 hour. The precipitate was filtered-off, washed with ether, water and then ethanol to give 22.4 g of $N^1$, $N^1$-dimethyl-4-(trifluoromethyl)-1,2-benzenedisulfonamide as a white solid, m.p. 189°-191°.

NMR(DMSO-d$_6$)δ: 2.7 (s, 6.1H, —NMe$_2$); 7.3 (broad singlet, 1.9H, —SO$_2$NH$_2$); 8.0–8.4 (m, 3.0H, 3 aromatics).

EXAMPLE 11

N'-(Butylaminocarbonyl)-N,N-dimethyl-4-(trifluoromethyl)-1,2-benzenedisulfonamide A mixture of 49.7 g of N',N'-dimethyl-4-(trifluoromethyl)-1,2-benzenedisulfonamide 22.5 g of n-butylisocyanate, and 31.1 g of anhydrous potassium carbonate in 600 ml of 2-butanone was stirred at reflux for four hours. The mixture was cooled to 25° and poured into 1.6 l of ice water. The solution was acidified to pH=1 with concentrated hydrochloric acid. The precipitate was filtered off and washed with water and 1-chlorobutane. Drying overnight at 60° in vacuo gave 55.6 g of N'-(butylaminocarbonyl)-N,N-dimethyl-4-(trifluoromethyl)-1,2-benzenedisulfonamide as a white solid, m.p. 128°-130°.

NMR(DMSO-d$_6$)δ: 0.8–1.6 (m, 7.7H, 7 butyl hydrogens); 2.8–3.5 (m, 7.5H, NMe$_2$+CH$_2$NH); 6.8–7.1 (m, 0.9H, NHCH$_2$); 8.4–8.8 (m, 3.1H, 3 aromatics); ~10.3 (broad, 0.9H, NH).

EXAMPLE 12

2-(N,N-Dimethylsulfamoyl)-5-(trifluoromethyl)benzenesulfonylisocyanate

A solution of 12.5 g of N'-(butylaminocarbonyl)-N,N-dimethyl-4-(trifluoromethyl)-1,2-benzenedisulfonamide, and 0.1 g of DABCO in 75 ml of mixed xylenes was heated to 136°. To this solution was added 2.2 ml of liquid phosgene over a period of two hours at a rate that the temperature was maintained between 125° and 135°. The temperature was kept at 130° for ½ hour after the addition. The solution was cooled and filtered under a nitrogen atmosphere to remove a small amount of insoluble solid then concentrated at 60°-70° in vacuo. The residue of 2-(N,N-dimethylsulfamoyl)-5-(trifluoromethyl)benzenesulfonylisocyanate was an oil weighing 10.4 g and was sufficiently pure for further reaction.

EXAMPLE 13

$N^2$[(4,6-Dimethoxypyrimidin-2-yl)aminocarbonyl]-$N^1$, $N^1$-dimethyl-4-(trifluoromethyl)-1,2-benzenedisulfonamide A mixture of 2.6 g of crude 2-(N,N-dimethylsulfamoyl)-5-(trifluoromethyl)benzenesulfonylisocyanate, 0.9 g of 2-amino-4,6-dimethoxypyrimidine and a few crystals of DABCO in 15 ml of acetonitrile was stirred under a nitrogen atmosphere at 25° overnight. The precipitate was filtered off, washed with acetonitrile and dried to give 0.7 g of $N^2$-[(4,6-dimethoxypyrimidin-2-yl)aminocarbonyl]-$N^1$, $N^1$-dimethyl-4-(trifluoromethyl)-1,2-benzenedisulfonamide, m.p., 194°-6° (d).

Anal. Calcd. for $C_{16}H_{18}F_3N_5O_7S_2$: C, 37.43; H, 3.53; N, 13.64; F, 11.10. Found: C, 37.5, 37.6; H, 3.57, 3.65; N, 14.0, 14.0; F, 11.47

NMR(DMSO-d$_6$)δ: 2.9(s, 5.8H, NMe$_2$); 3.9(s, 6.1H, Het—OCH$_3$'s); 6.0(s, 1.2H, Het—H); 8.2–8.6(m, 2.9H, 3 aromatics); 10.8(broad, 1.0H, NH); ~13(broad, 1.0H, NH).

EXAMPLE 14

2,2,2-Trifluoroethyl 2-nitrobenzenesulfonate

To a solution of 110.5 g of o-nitrobenzenesulfonyl chloride and 50.0 g of 2,2,2-trifluoroethanol in 600 ml of diethyl ether was added 52.0 g of triethylamine at 5°-15° over a 45 minute period. The reaction mixture was stirred at 25° for 1 hour then washed with water, dried over MgSO$_4$, and stripped in vacuo to give 2,2,2-trifluoroethyl 2-nitrobenzenesulfonate as an oil weighing 110.3 g.

NMR(CDCl$_3$)δ: 4.3–4.8(qt, 1.8H, CH$_2$CF$_3$) 7.8–8.4(m, 4.2H, 4 aromatics).

EXAMPLE 15

2,2,2-Trifluoroethyl 2-aminobenzenesulfonate

In a pressure vessel, 107 g of 2,2,2-trifluoroethyl 2-nitrobenzenesulfonate and 8 g of 5% palladium-on-carbon in 300 ml of ethyl acetate was heated to 110° and shaken under 500 psi hydrogen pressure until hydrogen was no longer absorbed. The reaction mixture was cooled and the catalyst filtered off. The filtrate was stripped in vacuo to give 87.5 g of 2,2,2-trifluoroethyl 2-aminobenzenesulfonate as a dark oil.

NMR(CDCl$_3$)δ: 4.0–0.4(qt, 2.0H, CH$_2$CF$_3$); 4.8–5.4(broad, 1.9H, NH$_2$); 6.5–7.8(m, 4.1H, 4 aromatics).

EXAMPLE 16

2,2,2-Trifluoro 2-(aminosulfonyl)benzenesulfonate

Using a procedure analogous to that described in Example 10, 63.8 g of the product of Example 15 was converted to 38.4 g of 2,2,2-trifluoro 2-(aminosulfonyl)-benzenesulfonate, m.p. 97°–100° (recrystallized from 1-chlorobutane).

NMR(DMSO-d$_6$)δ: 4.4–4.9(qt. 1.9H, CH$_2$CF$_3$); 6.8–7.1(broad singlet, 1.9H, SO$_2$NH$_2$); 7.7–8.6(m, 4.2H, 4 aromatics).

EXAMPLE 17

(2,2,2-Trifluoroethyl) 2-[[(butylamino)carbonyl]aminosulfonyl]benzenesulfonate

Using a procedure analogous to that described in Example 11, 35.1 g of the product of Example 16 was converted to 45.0 g of (2,2,2-trifluoroethyl) 2-[[(butylamino)carbonyl]aminosulfonyl]benzenesulfonate, m.p. 140°–2.5°.

NMR(DMSO-d$_6$)δ: 0.7–1.4(m, 7.2H, 7 butyl hydrogens); 2.7–3.2(m, 2.1H, 2 butyl hydrogens); 4.6–5.1(qt, 2.0H, CH$_2$CF$_3$); 6.5–6.9(broad t, 0.9H, NHCH$_2$); 7.9–8.6(m, 3.8H, 4 atomatics).

EXAMPLE 18

2,2,2-Trifluoroethyl 2-(isocyanatosulfonyl)benzenesulfonate

Using a procedure analogous to that described in Example 12, 20.6 g of the product of Example 17 was converted to 16.6 g of 2,2,2-trifluoroethyl 2-(isocyanatosulfonyl)benzenesulfonate, obtained as a crude oil.

EXAMPLE 19

(2,2,2-Trifluoroethyl) 2-[[(4,6-dimethoxypyrimidin2-yl)aminocarbonyl]aminosulfonyl]benzenesulfonate Using a procedure analogous to that described in Example 13, 2.7 g of the product of Example 18 was converted to 1.9 g of (2,2,2-trifluoroethyl) 2-[[4,6-dimethoxypyrimidin-2-yl)aminocarbonyl]aminosulfonyl]-benzenesulfonate, m.p. 203°–5°.

Anal. Calcd. for C$_{15}$H$_{15}$F$_3$N$_4$O$_8$S$_2$: C, 36,00; H, 3.02; N, 11.20. Found: C, 36.1, 36.7; H, 2.96, 2.90; N, 11.2, 11.3.

NMR(DMSO-d$_6$)δ: 3.85(s, 5.9H, Het-OCH$_3$'s); 4.7–5.1(qt, 2.2H, CH$_2$CF$_3$); 5.9(s, 1.2H, Het-H); 8.0–8.7(m, 4.1H, 4 aromatics); 10.7(s, 0.9H, NH); ~13(broad, 0.7H, NH).

EXAMPLE 20

N,N-Dimethyl-4-methoxy-2-nitrobenzenesulfonamide

A mixture of 84.0 g of 4-methoxy-2-nitroaniline, 400 ml of conc. hydrochloric acid, and 200 ml of acetic acid was treated with a solution of 50 g of sodium nitrite in 120 ml of water over a 45 minute period at −5° to 0°. The resulting solution was stirred at 0° for 15 minutes. This diazonium solution was added to a solution of 12 g of cuprous chloride and 100 ml of sulfur dioxide in 600 ml of acetic acid over 15 minutes at 0°–5°. The mixture was stirred at 0° for 1 hour and at 25° for 2 hours before pouring into 4 l of ice water. The precipitated sulfonyl chloride was filtered and washed well with water. The still-wet sulfonyl chloride was suspended in 600 ml of diethyl ether, cooled to 0°, and treated with 55 ml of liquid dimethyl amine at 0°–10°. After stirring at room temperature for 30 minutes, the precipitate was filtered and washed with ether, then water. Drying at 60° in vacuo gave 92.0 g of N,N-dimethyl-4-methoxy-2-nitrobenzenesulfonamide as a white solid, m.p. 90°–92°.

NMR(DMSO-d$_6$)δ: 2.7(s, 6.1H, —NMe$_2$); 3.9(s, 2.9H, OCH$_3$); 7.2–8.0(m, 2.9H, 3 aromatics).

EXAMPLE 21

N,N-Dimethyl-2-amino-4-methoxybenzene-sulfonamide

In a procedure analogous to that described in Example 9, 90.0 g of the product of Example 20 was converted to 66.4 g of N,N-dimethyl-2-amino-4-methoxybenzenesulfonamide, obtained as a dark, slowly crystalizing oil, m.p. 59°–64°.

NMR(CDCl$_3$)δ: 2.7(s, 5.7H, NMe$_2$); 3.7(s, 3.0H, OCH$_3$); 4.9–5.3(broad, 2.0H, NH$_2$); 6.2–6.5(m, 2.2H, 2 aromatics); 7.3–7.6(m, 1.2H, 1aromatic).

EXAMPLE 22

N$^1$,N$^1$-Dimethyl-4-methoxybenzene-1,2-disulfonamide

Using a procedure analogous to that described in Example 10, 58.0 g of the product of Example 21 was converted to 34.8 g of N$^1$,N$^1$-dimethyl-4-methoxybenzene-1,2-disulfonamide, m.p. 106°–9°.

NMR(DMSO-d$_6$)δ: 2.8(s, 5.9H, —NMe$_2$); 3.9(s, 3.1H, OCH$_3$); 7.0–8.1(m, 5.0H, 5 aromatics+SO$_2$NH$_2$).

EXAMPLE 23

N'-(Butylaminocarbonyl)-N,N-dimethyl-4-methoxy)-1,2-benzenedisulfonamide

Using a procedure analogous to that described in Example 11, 33.0 g of the product of Example 22 was converted to 43.0 g of N'-(butylaminocarbonyl)-N,N-dimethyl-4-methoxy-1,2-benzenedisulfonamide, obtained as a viscous oil.

NMR(DMSO-d$_6$)δ: 0.6–1.5(m, 8.7H, 8 butyl hydrogens); 2.6–3.1(m, 7.6H, 2 butyl hydrogens+NMe$_2$); 3.85(s, 2.7H, OCH$_3$); 6.7–7.0(broad t, 0.7H, CH$_2$NH); 7.2–8.1(m, 2.7H, 3 aromatics); ~9.8(broad, 0.7H, NH).

EXAMPLE 24

N,N-Dimethyl-2-(isocyanatosulfonyl)-4-methoxybenzene-sulfonamide

Using a procedure analogous to that described in Example 12, 19.7 g of the product of Example 23 was converted to 16.0 g of N,N-dimethyl-2-(isocyanatosulfonyl)-4-methoxybenzenesulfonamide, obtained as a viscous oil.

EXAMPLE 25

N$^2$-[(4-Methoxy-6-methylpyrimidin-2-yl)aminocarbonyl]-N$^1$,N$^1$-dimethyl-4-methoxy-1,2-benzenedisulfonamide Using a procedure analogous to that described in Example 13, 2.7 g of the product of Example 24 was converted to 1.2 g of N$^2$-[(4-methoxy-6-methylpyrimidin-2-yl)aminocarbonyl]-N$^1$,N$^1$-dimethyl-4-methoxy-1,2-bezenedisulfonamide, m.p. 205°–7° (d).

NMR(DMSO-d$_6$)δ:2.4(s, 3.1H, Het-CH$_3$); 2.8(s, 6.1H, NMe$_2$); 3.9(s, 6.1H, 2 OCH$_3$'s) 6.5(s, 1.0H, Het-H); 7.3–8.1(m, 3.0H, 3 aromatics); 10.5(s, 0.9H, NH); 13.5(broad, 0.8H, NH).

EXAMPLE 26

N-Methyl-N-[1,1,2,2-tetrafluoroethyl)-2-nitrobenzene]-sulfonamide

A solution of 72 g of N-methyl-2-nitrobenzenesulfonamide, 35 g of tetrafluoroethylene and 4 g of powdered potassium hydroxide in 150 ml of dimethylformamide was heated at 85° for 3 hours in a pressure vessel. The reaction mixture was cooled to 25° and poured into 800 ml of water. A heavy oil was separated and the aqueous layer extracted with 150 ml of 1-chlorobutane. The heavy oil, the 1-chlorobutane extract and an additional 300 ml of 1-chlorobutane were combined and washed three times with water. The organic solution was dried over magnesium sulfate and concentrated in-vacuo to yield 85.1 g of N-methyl-N-(1,1,2,2-tetrafluoroethyl)-2-nitrobenzenesulfonamide as a viscous orange oil.

NMR(DCDl$_3$)$\delta$: 3.1–3.3(m, 2.6H, N-CH$_3$); 5.2–7.3(tt, 1.0H, JFCH=57 Hz and JFCCH=5 Hz, CF$_2$H); 7.7–8.3(m, 4.4H, 4 aromatics).

EXAMPLE 27

N-Methyl-N-(1,1,2,2-tetrafluoroethyl)-2-aminobenzenesulfonamide

Using a procedure analogous to that described in Example 15, 82.0 g of the product of Example 26 was converted to 65.4 g of N-methyl-N-(1,1,2,2-tetrafluoroethyl)-2-aminobenzenesulfonamide, as a viscous oil.

NMR(CDCl$_3$)$\delta$: 2.9(t, J=3 Hz, 2.7H, CH$_3$NCF$_2$—); 4.5–5.4(broad, 1.9H, NH$_2$); 5.4–5.6 and 6.4–7.8(m, 5.4H, 4 aromatics+CF$_2$H).

EXAMPLE 28

N-Methyl-N-(1,1,2,2-tetrafluoroethyl)-1,2-benzenedisulfonamide

Using a procedure analogous to that described in Example 10, 60.0 g of the product of Example 27 was converted to 32.0 g of N-methyl-N-(1,1,2,2-tetrafluoroethyl)-1,2-benzenedisulfonamide, m.p. 102°–107°.

NMR(DMSO-d$_6$)$\delta$: 3.3(broad singlet, 2.9H, CH$_3$N); 6.05, 6.95, 7.85(tt, 1.0H, CF$_2$H); 7.5(broad singlet, 1.8H, SO$_2$NH$_2$); 7.9–8.7(m, 4.3H, 4 aromatics).

| Anal. Calcd. for C$_9$H$_{10}$N$_2$O$_4$S$_2$F$_4$: | C, 30.86; |
|---|---|
| H, 2.88; N, 8.00. | |
| | Found: C, 31.1; |
| H, 2.82, N, 8.01. | 31.2 |
| 2,69   8.04 | |

EXAMPLE 29

N'-(Butylaminocarbonyl)-N-methyl-N-(1,1,2,2-tetrafluoroethyl)-1,2-benzenedisulfonamide Using a procedure analogous to that described in Example 11, 24.5 g of the product of Example 28 was converted to 31.0 g of N'-(butylaminocarbonyl)-N-methyl-N-(1,1,2,2-tetrafluoroethyl)-1,2-benzenedisulfonamide, m.p. 146°–152°.

NMR(DMSO-d$_6$)$\delta$: 0.6–1.5(m, 7.2H, 7 butyl hydrogens); 2.7–3.1(m, 2.0H, 2 butyl hydrogens); 3.1–3.3(s, 2.7H, CH$_3$N); 5.9, 6.85, 7.75(tt, 1.0H, CF$_2$H); 6.65(t, 1.0H, CH$_2$-NH) 7.9–8.5(m, 4.3H, 4 aromatics); 10.2(s, 0.8H, NH).

EXAMPLE 30

N-Methyl-N-(1,1,2,2-tetrafluoroethyl)benzenesulfonylisocyanate

Using a procedure analogous to that described in Example 12, the product of Example 29 was converted to N-methyl-N-(1,1,2,2-tetrafluoroethyl)benzenesulfonylisocyanate, isolated as a viscous oil.

IR(Neat): 2230 cm$^{-1}$ (SO$_2$NCO).

EXAMPLE 31

N'[(4-Methoxy-6-methylpyrimidin-2-yl)aminocarbonyl]-N-methyl-N-(1,1,2,2-tetrafluoroethyl)-1,2-benzenedisulfonamide A mixture of 3.1 g of the product of Example 30, 0.8 g of 2-amino-4-methyl-6-methoxypyrimidine and a few crystals of DABCO in 15 ml of acetonitrile was stirred at 50° for 1 hour and at 25° overnight. The precipitate was filtered off, washed with acetonitrile and dried to give 1.9 g of N'-[(4-methoxy-6-methylpyrimidin-2-yl)aminocarbonyl]-N-methyl-N-tetrafluoroethyl)-1,2-benzenedisulfonamide, m.p. 176°–177° (d).

| Anal. Calcd. for C$_{16}$H$_{17}$F$_4$N$_5$O$_6$S$_2$: | C, 37.28; |
|---|---|
| H, 3.32;   N, 13.59. | |
| | Found:    C, 37.3; |
| | 37.3 |
| H, 3.37;   N, 13.8. | |
| 3.35       13.8 | |

NMR(DMSO-d$_6$)$\delta$: 2.3(s, 2.9H, Het-CH$_3$); 3.2(broad singlet, 2.9, CH$_3$-N); 3.9(s, 2.9H, Het-OCH$_3$); 5.9, 6.8, 7.7(tt, 0.9H, CF$_2$H); 6.65(s, 1.0H, Het-H); 8.0–8.7(m, 4.4H, 4 aromatics); 10.7(s, 1.0H, NH); ~13.9(broad singlet, 0.9H, NH).

EXAMPLE 32

N-(Phenylmethoxy)-2-nitrobenzenesulfonamide

A solution of 96.4 g of O-benzylhydroxylamine in 80 ml of tetrahydrofuran was added to a solution of 86.8 g of o-nitrobenzenesulfonyl chloride in 400 ml of tetrahydrofuran at 5°–10°. After stirring at ambient temperature for 16 hours the solvent was evaporated. The residue was washed with water, filtered and dried to give 112.6 g of N-(phenylmethoxy)-2-nitrobenzenesulfonamide, m.p. 148°–151°.

EXAMPLE 33

N-Methyl-N-(phenylmethoxy)-2-nitrobenzenesulfonamide

A mixture of 110.6 g of the product of Example 32, 49.8 g of anhydrous potassium carbonate, 55.8 g of methyliodide and 500 ml of acetone was stirred at ambient temperature for 20 hours. The solvent was evaporated and the residue partitioned between methylene chloride and water. Concentration of the organic extract afforded 88.9 g of N-methyl-N-(phenylmethoxy)-2-nitrobenzenesulfonamide as a yellow oil. [NMR:$\delta$ 2.8(s, 3H, NCH$_3$)].

EXAMPLE 34

N-Methyl-N-(phenylmethoxy)-2-aminobenzenesulfonamide

To a solution of 88.9 g of the product of Example 33 in 565 ml of 90% aqueous acetic acid was added 83 g of iron powder at 80°–90° in several portions. Water (60 ml) was then added and heating continued for 20 minutes. Charcoal (10 g) was added and the solution filtered through Celite ® and concentrated in-vacuo. The residue was made strongly alkaline with 20% NaOH solution, then extracted with methylene chloride. The extract was dried and concentrated in-vacuo to give 29.3 g of N-methyl-N-(phenylmethoxy)-2-aminobenzenesulfonamide as a yellow oil. [NMR:δ5.1(broad singlet, 2H, NH₂)].

EXAMPLE 35

N-Methyl-N-(phenylmethoxy)-1,2-benzenedisulfonamide

Using a procedure analogous to that described in Example 10, 28.8 g of the product of Example 34 was converted to 19.3 g of N-methyl-N-(phenylmethoxy)-1,2-benzenedisulfonamide, m.p. 122°–128°. [NMR:δ 5.7(broad singlet, 2H, SO$_2$NH$_2$)].

EXAMPLE 36

N'-[Butylaminocarbonyl]-N-methyl-N-(phenylmethoxy)-1,2-benzenedisulfonamide

Using a procedure analogous to that described in Example 11, 18.8 g of the product of Example 35 was converted to 19.1 g of N-(butylaminocarbonyl)-N-methyl-N-(phenylmethoxy)-1,2-benzenedisulfonamide, obtained as a brown syrup.

EXAMPLE 37

N'-[(4,6-Dimethylpyrimidin-2-yl)aminocarbonyl]-N-methyl-N-(phenylmethoxy)1,2-benzenedisulfonamide Using a procedure analogous to those described in Examples 12 and 13, 18.6 g of the product of Example 36 was converted to 7.4 g of N'-[(4,6-dimethylpyrimidin-2-yl)aminocarbonyl]-N-methyl-N-(phenylmethoxy)-1,2-benzenedisulfonamide, m.p. 186°–192°.

NMR(DMSO-d$_6$)δ: 2.4(s, 6H, Het-CH$_3$'s); 2.8(s, 3H, CH$_3$N); 4.7(s, 2H, CH$_2$O); 7.1(s, 1H, Het-H); 7.3(s, 5H, 5 aromatics); 7.8–9.0(m, 4H, 4 aromatics); 10.4(broad S, 1H, NH); 13.7(broad S, 1H, NH).

EXAMPLE 38

N'-[(4,6-Dimethylpyrimidin-2-yl)aminocarbonyl]-N-methyl-1,2-benzenedisulfonamide To a suspension of 0.5 g of the product of Example 37 in 10 ml of dry xylenes was added 0.5 ml of borontribromide dropwise. The resultant thick suspension was warmed to 60° for 1 hour. The reaction mixture was cooled to room temperature, quenched with water and triturated with hexanes. The resultant suspension was filtered and air dried to give 0.3 g of N'-[(4,6-dimethypyrimidin-2-yl)aminocarbonyl]-N-methyl-1,2-benzenedisulfonamide, m.p. 180°–185°. The NMR showed the complete loss of the phenylemthoxy group.

IR(Nujol) 1715 cm⁻¹ (C=O), 1360 cm⁻¹ (SO$_2$).

Mass Spect.

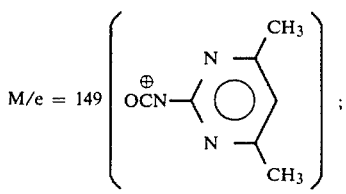

M/e = 149

-continued
Mass Spect.

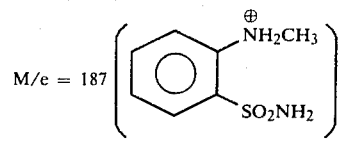

M/e = 187

EXAMPLE 39

N'-[(4,6-Dimethoxy-1,3,5-triazin-2-yl)thioxomethylamino]-N,N-diethyl-1,2-benzenedisulfonamide A mixture of 4.0 g of N,N-diethyl-1,2-benzenedisulfonamide, 2.7 g of anhydrous potassium carbonate, 5.8 g of 4,6-dimethoxy-1,3,5-triazin-2-isothiocyanate, and 60 ml of dry acetone was stirred at ambient temperature for 18 hours. A precipitate was filtered off, washed with acetone, then suspended in 350 ml of water and brought to pH=1 with 1 N HCl solution. The precipitate was filtered, washed with water and dried 3 hours at 60° in-vacuo to give 3.0 g of N'[(4,6-dimethoxy-1,3,5-triazin-2-yl)thioxomethylamino]-N,N-diethyl-1,2-benzenedisulfonamide, m.p. 154°–156° (d).

NMR(DMSO-d$_6$)δ: 0.9–1.2[5, 5.7H, (CH$_3$CH$_2$)$_2$N-]; 3.1–3.5[qt. 4.5H, (CH$_3$CH$_2$)$_2$N-]; 3.8(s, 5.9H, Het-OCH$_3$'s); 7.5–8.7(m, 4.0H, 4 aromatics); 9.1(s, 0.9H, NH).

EXAMPLE 40

Methyl N'-[2-(diethylaminosulfonyl)phenylsulfonyl]-N-(4,6-dimethoxy-1,3,5-triazin-2-yl)carbamimidothioate A mixture of 2.0 g of the product of Example 39, 25 ml of tetrahydrofuran and 1.5 ml of 3 M sodium methoxide in methanol solution was refluxed for 10 minutes. A solution of 0.8 g of methyl iodide in 10 ml of tetrahydrofuran was added and the mixture refluxed for another 2 hours. The solution was cooled to 20°, fitered and stripped in-vacuo to give 3 g of viscous oil. The oil was triturated with 25 ml of 1-chlorobutane and filtered again. The filtrate was stripped again to give 1.3 g of oil which slowly crystallized. This solid was triturated with 50:50 cyclohexane/1-chlorobutane and filtered to give 0.5 g of crude product. Recrystallization from acetonitrile gave 0.18 g of methyl N'-[2-(diethylaminosulfonyl)phenysulfonyl)-N-(4,6-dimethoxy-1,3,5-triazin-2-yl)carbamimido]-thioate, m.p. 150°–156°.

| Anal. Calcd. for C$_{17}$H$_{24}$N$_6$O$_6$S$_3$: | C, 40.47; | | |
|---|---|---|---|
| H, | 4.79; | N, | 16.65 |
| | | Found: | C, 40.8; |
| H, | 4.81; | N, | 17.4. | 41.0 |
| | 4.87 | | 17.5 | |

NMR(DMSO-d$_6$)δ: 1.0–1.3[t, 5.7H (CH$_3$CH$_2$)$_2$N-]; 2.25(s, 3.1H, CH$_3$S); 3.2–3.6[qt, 4.4H, (CH$_3$CH$_2$)$_2$N-]; 4.0(s, 5.8H, Het-OCH$_3$'s); 7.9–8.7(m, 4.1H, 4aromatics); 10.9(broad s, 1.0H, NH).

Using the methods and examples discussed above, and choosing the appropriate aminoheterocycle and sulfonyl isocyanate or sulfonyl isothiocyanate, the compounds described in Tables I to IV-a can be prepared.

Also, using the methods and examples discussed above, the sulfonylisocyanates and sulfonylisothiocyanates described in Table V can be prepared.

TABLE I

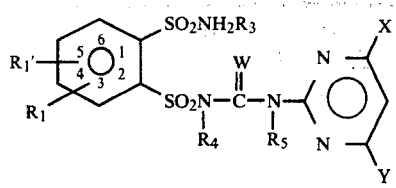

| $R_1'$ | $R_1$ | $R_2$ | $R_3$ | $R_4$ | $R_5$ | W | X | Y | m.p. (°C.) |
|---|---|---|---|---|---|---|---|---|---|
| H | H | $CH_3$ | $CH_3$ | H | H | O | $OCH_3$ | $OCH_3$ | 228–230°(d) |
| H | H | $CH_3$ | $CH_3$ | H | H | O | $OCH_3$ | $CH_3$ | 235–237°(d) |
| H | H | $CH_3$ | $CH_3$ | H | H | O | $CH_3$ | $CH_3$ | 219–222°(d) |
| H | H | $CH_3$ | $CH_3$ | $CH_3$ | H | O | $OCH_3$ | $OCH_3$ | |
| H | H | $CH_3$ | $CH_3$ | H | $CH_3$ | O | $OCH_3$ | $CH_3$ | |
| H | H | $CH_3$ | $CH_3$ | H | H | O | H | H | |
| H | H | $CH_3$ | $CH_3$ | H | H | O | $CH_3CH_2O$ | $CH_3$ | |
| H | H | $CH_3$ | $CH_3$ | H | H | O | $CH_3O$ | $CF_3$ | |
| H | H | $CH_3$ | $CH_3$ | H | H | O | $CH_3$ | $NHCH_3$ | |
| H | H | $CH_3$ | $CH_3$ | H | H | O | $CH_3$ | $N(CH_3)_2$ | |
| H | H | $CH_3$ | $CH_3$ | H | H | O | $CH_3$ | $CF_3CH_2O$ | |
| H | H | $CH_3$ | $CH_3$ | H | H | O | $CH_3$ | $CH_3CH_2O$ | |
| H | H | $CH_3$ | $CH_3$ | H | H | O | $CH_3$ | $SCH_3$ | |
| H | H | $CH_3$ | $CH_3$ | H | H | O | $CH_3$ | $CH_3O(CH_2)_2O$ | |
| H | H | $CH_3$ | $CH_3$ | H | H | O | $CH_3$ | $C_2H_5O(CH_2)_3O$ | |
| H | H | $CH_3$ | $CH_3$ | H | H | O | $CH_3$ | $CH_3O(CH_2)_2-$ | |
| H | H | $CH_3$ | $CH_3$ | H | H | O | $CH_3$ | $CH_3OCH_2-$ | 177–181°(d) |
| H | H | $CH_3$ | $CH_3$ | H | H | O | $CH_3$ | $OCH_2CO_2CH_3$ | |
| H | H | $CH_3$ | $CH_3$ | H | H | O | $CH_3$ | $OCH_2CO_2C_3H_7$ | |
| H | H | $CH_3$ | $CH_3$ | H | H | O | $CH_3$ | $OCHCO_2CH_3$ \| $CH_3$ | 178–183° |
| H | H | $CH_3$ | $CH_3$ | H | H | O | $CH_3O$ | $OCHCO_2C_2H_5$ \| $CH_3$ | |
| H | 4-Br | $CH_3$ | $CH_3$ | H | H | O | $CH_3O$ | $CH_3$ | 197–199°(d) |
| H | 4-Br | $CH_3$ | $CH_3$ | H | H | O | $CH_3$ | $CH_3$ | 212–213°(d) |
| H | H | $CH_3$ | $CH_3$ | H | H | O | $CH_3$ | $OCH_2\overset{O}{\overset{\|}{C}}N(CH_3)_2$ | |
| H | H | $CH_3$ | $CH_3$ | H | H | O | $CH_3$ | $OCHCN(C_3H_7)_2$ \| $CH_3$ (C=O) | |
| H | H | $CH_3$ | $CH_3$ | H | H | O | H | $CH_3$ | |
| H | H | $CH_3$ | $CH_3$ | H | H | O | $CH_3$ | $OCHCO_2i\text{-}C_3H_7$ \| $CH_3$ | |
| H | 4-Cl | $CH_3$ | $CH_3$ | H | H | O | $CH_3$ | $CH_3O$ | 218–221° |
| H | 4-Br | $CH_3$ | $CH_3$ | H | H | O | $CH_3O$ | $CH_3O$ | 200–202° |
| H | 4-F | $CH_3$ | $CH_3$ | H | H | O | $CH_3O$ | $CH_3O$ | 202–204°(d) |
| H | 4-$CH_3$ | $CH_3$ | $CH_3$ | H | H | O | $CH_3$ | $CH_3O$ | 216–218°(d) |
| H | 4-$C_3H_7$ | $CH_3$ | $CH_3$ | H | H | O | $CH_3$ | $CH_3O$ | |
| H | 4-$NO_2$ | $CH_3$ | $CH_3$ | H | H | O | $CH_3O$ | $CH_3O$ | 211–213°(d) |
| H | 4-$CF_3$ | $CH_3$ | $CH_3$ | H | H | O | $CH_3O$ | $CH_3O$ | 194–196° |
| H | 4-$NH_2$ | $CH_3$ | $CH_3$ | H | H | O | $CH_3$ | $CH_3O$ | 185–190°(d) |
| H | 4-$N(CH_3)_2$ | $CH_3$ | $CH_3$ | H | H | O | $CH_3$ | $CH_3O$ | |
| H | 4-CN | $CH_3$ | $CH_3$ | H | H | O | $CH_3O$ | $CH_3O$ | |
| H | 4-$CH_3S-$ | $CH_3$ | $CH_3$ | H | H | O | $CH_3O$ | $CH_3O$ | |
| H | 4-$CH_3\overset{O}{\underset{\|}{\overset{\|}{S}}}-$ | $CH_3$ | $CH_3$ | H | H | O | $CH_3O$ | $CH_3O$ | |
| H | 4-$CH_3\overset{O}{\underset{O}{\overset{\|}{S}}}-$ | $CH_3$ | $CH_3$ | H | H | O | $CH_3O$ | $CH_3O$ | |

TABLE I-continued

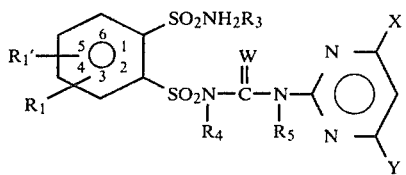

| R1' | R1 | R2 | R3 | R4 | R5 | W | X | Y | m.p. (°C.) |
|---|---|---|---|---|---|---|---|---|---|
| H | 4-CH3O | CH3 | CH3 | H | H | O | CH3O | CH3O | 191.5–192.5° (d) |
| H | 3-Cl | CH3 | CH3 | H | H | O | CH3O | CH3O | |
| H | 5-F | CH3 | CH3 | H | H | O | CH3O | CH3O | |
| H | 6-Cl | CH3 | CH3 | H | H | O | CH3O | CH3O | |
| H | H | C2H5 | C2H5 | H | H | O | CH3O | CH3O | 190–192° |
| H | H | C2H5 | C2H5 | H | H | O | CH3 | CH3O | 170–172° |
| H | H | C2H5 | C2H5 | H | H | O | CH3 | CH3 | 176–179° |
| H | H | C2H5 | C2H5 | H | H | S | CH3O | CH3O | |
| H | H | C2H5 | C2H5 | H | H | S | CH3 | CH3O | |
| H | 4-C2H5O | CH3 | CH3 | H | H | O | CH3O | CH3O | 181–184°(d) |
| H | 4-C2H5O— | CH3 | CH3 | H | H | O | CH3O | CH3 | 205–208°(d) |
| H | 4-C2H5O— | CH3 | CH3 | H | H | O | CH3 | CH3 | 190–193°(d) |
| H | H | n-C3H7 | n-C3H7 | H | H | O | CH3O | CH3O | 163–165° |
| H | H | n-C3H7 | n-C3H7 | H | H | O | CH3O | CH3 | 189–194° |
| H | H | n-C3H7 | CH3 | H | H | O | CH3O | CH3O | glass |
| H | H | n-C3H7 | CH3 | H | H | O | CH3O | CH3 | glass |
| H | H | sec-C4H9 | CH3 | H | H | O | CH3O | CH3O | 203–207° |
| H | H | sec-C4H9 | CH3 | H | H | O | CH3O | CH3 | 188–191° |
| H | H | n-C4H9 | CH3 | H | H | O | CH3O | CH3O | 146–149° |
| H | H | n-C4H9 | CH3 | H | H | O | CH3O | CH3 | 138–142° |
| H | H | i-C3H7 | i-C3H7 | H | H | O | CH3O | CH3O | 187–189° |
| H | H | i-C3H7 | i-C3H7 | H | H | O | CH3O | CH3— | 190–192° |
| H | H | CH2=CHCH2— | CH2=CHCH2— | H | H | O | CH3O | CH3O | |
| H | H | n-C6H13 | CH3 | H | H | O | CH3O | CH3O | |
| H | H | cyclopropyl | CH3 | H | H | O | CH3O | CH3O | |
| H | H | cyclopentyl | CH3 | H | H | O | CH3O | CH3O | |
| H | H | cyclohexyl | H | H | O CH3O | | CH3O | | |
| H | H | cyclohexenyl | CH3 | H | H | O | CH3O | CH3O | |
| H | H | 2-methylcyclohexyl | CH3 | H | H | O | CH3O | CH3O | |
| H | H | NC—C(CH3)2—CH3 | CH3 | H | H | O | CH3O | CH3O | |
| H | H | NCCH2— | NCCH2— | H | H | O | CH3O | CH3O | |
| H | H | NCCH2CH2— | NCCH2CH2— | H | H | O | CH3O | CH3O | |
| H | H | CH3O(CH2)2— | CH3O(CH2)2 | H | H | O | CH3O | CH3O | |
| H | H | CH3OCH—CH2—CH3 | CH3OCH—CH2—CH3 | H | H | O | CH3O | CH3O | |
| H | H | n-C6H13 | n-C4H9 | H | H | O | CH3O | CH3O | |
| H | H | CH3O | CH3 | H | H | O | CH3O | CH3O | 207–211° |

TABLE I-continued

Structure: cyclohexane ring (positions 1-6) with R1' at position 5, R1 at position 4, SO2NH2R3 at position 1, SO2N(R4)-C(W)-N(R5)-pyrimidine with X and Y substituents at position 2.

| R1' | R1 | R2 | R3 | R4 | R5 | W | X | Y | m.p. (°C.) |
|---|---|---|---|---|---|---|---|---|---|
| H | H | —CH2CO2CH3 | —CH2CO2CH3 | H | H | O | CH3O | CH3O | |
| H | H | —CHCO2CH3 \| CH3 | —CHCO2CH3 \| CH3 | H | H | O | CH3O | CH3O | |
| H | H | —CH2CO2—CH(CH3)2 | —CH2CO2—CH(CH3)2 | H | H | O | CH3O | CH3O | |
| H | H | —CH2C(O)N(CH3)2 | —CH2C(O)N(CH3)2 | H | H | O | CH3O | CH3O | |
| H | H | —CH2C(O)N(C3H7)2 | —CH2C(O)N(C3H7)2 | H | H | O | CH3O | CH3O | |
| H | H | —CH(CH3)C(O)N(CH3)2 | —CH(CH3)C(O)N(CH3)2 | H | H | O | CH3O | CH3O | |
| H | H | —CH2CH2CH2CH2— | | H | H | O | CH3O | CH3O | 220–222°(d) |
| H | H | —CH2CH2CH2CH2— | | H | H | O | CH3O | CH3O | 227–229°(d) |
| H | H | —CH2CH2CH2CH2— | | H | H | O | CH3 | CH3 | 213–215°(d) |
| H | 4-Cl | —CH2CH2CH2CH2— | | H | H | O | CH3O | CH3O | |
| H | 4-CF3 | —CH2CH2CH2CH2— | | H | H | O | CH3O | CH3O | |
| H | H | —(CH2)5— | | H | H | O | CH3O | CH3O | 201–204° |
| H | H | —(CH2)6— | | H | H | O | CH3O | CH3O | glass |
| H | H | —(CH2)2—O—(CH2)2— | | H | H | O | CH3O | CH3O | 199–204° |
| H | H | C6H5— | CH3 | H | H | O | CH3O | CH3 | 183–186° |
| H | H | Cl-C6H4— | CH3 | H | H | O | CH3O | CH3 | |
| H | H | CH3-C6H4— | CH3 | H | H | O | CH3O | CH3 | |
| H | H | Br-C6H4— | CH3 | H | H | O | CH3O | CH3 | |
| H | H | F-C6H4— | CH3 | H | H | O | CH3O | CH3 | |
| H | H | C6H5-CH2— | CH3 | H | H | O | CH3O | CH3 | 179–183°(d) |
| H | H | C6H5-CH(CH3)— | CH3 | H | H | O | CH3O | CH3 | |
| H | H | Cl-C6H4-CH2— | —CH3 | H | H | O | CH3O | CH3 | |
| H | H | CH3-C6H4-CH2— | —CH3 | H | H | O | CH3O | CH3 | |
| H | H | Cl-C6H4-CH(CH3)— | —CH3 | H | H | O | CH3O | CH3 | |
| H | H | F-C6H4-CH2— | CH3 | H | H | O | CH3O | CH3 | |
| H | H | Br-C6H4-CH(CH3)— | CH3 | H | H | O | CH3O | CH3 | |

TABLE I-continued

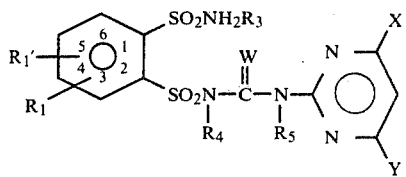

| $R_1'$ | $R_1$ | $R_2$ | $R_3$ | $R_4$ | $R_5$ | W | X | Y | m.p. (°C.) |
|---|---|---|---|---|---|---|---|---|---|
| H | 4-CF$_3$ | CH$_3$ | CH$_3$ | H | H | O | CH$_3$O | CH$_3$ | 182–185°(d) |
| H | 4-CF$_3$ | CH$_3$ | CH$_3$ | H | H | O | CH$_3$ | CH$_3$ | 190–192°(d) |
| H | 4-Cl | CH$_3$ | CH$_3$ | H | H | O | CH$_3$O | CH$_3$O | 200–205° |
| H | 4-Cl | CH$_3$ | CH$_3$ | H | H | O | CH$_3$ | CH$_3$ | 223–226° |
| H | 4-Cl | C$_2$H$_5$ | C$_2$H$_5$ | H | H | O | CH$_3$O | CH$_3$O | 187–190° |
| H | 4-Cl | C$_2$H$_5$ | C$_2$H$_5$ | H | H | O | CH$_3$O | CH$_3$ | 179–181° |
| H | 4-CH$_3$O | CH$_3$ | CH$_3$ | H | H | O | CH$_3$O | CH$_3$ | 205–207°(d) |
| H | 4-CH$_3$O | CH$_3$ | CH$_3$ | H | H | O | CH$_3$ | CH$_3$ | 206–207°(d) |
| 5-Cl | 4-Cl | CH$_3$ | CH$_3$ | H | H | O | CH$_3$O | CH$_3$O | |
| 5-F | 4-Cl | CH$_3$ | CH$_3$ | H | H | O | CH$_3$O | CH$_3$O | |
| 5-Br | 4-Cl | CH$_3$ | CH$_3$ | H | H | O | CH$_3$O | CH$_3$O | |
| 5-CH$_3$ | 4-CH$_3$ | CH$_3$ | CH$_3$ | H | H | O | CH$_3$O | CH$_3$O | |
| 5-CH$_3$O | 4-CH$_3$O | CH$_3$ | CH$_3$ | H | H | O | CH$_3$O | CH$_3$O | |
| 6-Cl | 4-Cl | CH$_3$ | CH$_3$ | H | H | O | CH$_3$O | CH$_3$O | |
| 4-Cl | 3-Cl | CH$_3$ | CH$_3$ | H | H | O | CH$_3$O | CH$_3$O | |
| H | 4-F | CH$_3$ | CH$_3$ | H | H | O | CH$_3$O | CH$_3$ | 222–224°(d) |
| H | 4-F | CH$_3$ | CH$_3$ | H | H | O | CH$_3$ | CH$_3$ | 218–219°(d) |
| H | 4-CH$_3$ | CH$_3$ | CH$_3$ | H | H | O | CH$_3$O | CH$_3$O | 208–210°(d) |
| H | 4-CH$_3$ | CH$_3$ | CH$_3$ | H | H | O | CH$_3$ | CH$_3$ | 202–215°(d) |
| H | 4-NO$_2$ | CH$_3$ | CH$_3$ | H | H | O | CH$_3$O | CH$_3$ | 207–209°(d) |
| H | 4-NO$_2$ | CH$_3$ | CH$_3$ | H | H | O | CH$_3$ | CH$_3$ | 212–215°(d) |
| H | 4-NH$_2$ | CH$_3$ | CH$_3$ | H | H | O | CH$_3$O | CH$_3$ | |
| H | 4-NH$_2$ | CH$_3$ | CH$_3$ | H | H | O | CH$_3$ | CH$_3$ | |
| H | 4-N(CH$_3$)$_2$ | CH$_3$ | CH$_3$ | H | H | O | CH$_3$O | CH$_3$ | |
| H | 4-N(CH$_3$)$_2$ | CH$_3$ | CH$_3$ | H | H | O | CH$_3$ | CH$_3$ | |
| H | 4-CN | CH$_3$ | CH$_3$ | H | H | O | CH$_3$O | CH$_3$ | |
| H | 4-CN | CH$_3$ | CH$_3$ | H | H | O | CH$_3$ | CH$_3$ | |
| H | 4-CH$_3$S— | CH$_3$ | CH$_3$ | H | H | O | CH$_3$O | CH$_3$ | |
| H | 4-CH$_3$S— | CH$_3$ | CH$_3$ | H | H | O | CH$_3$ | CH$_3$ | |
| H | CH$_3$SO$_2$— | CH$_3$ | CH$_3$ | H | H | O | CH$_3$O | CH$_3$ | |
| H | 4-CH$_3$SO$_2$— | CH$_3$ | CH$_3$ | H | H | O | CH$_3$ | CH$_3$ | |
| H | 4-N=C=O | CH$_3$ | CH$_3$ | H | H | O | CH$_3$O | CH$_3$O | |
| H | 4-NHCCH$_3$<br>‖<br>O | CH$_3$ | CH$_3$ | H | H | O | CH$_3$O | CH$_3$O | |
| H | 4-NHCCH(CH$_3$)$_2$<br>‖<br>O | CH$_3$ | CH$_3$ | H | H | O | CH$_3$O | CH$_3$O | |
| H | 4-NHCNHCH$_3$<br>‖<br>O | CH$_3$ | CH$_3$ | H | H | O | CH$_3$O | CH$_3$O | |
| H | 4-NHCNHCH(CH$_3$)$_2$<br>‖<br>O | CH$_3$ | CH$_3$ | H | H | O | CH$_3$O | CH$_3$O | |
| H | H | CH$_3$ | CH$_3$ | H | H | O | CH$_3$ | —OCHCO$_2$H<br>\|<br>CH$_3$ | |
| H | H | CH$_3$ | CH$_3$ | H | H | O | CH$_3$ | —CO$_2$CH$_3$ | |
| H | H | CH$_3$ | CH$_3$ | H | H | O | CH$_3$ | CO$_2$H | |
| H | H | CH$_3$ | CH$_3$ | H | H | O | CH$_3$ | CO$_2$—⟨ | |
| H | H | CH$_3$ | CH$_3$ | H | H | O | CH$_3$ | CH$_2$CO$_2$CH$_3$ | |
| H | H | CH$_3$ | CH$_3$ | H | H | O | CH$_3$ | CH$_2$CO$_2$—⟨ | |

TABLE I-continued

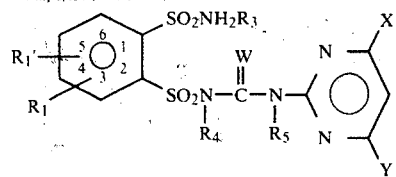

| R1' | R1 | R2 | R3 | R4 | R5 | W | X | Y | m.p. (°C.) |
|---|---|---|---|---|---|---|---|---|---|
| H | H | CH3 | CH3 | H | H | O | CH3 | CH2CO2H | |
| H | H | CH3O | CH3 | H | H | O | CH3O | CH3 | 220–223° |
| H | H | CH3O | CH3 | H | H | O | CH3 | CH3 | 220–222° |
| H | H | CH3CH2 | CH3 | H | H | O | CH3O | CH3O | 204–206° |
| H | H | CH3CH2 | CH3 | H | H | O | CH3O | CH3 | 200–202° |
| H | H | CH3CH2 | CH3 | H | H | O | CH3 | CH3 | 192–194° |
| H | H | n-C3H7 | CH3 | H | H | O | CH3 | CH3 | 173–176° |
| H | H | n-C3H7 | CH3 | H | H | O | CH3O | CH3O | 202–205° |
| H | H | i-C3H7 | CH3 | H | H | O | CH3O | CH3 | 192–200° |
| H | H | i-C3H7 | CH3 | H | H | O | CH3 | CH3 | 193–196° |
| H | H | n-C4H9 | CH3 | H | H | O | CH3 | CH3 | 173–176° |
| H | H | sec-C4H9 | CH3 | H | H | O | CH3 | CH3 | 184–188° |
| H | H | C6H5 | CH3 | H | H | O | CH3O | CH3O | 158–180° |
| H | H | C6H5 | CH3 | H | H | O | CH3 | CH3 | 184–185° |
| H | H | C6H5CH2– | CH3 | H | H | O | CH3O | CH3O | 178–181°(d) |
| H | H | C6H5CH2– | CH3 | H | H | O | CH3 | CH3 | 188–190°(d) |
| H | H | i-C3H7 | C2H5 | H | H | O | CH3O | CH3O | 207–209° |
| H | H | i-C3H7 | C2H5 | H | H | O | CH3O | CH3 | 171–174° |
| H | H | i-C3H7 | C2H5 | H | H | O | CH3 | CH3 | 168–171° |
| H | H | i-C3H7 | i-C3H7 | H | H | O | CH3 | CH3 | 208–211° |
| H | H | —(CH2)5— | | H | H | O | CH3O | CH3 | 209–211° |
| H | H | —(CH2)5— | | H | H | O | CH3 | CH3 | 179–182° |
| H | H | —CH2CH2OCH2CH2— | | H | H | O | CH3O | CH3 | 218–223° |
| H | H | —CH2CH2OCH2CH2— | | H | H | O | CH3 | CH3 | 209–211° |
| H | H | —(CH2)6— | | H | H | O | CH3O | CH3 | 169–171° |
| H | H | —(CH2)6— | | H | H | O | CH3 | CH3 | 190–192° |
| H | H | n-C3H7 | n-C3H7 | H | H | O | CH3 | CH3 | 180–184° |
| H | 4-COCH3 | CH3 | CH3 | H | H | O | CH3 | CH3 | |
| H | 4-CO—i-C3H7 | CH3 | CH3 | H | H | O | CH3 | CH3 | |
| H | 4-CH2OCH3 | CH3 | CH3 | H | H | O | CH3 | CH3 | |
| H | 4-CH2O—i-C3H7 | CH3 | CH3 | H | H | O | CH3 | CH3 | |
| H | 4-CH2SCH3 | CH3 | CH3 | H | H | O | CH3 | CH3 | |
| H | 4-CH2SO2CH3 | CH3 | CH3 | H | H | O | CH3 | CH3 | |
| H | 4-CH3SCH3 (=O) | CH3 | CH3 | H | H | O | CH3 | CH3 | |

TABLE I-continued

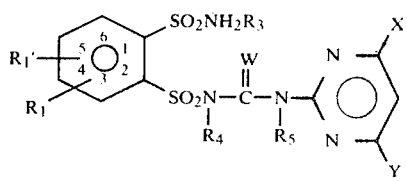

| R$_1'$ | R$_1$ | R$_2$ | R$_3$ | R$_4$ | R$_5$ | W | X | Y | m.p. (°C.) |
|---|---|---|---|---|---|---|---|---|---|
| H | H | —CH$_2$—◁ | CH$_3$ | H | H | O | CH$_3$O | CH$_3$O | |
| H | H | —CH$_2$—⬡S | CH$_3$ | H | H | O | CH$_3$O | CH$_3$O | |
| H | H | CH$_3$ | CH$_3$ | H | H | O | CH$_3$O | —CH$_2$CH$_3$ | |
| H | H | CH$_3$ | CH$_3$ | H | H | O | CH$_3$O | —CH$_2$CH$_2$CH$_3$ | |
| H | H | CH$_3$ | CH$_3$ | H | H | O | CH$_3$O | —CH(CH$_3$)$_2$ | |
| H | H | H | CH$_3$ | H | H | O | CH$_3$O | CH$_3$ | |
| H | H | H | C$_2$H$_5$ | H | H | O | CH$_3$O | CH$_3$ | |
| H | H | H | n-C$_3$H$_7$ | H | H | O | CH$_3$O | CH$_3$ | |
| H | H | H | i-C$_3$H$_7$ | H | H | O | CH$_3$O | CH$_3$ | |
| H | H | H | n-C$_4$H$_9$ | H | H | O | CH$_3$O | CH$_3$ | |
| H | H | H | t-C$_4$H$_9$ | H | H | O | CH$_3$O | CH$_3$ | |
| H | H | H | sec-C$_4$H$_9$ | H | H | O | CH$_3$O | CH$_3$ | |
| H | H | H | CH$_2$=CHCH$_2$— | H | H | O | CH$_3$O | CH$_3$ | |
| H | H | H | —CH$_2$CO$_2$CH$_3$ | H | H | O | CH$_3$O | CH$_3$ | |
| H | H | H | -n-C$_6$H$_{13}$ | H | H | O | CH$_3$O | CH$_3$ | |
| H | H | CH$_3$— | ⬡—CH$_2$O— | H | H | O | CH$_3$O | CH$_3$ | |
| H | H | ⬡—CHO—CH$_3$ | CH$_3$ | H | H | O | CH$_3$O | CH$_3$ | |
| H | H | ⬡(Cl)—CH$_2$O— | CH$_3$ | H | H | O | CH$_3$O | CH$_3$ | |
| H | H | ⬡(CH$_3$)—CH$_2$O— | CH$_3$ | H | H | O | CH$_3$O | CH$_3$ | |
| H | H | CF$_3$CH$_2$— | CF$_3$CH$_2$— | H | H | O | CH$_3$O | CH$_3$ | |
| H | H | —CH$_2$C≡CH | CH$_3$ | H | H | O | CH$_3$O | CH$_3$O | |
| H | H | —C(CH$_3$)$_2$—C≡CH | CH$_3$ | H | H | O | CH$_3$O | CH$_3$O | |
| H | H | CH$_3$— | CF$_3$CHFCF$_2$— | H | H | O | CH$_3$O | CH$_3$ | |
| H | H | CH$_3$— | HBrFCCF$_2$— | H | H | O | CH$_3$O | CH$_3$ | |
| H | H | CH$_3$— | HClFCCF$_2$— | H | H | O | CH$_3$O | CH$_3$ | |
| H | H | CH$_3$— | HCF$_2$CF$_2$— | H | H | O | CH$_3$O | CH$_3$ | 176–177°(d) |
| H | H | CH$_3$— | HCF$_2$CF$_2$— | H | H | O | CH$_3$O | CH$_3$O | 179–181°(d) |
| H | H | CH$_3$— | HCF$_2$CF$_2$— | H | H | O | CH$_3$ | CH$_3$ | 171–181°(d) |
| H | 4-NHCOCH$_3$ | CH$_3$ | CH$_3$ | H | H | O | CH$_3$O | CH$_3$ | |
| H | 4-NHCO—i-C$_3$H$_7$ | CH$_3$ | CH$_3$ | H | H | O | CH$_3$O | CH$_3$ | |
| H | H | CH$_3$ | CH$_3$ | H | H | O | CH$_3$O | —CH$_2$CN | |
| H | H | CH$_3$ | CH$_3$ | H | H | O | CH$_3$O | —CH$_2$CH$_2$CN | |
| H | H | CH$_3$ | CH$_3$ | H | H | O | CH$_3$O | —CH$_2$Cl | |
| H | H | CH$_3$ | CH$_3$ | H | H | O | CH$_3$O | —N$_3$ | |
| H | H | CH$_3$ | CH$_3$ | H | H | O | CH$_3$O | —OCH$_2$CH=CH$_2$ | |
| H | H | CH$_3$ | CH$_3$ | H | H | O | CH$_3$O | —OCH$_2$C≡CH | |
| H | H | CH$_3$ | CH$_3$ | H | H | O | CH$_3$O | —N(CH$_3$)—CH$_2$CN | |

TABLE I-a

| A | R1' | R1 | R4 | R5 | W | X | Y | m.p.(°C.) |
|---|---|---|---|---|---|---|---|---|
| CF₃CH₂O— | H | H | H | H | O | CH₃O | CH₃O | 203–205° |
| CF₃CH₂O— | H | H | H | H | O | CH₃O | CH₃ | 191–192°(d) |
| CF₃CH₂O— | H | H | H | H | O | CH₃ | CH₃ | 187–188.5°(d) |
|  | H | H | H | H | O | CH₃O | CH₃O | 219–222°(d) |
|  | H | H | H | H | O | CH₃O | CH₃ | 210–215°(d) |
|  | H | H | H | H | O | CH₃ | CH₃ | 192–194°(d) |
| CCl₃CH₂O— | H | H | H | H | O | CH₃O | CH₃O | |
| CCl₃CH₂O— | H | H | H | H | O | CH₃O | CH₃ | |
| CCl₃CH₂O— | H | H | H | H | O | CH₃ | CH₃ | |
| CBr₃CH₂O— | H | H | H | H | O | CH₃O | CH₃O | |
| HCF₂CH₂O—CH₃O | H | H | H | H | O | CH₃O | | |
| HCF₂CF₂CH₂O— | H | H | H | H | O | CH₃O | CH₃O | |
| CF₃CF₃CH₂O— | H | H | H | H | O | CH₃O | CH₃O | |
| CF₃(CF₂)₂CH₂O— | H | H | H | H | O | CH₃O | CH₃O | |
| CF₃CHO—\|CH₃ | H | H | H | H | O | CH₃O | CH₃O | |
| (CF₃)₂CHO— | H | H | H | H | O | CH₃O | CH₃O | |
| (CF₃)₂CHO— | H | H | H | H | O | CH₃O | CH₃ | |
| (CF₃)₂CHO— | H | H | H | H | O | CH₃ | CH₃ | |
|  | H | H | H | H | O | CH₃O | CH₃O | |
|  | H | H | H | H | O | CH₃O | CH₃O | |
|  | H | H | H | H | O | CH₃O | CH₃O | |
| 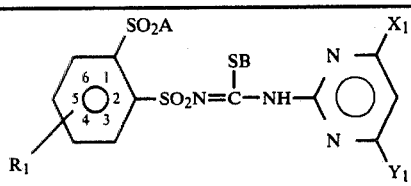 | H | H | H | H | O | CH₃O | CH₃O | |
| CF₃CH₂O | H | 4-Cl | H | H | O | CH₃O | CH₃O | |
| CF₃CH₂O | H | 4-CF₃ | H | H | O | CH₃O | CH₃O | |
| CF₃CH₂O | H | 4-CH₃O | H | H | O | CH₃O | CH₃O | |
| CF₃CH₂O | H | 4-NO₂ | H | H | O | CH₃O | CH₃O | |
| CF₃CH₂O | H | 4-CN | H | H | O | CH₃O | CH₃O | |
| CF₃CH₂O | H | 4-F | H | H | O | CH₃O | CH₃O | |
| CF₃CH₂O | H | 4-CN | H | H | O | CH₃O | CH₃O | |

TABLE I-b

| R₁ | A | B | X₁ | Y₁ | m.p.(°C.) |
|---|---|---|---|---|---|
| H | —N(CH₃)₂ | CH₃— | CH₃— | CH₃O | |
| H | —N(CH₃)₂ | i-C₃H₇— | CH₃— | CH₃O | |
| H | —N(CH₃)₂ | n-C₆H₁₃— | CH₃— | CH₃O | |
| H | —N(CH₃)₂ | CH₃OCH₂CH₂— | CH₃— | CH₃O | |
| H | —N(CH₃)₂ | C₂H₅OCH₂CH₂— | CH₃— | CH₃O | |
| H | —N(CH₃)₂ | CH₃O(CH₂)₃— | CH₃— | CH₃O | |
| H | —N(CH₃)₂ | CH₃O₂CCH₂— | CH₃— | CH₃O | |
| H | —N(CH₃)₂ | i-C₃H₇O₂CCH₂— | CH₃— | CH₃O | |
| H | —N(CH₃)₂ | CH₃NC(O)CH₂—\|OCH₃ | CH₃— | CH₃O | |

TABLE I-b-continued $$\text{structure: benzene ring with SO}_2\text{A at position 1, SO}_2\text{N(SB)=C-NH-pyrimidine (with X}_1\text{, Y}_1\text{) at position 2, R}_1\text{ at position 4}$$

| R₁ | A | B | X₁ | Y₁ | m.p.(°C.) |
|---|---|---|---|---|---|
| H | $-N(CH_3)_2$ | $(CH_3)_2NC(O)CH_2-$ | $CH_3-$ | $CH_3O$ | |
| H | $-N(CH_3)_2$ | $(CH_3CH_2CH_2)_2NC(O)CH_2-$ | $CH_3-$ | $CH_3O$ | |
| H | $-N(CH_3)_2$ | $H_2NC(O)CH_2-$ | $CH_3-$ | $CH_3O$ | |
| H | $-N(CH_3)_2$ | $C_6H_5-CH_2-$ | $CH_3-$ | $CH_3O$ | |
| H | $-N(CH_3)_2$ | 2-Cl-$C_6H_4-CH_2-$ | $CH_3-$ | $CH_3O$ | |
| H | $-N(CH_3)_2$ | $NCCH_2-$ | $CH_3-$ | $CH_3O$ | |
| H | $-N(CH_3)_2$ | $H_3C=CHCH_2-$ | $CH_3-$ | $CH_3O$ | |
| H | $-(CH_3)_2$ | $HC\equiv CCH_2-$ | $CH_3-$ | $CH_3O$ | |
| H | $-N(CH_3)_2$ | $CH_3OCH_2-$ | $CH_3-$ | $CH_3O$ | |
| H | $-N(CH_3)_2$ | $CH_3(CH_2)_3OCH_2-$ | $CH_3-$ | $CH_3O$ | |
| H | $-N(CH_3)_2$ | $CH_3O(CH_2)_2OCH_2-$ | $CH_3-$ | $CH_3O$ | |
| H | $-N(CH_3)_2$ | $C_2H_5O(CH_2)_2OCH_2-$ | $CH_3-$ | $CH_3O$ | |
| H | $-N(C_2H_5)_2$ | $CH_3$ | $CH_3O$ | $CH_3O$ | |
| H | $-N(CH_3)(C_2H_5)$ | $CH_3$ | $CH_3O$ | $CH_3$ | |
| H | $-N(CH_3)(i-C_3H_7)$ | $CH_3$ | $CH_3O$ | $CH_3$ | |
| H | $-N(CH_3)(n-C_6H_{13})$ | $CH_3$ | $CH_3O$ | $CH_3$ | |
| H | $-N(CH_3)(CH_2C_6H_5)$ | $CH_3$ | $CH_3O$ | $CH_3$ | |
| H | $-N(CH_3)(OCH_2C_6H_5)$ | $CH_3$ | $CH_3O$ | $CH_3$ | |
| H | $-NHCH_3$ | $CH_3$ | $CH_3O$ | $CH_3$ | |
| H | $-NHC_2H_5$ | $CH_3$ | $CH_3O$ | $CH_3$ | |
| H | $-NHC_6H_{13}$ | $CH_3$ | $CH_3O$ | $CH_3$ | |
| H | $-N(CH_3)(CF_2CF_2H)$ | $CH_3$ | $CH_3O$ | $CH_3$ | |
| H | $-OCH_2CF_3$ | $CH_3$ | $CH_3O$ | $CH_3$ | |
| H | -N-pyrrolidinyl | $CH_3$ | $CH_3O$ | $CH_3$ | |
| H | $-N(CH_3)(CH_2CN)$ | $CH_3$ | $CH_3O$ | $CH_3$ | |
| H | $-N(CH_2CN)_2$ | $CH_3$ | $CH_3O$ | $CH_3$ | |
| 4-Cl | $-N(CH_3)_2$ | $CH_3$ | $CH_3O$ | $CH_3$ | |
| 4-$CF_3$ | $-N(CH_3)_2$ | $CH_3$ | $CH_3O$ | $CH_3$ | |
| 4-$NO_2$ | $-N(CH_3)_2$ | $CH_3$ | $CH_3O$ | $CH_3$ | |
| 4-$CH_3O$ | $-N(CH_3)_2$ | $CH_3$ | $CH_3O$ | $CH_3$ | |
| 4-F | $-N(CH_3)_2$ | $CH_3$ | $CH_3O$ | $CH_3$ | |
| 4-Br | $-N(CH_3)_2$ | $CH_3$ | $CH_3O$ | $CH_3$ | |
| 4-$CH_3$ | $-N(CH_2)_2$ | $CH_3$ | $CH_3O$ | $CH_3$ | |
| 4-CN | $-N(CH_3)_2$ | $CH_3$ | $CH_3O$ | $CH_3$ | |
| 4-$N(CH_3)_2$ | $-N(CH_3)_2$ | $CH_3$ | $CH_3O$ | $CH_3$ | |
| 4-$SCH_3$ | $-N(CH_3)_2$ | $CH_3$ | $CH_3O$ | $CH_3$ | |
| 4-$SO_2CH_3$ | $-N(CH_3)_2$ | $CH_3$ | $CH_3O$ | $CH_3$ | |
| 4-$NH_2$ | $-N(CH_3)_2$ | $CH_3$ | $CH_3O$ | $CH_3$ | |
| 4-NHC(O)$CH_3$ | $-N(CH_3)_2$ | $CH_3$ | $CH_3O$ | $CH_3$ | |
| 4-NHC(O)NHCH$_3$ | $-N(CH_3)_2$ | $CH_3$ | $CH_3O$ | $CH_3$ | |

TABLE I-b-continued

Structure: benzene ring with SO₂A at position 1, SO₂N=C(SB)-NH- linked to pyrimidine with X₁ and Y₁ substituents, R₁ on benzene ring.

| R₁ | A | B | X₁ | Y₁ | m.p.(°C.) |
|---|---|---|---|---|---|
| 4-NHCOCH₃ | —N(CH₃)₂ | CH₃ | CH₃O | CH₃ | |
| H | —N(CH₃)₂ | CH₃ | CH₃O | CH₃O | |
| H | —N(CH₃)₂ | CH₃ | CH₃ | CH₃ | |
| H | —N(CH₃)₂ | CH₃ | H | CH₃ | |
| H | —N(CH₃)₂ | CH₃ | H | CH₃O | |
| H | —N(CH₃)₂ | CH₃ | H | C₂H₅O | |
| H | —N(CH₃)₂ | CH₃ | CH₃ | C₂H₅O | |
| H | —N(CH₃)₂ | CH₃ | CH₃O | C₂H₅O | |
| H | —N(CH₃)₂ | CH₃HNCOCH₂— | CH₃— | CH₃O | |
| H | —N(CH₃)₂ | CH₃CH₂HNCOCH₂— | CH₃— | CH₃O | |
| H | —N(CH₃)₂ | (CH₃)₂CHNHCOCH₂— | CH₃— | CH₃O | |

TABLE II

Structure: benzene ring with SO₂NR₂R₃ at position 1, SO₂N(R₄)-C(W)-N(R₅)-(pyrimidine with X, Y), R₁ and R₁' on benzene ring.

| R₁' | R₁ | R₂ | R₃ | R₄ | R₅ | W | X | Y | m.p.(°C.) |
|---|---|---|---|---|---|---|---|---|---|
| H | H | CH₃ | CH₃ | H | H | O | OCH₃ | OCH₃ | 200–203°(d) |
| H | H | CH₃ | CH₃ | H | H | O | OCH₃ | CH₃ | 194–196°(d) |
| H | H | CH₃ | CH₃ | H | H | O | CH₃ | CH₃ | 210–212°(d) |
| H | H | CH₃ | CH₃ | CH₃ | H | O | OCH₃ | OCH₃ | |
| H | H | CH₃ | CH₃ | H | CH₃ | O | OCH₃ | OCH₃ | 167–170°(d) |
| H | H | CH₃ | CH₃ | H | H | O | H | H | |
| H | H | CH₃ | CH₃ | H | H | O | CH₃CH₂O | CH₃ | |
| H | H | CH₃ | CH₃ | H | H | O | CH₃O | CF₃ | |
| H | H | CH₃ | CH₃ | H | H | O | CH₃ | NHCH₃ | |
| H | H | CH₃ | CH₃ | H | H | O | CH₃ | N(CH₃)₂ | |
| H | H | CH₃ | CH₃ | H | H | O | CH₃ | CF₃CH₂O | glass |
| H | H | CH₃ | CH₃ | H | H | O | CH₃O | CH₃CH₂O | 163–167° |
| H | H | CH₃ | CH₃ | H | H | O | CH₃ | SCH₃ | |
| H | H | CH₃ | CH₃ | H | H | O | CH₃ | CH₃O(CH₂)₂O | |
| H | H | CH₃ | CH₃ | H | H | O | CH₃ | C₂H₅O(CH₂)₃O | |
| H | H | CH₃ | CH₃ | H | H | O | CH₃ | CH₃O(CH₂)₂— | |
| H | H | CH₃ | CH₃ | H | H | O | CH₃ | CH₃OCH₂— | |
| H | H | CH₃ | CH₃ | H | H | O | CH₃ | OCH₂CO₂CH₃ | 179–186°(d) |
| H | H | CH₃ | CH₃ | H | H | O | CH₃ | OCH₂CO₂C₃H₇ | |
| H | H | CH₃ | CH₃ | H | H | O | CH₃ | OCH(CH₃)CO₂CH₃ | |
| H | H | CH₃ | CH₃ | H | H | O | CH₃O | OCH(CH₃)CO₂C₂H₅ | |
| H | 4-Br | CH₃ | CH₃ | H | H | O | CH₃O | CH₃ | 193–195°(d) |
| H | 4-Br | CH₃ | CH₃ | H | H | O | CH₃ | CH₃ | 213–214°(d) |
| H | H | CH₃ | CH₃ | H | H | O | CH₃ | OCH₂CON(CH₃)₂ | |
| H | H | CH₃ | CH₃ | H | H | O | CH₃ | OCH(CH₃)CON(C₃H₇)₂ | |
| H | H | CH₃ | CH₃ | H | H | O | H | CH₃ | |
| H | H | CH₃ | CH₃ | H | H | O | CH₃ | OCH(CH₃)CO₂i-C₃H₇ | |
| H | 4-Cl | CH₃ | CH₃ | H | H | O | CH₃ | CH₃O | 193–198° |

TABLE II-continued

[Structure: cyclohexane ring with positions labeled 1-6, bearing R$_1$' at position 5, R$_1$ at position 4, SO$_2$NR$_2$R$_3$ at position 1, and SO$_2$N(R$_4$)–C(=W)–N(R$_5$)– linked to a pyrimidine ring with X and Y substituents]

| R$_1$' | R$_1$ | R$_2$ | R$_3$ | R$_4$ | R$_5$ | W | X | Y | m.p.(°C.) |
|---|---|---|---|---|---|---|---|---|---|
| H | 4-Br | CH$_3$ | CH$_3$ | H | H | O | CH$_3$O | CH$_3$O | 199.5–200°(d) |
| H | 4-F | CH$_3$ | CH$_3$ | H | H | O | CH$_3$O | CH$_3$O | 169–175°(d) |
| H | 4-CH$_3$ | CH$_3$ | CH$_3$ | H | H | O | CH$_3$ | CH$_3$O | 207–209°(d) |
| H | 4-C$_3$H$_7$ | CH$_3$ | CH$_3$ | H | H | O | CH$_3$ | CH$_3$O | |
| H | 4-NO$_2$ | CH$_3$ | CH$_3$ | H | H | O | CH$_3$O | CH$_3$O | 184–186°(d) |
| H | 4-CF$_3$ | CH$_3$ | CH$_3$ | H | H | O | CH$_3$O | CH$_3$O | 157–167° |
| H | 4-NH$_2$ | CH$_3$ | CH$_3$ | H | H | O | CH$_3$O | CH$_3$O | 175–185°(d) |
| H | 4-N(CH$_3$)$_2$ | CH$_3$ | CH$_3$ | H | H | O | CH$_3$ | CH$_3$O | |
| H | 4-CN | CH$_3$ | CH$_3$ | H | H | O | CH$_3$O | CH$_3$O | |
| H | 4-CH$_3$S— | CH$_3$ | CH$_3$ | H | H | O | CH$_3$O | CH$_3$O | |
| H | 4-CH$_3$S(=O)— | CH$_3$ | CH$_3$ | H | H | O | CH$_3$O | CH$_3$O | |
| H | 4-CH$_3$S(=O)$_2$— | CH$_3$ | CH$_3$ | H | H | O | CH$_3$O | CH$_3$O | |
| H | 4-CH$_3$O | CH$_3$ | CH$_3$ | H | H | O | CH$_3$O | CH$_3$O | 186.5–189°(d) |
| H | 3-Cl | CH$_3$ | CH$_3$ | H | H | O | CH$_3$O | CH$_3$O | |
| H | 5-F | CH$_3$ | CH$_3$ | H | H | O | CH$_3$O | CH$_3$O | |
| H | 6-Cl | CH$_3$ | CH$_3$ | H | H | O | CH$_3$O | CH$_3$O | |
| H | H | C$_2$H$_5$ | C$_2$H$_5$ | H | H | O | CH$_3$O | CH$_3$O | 175–177° |
| H | H | C$_2$H$_5$ | C$_2$H$_5$ | H | H | O | CH$_3$ | CH$_3$O | 170–176° |
| H | H | C$_2$H$_5$ | C$_2$H$_5$ | H | H | O | CH$_3$ | CH$_3$ | 179–181° |
| H | H | C$_2$H$_5$ | C$_2$H$_5$ | H | H | S | CH$_3$O | CH$_3$O | |
| H | H | C$_2$H$_5$ | C$_2$H$_5$ | H | H | S | CH$_3$ | CH$_3$O | |
| H | 4-NH$_2$ | CH$_3$ | CH$_3$ | H | H | O | CH$_3$O | CH$_3$O | 175–185°(d) |
| H | 4-C$_2$H$_5$O— | CH$_3$ | CH$_3$ | H | H | O | CH$_3$O | CH$_3$O | 180–183°(d) |
| H | 4-C$_2$H$_5$O— | CH$_3$ | CH$_3$ | H | H | O | CH$_3$O | CH$_3$ | 179–181°(d) |
| H | 4-C$_2$H$_5$O— | CH$_3$ | CH$_3$ | H | H | O | CH$_3$ | CH$_3$ | 170–180°(d) |
| H | H | n-C$_3$H$_7$ | n-C$_3$H$_7$ | H | H | O | CH$_3$O | CH$_3$O | 110–165° |
| H | H | n-C$_3$H$_7$ | n-C$_3$H$_7$ | H | H | O | CH$_3$O | CH$_3$ | glass |
| H | H | n-C$_3$H$_7$ | CH$_3$ | H | H | O | CH$_3$O | CH$_3$O | glass |
| H | H | n-C$_3$H$_7$ | CH$_3$ | H | H | O | CH$_3$O | CH$_3$ | 170–172° |
| H | H | sec-C$_4$H$_9$ | CH$_3$ | H | H | O | CH$_3$O | CH$_3$O | glass |
| H | H | sec-C$_4$H$_9$ | CH$_3$ | H | H | O | CH$_3$O | CH$_3$ | glass |
| H | H | n-C$_4$H$_9$ | CH$_3$ | H | H | O | CH$_3$O | CH$_3$O | |
| H | H | n-C$_4$H$_9$ | CH$_3$ | H | H | O | CH$_3$O | CH$_3$ | 123–134° |
| H | H | i-C$_3$H$_7$ | i-C$_3$H$_7$ | H | H | O | CH$_3$O | CH$_3$O | glass |
| H | H | i-C$_3$H$_7$ | i-C$_3$H$_7$ | H | H | O | CH$_3$O | CH$_3$— | 167–174° |
| H | H | CH$_2$=CHCH$_2$— | CH$_2$=CHCH$_2$— | H | H | O | CH$_3$O | CH$_3$O | |
| H | H | n-C$_6$H$_{13}$ | CH$_3$ | H | H | O | CH$_3$O | CH$_3$O | |
| H | H | cyclopropyl | CH$_3$ | H | H | O | CH$_3$O | CH$_3$O | |
| H | H | cyclopentyl | CH$_3$ | H | H | O | CH$_3$O | CH$_3$O | |
| H | H | cyclohexyl | CH$_3$ | H | H | O | CH$_3$O | CH$_3$O | |
| H | H | cyclohexenyl | CH$_3$ | H | H | O | CH$_3$O | CH$_3$O | |
| H | H | 2-methylcyclohexyl | CH$_3$ | H | H | O | CH$_3$O | CH$_3$O | |
| H | H | NC–C(CH$_3$)$_2$– | CH$_3$ | H | H | O | CH$_3$O | CH$_3$O | |
| H | H | NCCH$_2$— | NCCH$_2$— | H | H | O | CH$_3$O | CH$_3$O | |
| H | H | NCCH$_2$CH$_2$— | NCCH$_2$CH$_2$— | H | H | O | CH$_3$O | CH$_3$O | |
| H | H | CH$_3$O(CH$_2$)$_2$— | CH$_3$O(CH$_2$)$_2$— | H | H | O | CH$_3$O | CH$_3$O | |
| H | H | CH$_3$OCH(CH$_3$)–CH$_2$— | CH$_3$OCH(CH$_3$)–CH$_2$— | H | H | O | CH$_3$O | CH$_3$O | |

TABLE II-continued

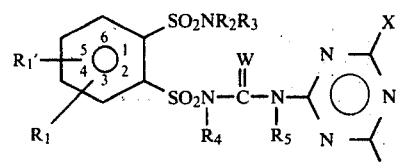

| R1' | R1 | R2 | R3 | R4 | R5 | W | X | Y | m.p.(°C.) |
|---|---|---|---|---|---|---|---|---|---|
| H | H | CH₃CH₂— | CH₃CH₂— | H | H | S | CH₃O | CH₃O | 154–156°(d) |
| H | H | n-C₆H₁₃ | n-C₄H₉ | H | H | O | CH₃O | CH₃O | |
| H | H | CH₃O | CH₃ | H | H | O | CH₃O | CH₃O | 190–194° |
| H | H | —CH₂CO₂CH₃ | —CH₂CO₂CH₃ | H | H | O | CH₃O | CH₃O | |
| H | H | —CHCO₂CH₃<br>\|<br>CH₃ | —CHCO₂CH₃<br>\|<br>CH₃ | H | H | O | CH₃O | CH₃O | |
| H | H | —CH₂CO₂—iPr | —CH₂CO₂—iPr | H | H | O | CH₃O | CH₃O | |
| H | H | —CH₂C(O)N(CH₃)₂ | —CH₂C(O)N(CH₃)₂ | H | H | O | CH₃O | CH₃O | |
| H | H | —CH₂C(O)N(C₃H₇)₂ | —CH₂C(O)N(C₃H₇)₂ | H | H | O | CH₃O | CH₃O | |
| H | H | —CH(CH₃)C(O)N(CH₃)₂ | —CH(CH₃)C(O)N(CH₃)₂ | H | H | O | CH₃O | CH₃O | |
| H | H | —CH₂CH₂CH₂CH₂— | | H | H | O | CH₃O | CH₃O | 208–210°(d) |
| H | H | —CH₂CH₂CH₂CH₂— | | H | H | O | CH₃O | CH₃ | |
| H | H | —CH₂CH₂CH₂CH₂— | | H | H | O | CH₃ | CH₃ | 217–219°(d) |
| H | 4-Cl | —CH₂CH₂CH₂CH₂— | | H | H | O | CH₃O | CH₃O | |
| H | 4-CF₃ | —CH₂CH₂CH₂CH₂— | | H | H | O | CH₃O | CH₃O | |
| H | H | —(CH₂)₅— | | H | H | O | CH₃O | CH₃O | 197–199° |
| H | H | —(CH₂)₆— | | H | H | O | CH₃O | CH₃O | glass |
| H | H | —(CH₂)₂—O—(CH₂)₂— | | H | H | O | CH₃O | CH₃O | 173–177° |
| H | H | C₆H₅— | CH₃ | H | H | O | CH₃O | CH₃ | 180–183° |
| H | H | 4-Cl-C₆H₄— | CH₃ | H | H | O | CH₃O | CH₃ | |
| H | H | 4-CH₃-C₆H₄— | CH₃ | H | H | O | CH₃O | CH₃ | |
| H | H | 4-Br-C₆H₄— | CH₃ | H | H | O | CH₃O | CH₃ | |
| H | H | 4-F-C₆H₄— | CH₃ | H | H | O | CH₃O | CH₃ | 182–184°(d) |
| H | H | C₆H₅CH₂— | CH₃ | H | H | O | CH₃O | CH₃ | |
| H | H | C₆H₅CH(CH₃)— | CH₃ | H | H | O | CH₃O | CH₃ | |
| H | H | 4-Cl-C₆H₄-CH₂— | —CH₃ | H | H | O | CH₃O | CH₃ | |
| H | H | 4-CH₃-C₆H₄-CH₂— | —CH₃ | H | H | O | CH₃O | CH₃ | |
| H | H | 4-Cl-C₆H₄-CH(CH₃)— | —CH₃ | H | H | O | CH₃O | CH₃ | |
| H | H | 4-F-C₆H₄-CH₂— | CH₃ | H | H | O | CH₃O | CH₃ | |
| H | H | 4-Br-C₆H₄-CH(CH₃)— | CH₃ | H | H | O | CH₃O | CH₃ | |
| H | 4-CF₃ | CH₃ | CH₃ | H | H | O | CH₃O | CH₃ | 175–180° |
| H | 4-CF₃ | CH₃ | CH₃ | H | H | O | CH₃ | CH₃ | 194–197°(d) |
| H | 4-Cl | CH₃ | CH₃ | H | H | O | CH₃O | CH₃O | 194–197° |
| H | 4-Cl | CH₃ | CH₃ | H | H | O | CH₃ | CH₃ | 219–222° |

TABLE II-continued

| $R_1'$ | $R_1$ | $R_2$ | $R_3$ | $R_4$ | $R_5$ | W | X | Y | m.p.(°C.) |
|---|---|---|---|---|---|---|---|---|---|
| H | 4-Cl | $C_2H_5$ | $C_2H_5$ | H | H | O | $CH_3O$ | $CH_3O$ | 190–195°(d) |
| H | 4-Cl | $C_2H_5$ | $C_2H_5$ | H | H | O | $CH_3O$ | $CH_3$ | 170–181° |
| H | 4-$CH_3O$ | $CH_3$ | $CH_3$ | H | H | O | $CH_3O$ | $CH_3$ | 193–195°(d) |
| H | 4-$CH_3O$ | $CH_3$ | $CH_3$ | H | H | O | $CH_3$ | $CH_3$ | 183.5–185° |
| 5-Cl | 4-Cl | $CH_3$ | $CH_3$ | H | H | O | $CH_3O$ | $CH_3O$ | |
| 5-F | 4-Cl | $CH_3$ | $CH_3$ | H | H | O | $CH_3O$ | $CH_3O$ | |
| 5-Br | 4-Cl | $CH_3$ | $CH_3$ | H | H | O | $CH_3O$ | $CH_3O$ | |
| 5-$CH_3$ | 4-$CH_3$ | $CH_3$ | $CH_3$ | H | H | O | $CH_3O$ | $CH_3O$ | |
| 5-$CH_3O$ | 4-$CH_3O$ | $CH_3$ | $CH_3$ | H | H | O | $CH_3O$ | $CH_3O$ | |
| 6-Cl | 4-Cl | $CH_3$ | $CH_3$ | H | H | O | $CH_3O$ | $CH_3O$ | |
| 4-Cl | 3-Cl | $CH_3$ | $CH_3$ | H | H | O | $CH_3O$ | $CH_3O$ | |
| H | 4-F | $CH_3$ | $CH_3$ | H | H | O | $CH_3O$ | $CH_3$ | 177–188°(d) |
| H | 4-F | $CH_3$ | $CH_3$ | H | H | O | $CH_3$ | $CH_3$ | 210–212°(d) |
| H | 4-$CH_3$ | $CH_3$ | $CH_3$ | H | H | O | $CH_3O$ | $CH_3O$ | 202–204°(d) |
| H | 4-$CH_3$ | $CH_3$ | $CH_3$ | H | H | O | $CH_3$ | $CH_3$ | 210–213°(d) |
| H | 4-$NO_2$ | $CH_3$ | $CH_3$ | H | H | O | $CH_3O$ | $CH_3$ | 180–184°(d) |
| H | 4-$NO_2$ | $CH_3$ | $CH_3$ | H | H | O | $CH_3$ | $CH_3$ | 188–192°(d) |
| H | 4-$NH_2$ | $CH_3$ | $CH_3$ | H | H | O | $CH_3O$ | $CH_3$ | |
| H | 4-$NH_2$ | $CH_3$ | $CH_3$ | H | H | O | $CH_3$ | $CH_3$ | |
| H | 4-$N(CH_3)_2$ | $CH_3$ | $CH_3$ | H | H | O | $CH_3O$ | $CH_3$ | |
| H | 4-$N(CH_3)_2$ | $CH_3$ | $CH_3$ | H | H | O | $CH_3$ | $CH_3$ | |
| H | 4-CN | $CH_3$ | $CH_3$ | H | H | O | $CH_3O$ | $CH_3$ | |
| H | 4-CN | $CH_3$ | $CH_3$ | H | H | O | $CH_3$ | $CH_3$ | |
| H | 4-$CH_3S-$ | $CH_3$ | $CH_3$ | H | H | O | $CH_3O$ | $CH_3$ | |
| H | 4-$CH_3S-$ | $CH_3$ | $CH_3$ | H | H | O | $CH_3$ | $CH_3$ | |
| H | 4-$CH_3SO_2-$ | $CH_3$ | $CH_3$ | H | H | O | $CH_3O$ | $CH_3$ | |
| H | 4-$CH_3SO_2-$ | $CH_3$ | $CH_3$ | H | H | O | $CH_3$ | $CH_3$ | |
| H | 4-N=C=O | $CH_3$ | $CH_3$ | H | H | O | $CH_3O$ | $CH_3O$ | |
| H | 4-NHC(O)$CH_3$ | $CH_3$ | $CH_3$ | H | H | O | $CH_3O$ | $CH_3O$ | |
| H | 4-NHC(O)CH$(CH_3)_2$ | $CH_3$ | $CH_3$ | H | H | O | $CH_3O$ | $CH_3O$ | |
| H | 4-NHC(O)NH$CH_3$ | $CH_3$ | $CH_3$ | H | H | O | $CH_3O$ | $CH_3O$ | |
| H | 4-NHC(O)NHCH$(CH_3)_2$ | $CH_3$ | $CH_3$ | H | H | O | $CH_3O$ | $CH_3O$ | |
| H | H | $CH_3$ | $CH_3$ | H | H | O | $CH_3$ | $-OCHCO_2H$ $\vert$ $CH_3$ | |
| H | H | $CH_3$ | $CH_3$ | H | H | O | $CH_3$ | $-CO_2CH_3$ | |
| H | H | $CH_3$ | $CH_3$ | H | H | O | $CH_3$ | $CO_2H$ | |
| H | H | $CH_3$ | $CH_3$ | H | H | O | $CH_3$ | $CO_2-\!\!<$ | |
| H | H | $CH_3$ | $CH_3$ | H | H | O | $CH_3$ | $CH_2CO_2CH_3$ | |
| H | H | $CH_3$ | $CH_3$ | H | H | O | $CH_3$ | $CH_2CO_2-\!\!<$ | |
| H | H | $CH_3$ | $CH_3$ | H | H | O | $CH_3$ | $CH_2CO_2H$ | |
| H | H | $CH_3O$ | $CH_3$ | H | H | O | $CH_3O$ | $CH_3$ | 182–186° |
| H | H | $C_2H_5$ | $CH_3$ | H | H | O | $CH_3O$ | $CH_3O$ | 179–180° |
| H | H | $C_2H_5$ | $CH_3$ | H | H | O | $CH_3O$ | $CH_3$ | 189–192° |
| H | H | n-$C_3H_7$ | $CH_3$ | H | H | O | $CH_3$ | $CH_3$ | 144–147° |
| H | H | i-$C_3H_7$ | $CH_3$ | H | H | O | $CH_3O$ | $CH_3O$ | 215–217° |
| H | H | i-$C_3H_7$ | $CH_3$ | H | H | O | $CH_3O$ | $CH_3$ | 181–195° |
| H | H | i-$C_3H_7$ | $CH_3$ | H | H | O | $CH_3$ | $CH_3$ | 187–190° |
| H | H | n-$C_4H_9$ | $CH_3$ | H | H | O | $CH_3O$ | $CH_3O$ | |
| H | H | n-$C_4H_9$ | $CH_3$ | H | H | O | $CH_3$ | $CH_3$ | 113–116° |
| H | H | sec-$C_4H_9$ | $CH_3$ | H | H | O | $CH_3$ | $CH_3$ | glass |
| H | H |  | $CH_3$ | H | H | O | $CH_3O$ | $CH_3O$ | 114–116° |
| H | H | | $CH_3$ | H | H | O | $CH_3$ | $CH_3$ | 189–191° |
| H | H | 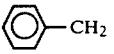 | $CH_3$ | H | H | O | $CH_3O$ | $CH_3O$ | 179–183°(d) |

TABLE II-continued

Structure: cyclohexane ring (positions 1-6) with R1' at position 5, R1 at position 4, SO2NR2R3 at position 1, SO2N(R4)–C(=W)–N(R5)– linked to a triazine ring bearing X (via CH) and Y (via CH), with N atoms in ring.

| R1' | R1 | R2 | R3 | R4 | R5 | W | X | Y | m.p.(°C.) |
|---|---|---|---|---|---|---|---|---|---|
| H | H |  | CH3 (R2 = PhCH2–) | H | H | O | CH3 | CH3 | 171–175°(d) |
| H | H | PhCH2– | CH3 | H | H | O | CH3 | CH3 |  |
| H | H | i-C3H7 | C2H5 | H | H | O | CH3O | CH3O | 170–185° |
| H | H | i-C3H7 | C2H5 | H | H | O | CH3O | CH3 | 162–170° |
| H | H | i-C3H7 | C2H5 | H | H | O | CH3 | CH3 | 161–164° |
| H | H | n-C3H7 | n-C3H7 | H | H | O | CH3 | CH3 |  |
| H | H | i-C3H7 | i-C3H7 | H | H | O | CH3 | CH3 | 196–198° |
| H | H | —(CH2)5— |  | H | H | O | CH3O | CH3 | 191–195° |
| H | H | —(CH2)5— |  | H | H | O | CH3 | CH3 | 197–201° |
| H | H | —CH2CH2OCH2CH2— |  | H | H | O | CH3O | CH3 | 209–212° |
| H | H | —CH2CH2OCH2CH2— |  | H | H | O | CH3 | CH3 | 192–199° |
| H | H | —(CH2)6— |  | H | H | O | CH3O | CH3 | glass |
| H | H | —(CH2)6— |  | H | H | O | CH3 | CH3 | 184–186° |
| H | H | H | CH3 | H | H | O | CH3O | CH3 |  |
| H | H | H | C2H5 | H | H | O | CH3O | CH3 |  |
| H | H | H | n-C3H7 | H | H | O | CH3O | CH3 |  |
| H | H | H | i-C3H7 | H | H | O | CH3O | CH3 |  |
| H | H | H | n-C4H9 | H | H | O | CH3O | CH3 |  |
| H | H | H | t-C4H9 | H | H | O | CH3O | CH3 |  |
| H | H | H | sec-C4H9 | H | H | O | CH3O | CH3 |  |
| H | H | H | CH2=CHCH2— | H | H | O | CH3O | CH3 |  |
| H | H | H | —CH2CO2CH3 | H | H | O | CH3O | CH3 |  |
| H | H | H | —n-C6H13 | H | H | O | CH3O | CH3 |  |
| H | H | CH3— | Ph-CH2O— | H | H | O | CH3O | CH3 |  |
| H | H |  | CH3 (R2 = PhCH(CH3)O–) | H | H | O | CH3O | CH3 |  |
| H | H |  | CH3 (R2 = 2-Cl-C6H4-CH2O–) | H | H | O | CH3O | CH3 |  |
| H | H |  | CH3 (R2 = 2-CH3-C6H4-CH2O–) | H | H | O | CH3O | CH3 |  |
| H | H | CF3CH2— | CF3CH2— | H | H | O | CH3O | CH3 |  |
| H | H | CH3— | CF3CHFCF2— | H | H | O | CH3O | CH3 |  |
| H | H | CH3— | HBrFCCF2— | H | H | O | CH3O | CH3 |  |
| H | H | CH3— | HClFCCF2— | H | H | O | CH3O | CH3 |  |
| H | H | CH3— | HCF2CF2— | H | H | O | CH3O | CH3 | 171–173°(d) |
| H | H | CH3— | HCF2CF2— | H | H | O | CH3O | CH3O | 155–157°(d) |
| H | H | CH3— | HCF2CF2— | H | H | O | CH3 | CH3 | 184–188°(d) |
| H | 4-NHCOCH3 | CH3 | CH3 | H | H | O | CH3O | CH3 |  |
| H | 4-NHCO—i-C3H7 | CH3 | CH3 | H | H | O | CH3O | CH3 |  |
| H | H | CH3 | CH3 | H | H | O | CH3O | —CH2CN |  |
| H | H | CH3 | CH3 | H | H | O | CH3O | —CH2CH2CN |  |
| H | H | CH3 | CH3 | H | H | O | CH3O | —CH2Cl |  |
| H | H | CH3 | CH3 | H | H | O | CH3O | —N3 |  |
| H | H | CH3 | CH3 | H | H | O | CH3O | —OCH2CH=CH2 |  |
| H | H | CH3 | CH3 | H | H | O | CH3O | —OCH2C≡CH |  |
| H | H | CH3 | CH3 | H | H | O | CH3O | —N(CH3)—CH2CN |  |
| H | 4-COCH3 | CH3 | CH3 | H | H | O | CH3 | CH3 |  |
| H | 4-CO—i-C3H7 | CH3 | CH3 | H | H | O | CH3 | CH3 |  |

TABLE II-continued

| R1' | R1 | R2 | R3 | R4 | R5 | W | X | Y | m.p.(°C.) |
|---|---|---|---|---|---|---|---|---|---|
| H | 4-CH2OCH3 | CH3 | CH3 | H | H | O | CH3 | CH3 | |
| H | 4-CH2O—i-C3H7 | CH3 | CH3 | H | H | O | CH3 | CH3 | |
| H | 4-CH2SCH3 | CH3 | CH3 | H | H | O | CH3 | CH3 | |
| H | 4-CH2SO2CH3 | CH3 | CH3 | H | H | O | CH3 | CH3 | |
| H | 4-CH2S(O)CH3 | CH3 | CH3 | H | H | O | CH3 | CH3 | |
| H | H | —CH2C≡CH | CH3 | H | H | O | CH3O | CH3O | |
| H | H | —C(CH3)2C≡CH | CH3 | H | H | O | CH3O | CH3O | |
| H | H | —CH2-(tetrahydrothiopyranyl) | CH3 | H | H | O | CH3O | CH3O | |
| H | H | —CH2-cyclopropyl | CH3 | H | H | O | CH3O | CH3O | |
| H | H | CH3 | CH3 | H | H | O | CH3O | —CH2CH3 | |
| H | H | CH3 | CH3 | H | H | O | CH3O | —CH2CH2CH3 | |
| H | H | CH3 | CH3 | H | H | O | CH3O | —CH(CH3)2 | |

TABLE II-a

| A | R1' | R1 | R4 | R5 | W | X | Y | m.p.(°C.) |
|---|---|---|---|---|---|---|---|---|
| CF3CH2O— | H | H | H | H | O | CH3O | CH3O | 194–196°(d) |
| CF3CH2O— | H | H | H | H | O | CH3O | CH3 | 189–190°(d) |
| CF3CH2O— | H | H | H | H | O | CH3 | CH3 | 186–189°(d) |
| C6H5-O— | H | H | H | H | O | CH3O | CH3O | 190–194°(d) |
| C6H5-O— | H | H | H | H | O | CH3O | CH3 | 191–193°(d) |
| C6H5-O— | H | H | H | H | O | CH3 | CH3 | 199–201°(d) |
| CCl3CH2O— | H | H | H | H | O | CH3O | CH3O | |
| CCl3CH2O— | H | H | H | H | O | CH3O | CH3 | |
| CCl3CH2O— | H | H | H | H | O | CH3 | CH3 | |
| CBr3CH2O— | H | H | H | H | O | CH3O | CH3O | |
| HCF2CH2O— | H | H | H | H | O | CH3O | CH3O | |
| HCF2CF2CH2O— | H | H | H | H | O | CH3O | CH3O | |
| CF3CF3CH2O— | H | H | H | H | O | CH3O | CH3O | |
| CF3(CF2)2CH2O— | H | H | H | H | O | CH3O | CH3O | |
| CF3CH(CH3)O— | H | H | H | H | O | CH3O | CH3O | |
| (CF3)2CHO— | H | H | H | H | O | CH3O | CH3O | |
| (CF3)2CHO— | H | H | H | H | O | CH3O | CH3 | |
| (CF3)2CHO— | H | H | H | H | O | CH3 | CH3 | |
| 4-Cl-C6H4-O— | H | H | H | H | O | CH3O | CH3O | |

| A | R1' | R1 | R4 | R5 | W | X1 | Y1 | m.p.(°C.) |
|---|---|---|---|---|---|---|---|---|
| 4-CH3-C6H4-O— | H | H | H | H | O | CH3O | CH3O | |
| 4-CH3O-C6H4-O— | H | H | H | H | O | CH3O | CH3O | |
| 4-O2N-C6H4-O— | H | H | H | H | O | CH3O | CH3O | |

TABLE II-a-continued

| R1' | R1 | (position)-sub | R4 | R5 | W | X | Y |
|---|---|---|---|---|---|---|---|
| CF$_3$CH$_2$O | H | 4-Cl | H | H | O | CH$_3$O | CH$_3$O |
| CF$_3$CH$_2$O | H | 4-CF$_3$ | H | H | O | CH$_3$O | CH$_3$O |
| CF$_3$CH$_2$O | H | 4-CH$_3$O | H | H | O | CH$_3$O | CH$_3$O |
| CF$_3$CH$_2$O | H | 4-NO$_2$ | H | H | O | CH$_3$O | CH$_3$O |
| CF$_3$CH$_2$O | H | 4-CN | H | H | O | CH$_3$O | CH$_3$O |
| CF$_3$CH$_2$O | H | 4-F | H | H | O | CH$_3$O | CH$_3$O |
| CF$_3$CH$_2$O | H | 4-CH$_3$ | H | H | O | CH$_3$O | CH$_3$O |

TABLE II-b

| R$_1$ | A | B | X$_1$ | Y$_1$ | m.p.(°C.) |
|---|---|---|---|---|---|
| H | —N(CH$_3$)$_2$ | CH$_3$— | CH$_3$— | CH$_3$O | |
| H | —N(CH$_3$)$_2$ | i-C$_3$H$_7$— | CH$_3$— | CH$_3$O | |
| H | —N(CH$_3$)$_2$ | n-C$_6$H$_{13}$— | CH$_3$— | CH$_3$O | |
| H | —N(CH$_3$)$_2$ | CH$_3$OCH$_2$CH$_2$— | CH$_3$— | CH$_3$O | |
| H | —N(CH$_3$)$_2$ | C$_2$H$_5$OCH$_2$CH$_2$— | CH$_3$— | CH$_3$O | |
| H | —N(CH$_3$)$_2$ | CH$_3$O(CH$_2$)$_3$— | CH$_3$— | CH$_3$O | |
| H | —N(CH$_3$)$_2$ | CH$_3$O$_2$CCH$_2$— | CH$_3$— | CH$_3$O | |
| H | —N(CH$_3$)$_2$ | i-C$_3$H$_7$O$_2$CCH$_2$— | CH$_3$— | CH$_3$O | |
| H | —N(CH$_3$)$_2$ | CH$_3$NC(O)CH$_2$—<br>    \|<br>   OCH$_3$ | CH$_3$— | CH$_3$O | |
| H | —N(CH$_3$)$_2$ | (CH$_3$)$_2$NC(O)CH$_2$— | CH$_3$— | CH$_3$O | |
| H | —N(CH$_3$)$_2$ | (CH$_3$CH$_2$CH$_2$)$_2$NC(O)CH$_2$— | CH$_3$— | CH$_3$O | |
| H | —N(CH$_3$)$_2$ | H$_2$NC(O)CH$_2$— | CH$_3$— | CH$_3$O | |
| H | —N(CH$_3$)$_2$ | C$_6$H$_5$—CH$_2$— | CH$_3$— | CH$_3$O | |
| H | —N(CH$_3$)$_2$ | 2-Cl-C$_6$H$_4$—CH$_2$— | CH$_3$— | CH$_3$O | |
| H | —N(CH$_3$)$_2$ | NCCH$_2$— | CH$_3$— | CH$_3$O | |
| H | —N(CH$_3$)$_2$ | H$_2$C=CHCH$_2$— | CH$_3$— | CH$_3$O | |
| H | —N(CH$_3$)$_2$ | HC≡CCH$_2$— | CH$_3$— | CH$_3$O | |
| H | —N(CH$_3$)$_2$ | CH$_3$OCH$_2$— | CH$_3$— | CH$_3$O | |
| H | —N(CH$_3$)$_2$ | CH$_3$(CH$_2$)$_3$OCH$_2$— | CH$_3$— | CH$_3$O | |
| H | —N(CH$_3$)$_2$ | CH$_3$O(CH$_2$)$_2$OCH$_2$— | CH$_3$— | CH$_3$O | |
| H | —N(CH$_3$)$_2$ | C$_2$H$_5$O(CH$_2$)$_2$OCH$_2$— | CH$_3$— | CH$_3$O | |
| H | —N(CH$_3$)$_2$ | CH$_3$HNC(O)CH$_2$— | CH$_3$— | CH$_3$O | |
| H | —N(CH$_3$)$_2$ | CH$_3$CH$_2$HNC(O)CH$_2$— | CH$_3$— | CH$_3$O | |
| H | —N(CH$_3$)$_2$ | (CH$_3$)$_2$CHHNC(O)CH$_2$— | CH$_3$— | CH$_3$O | |
| H | —N(C$_2$H$_5$)$_2$ | CH$_3$ | CH$_3$O | CH$_3$O | |
| H | —N(C$_2$H$_5$)(CH$_3$) | CH$_3$ | CH$_3$O | CH$_3$ | |
| H | —N(i-C$_3$H$_7$)(CH$_3$) | CH$_3$ | CH$_3$O | CH$_3$ | |
| H | —N(n-C$_6$H$_{13}$)(CH$_3$) | CH$_3$ | CH$_3$O | CH$_3$ | |
| H | —N(CH$_2$C$_6$H$_5$)(CH$_3$) | CH$_3$ | CH$_3$O | CH$_3$ | |

TABLE II-b-continued

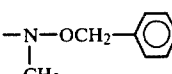

| R₁ | A | B | X₁ | Y₁ | m.p.(°C.) |
|---|---|---|---|---|---|
| H | —N(CH₃)—OCH₂—C₆H₅ | CH₃ | CH₃O | CH₃ | |
| H | —NHCH₃ | CH₃ | CH₃O | CH₃ | |
| H | —NHC₂H₅ | CH₃ | CH₃O | CH₃ | |
| H | —NHC₆H₁₃ | CH₃ | CH₃O | CH₃ | |
| H | —N(CH₃)—CF₂CF₂H | CH₃ | CH₃O | CH₃ | |
| H | —OCH₂CF₃ | CH₃ | CH₃O | CH₃ | |
| H | —N(pyrrolidinyl) | CH₃ | CH₃O | CH₃ | |
| H | —N(CH₃)—CH₂CN | CH₃ | CH₃O | CH₃ | |
| H | —N(CH₂CN)₂ | CH₃ | CH₃O | CH₃ | |
| 4-Cl | —N(CH₃)₂ | CH₃ | CH₃O | CH₃ | |
| 4-CF₃ | —N(CH₃)₂ | CH₃ | CH₃O | CH₃ | |
| 4-NO₂ | —N(CH₃)₂ | CH₃ | CH₃O | CH₃ | |
| 4-CH₃O | —N(CH₃)₂ | CH₃ | CH₃O | CH₃ | |
| 4-F | —N(CH₃)₂ | CH₃ | CH₃O | CH₃ | |
| 4-Br | —N(CH₃)₂ | CH₃ | CH₃O | CH₃ | |
| 4-CH₃ | —N(CH₃)₂ | CH₃ | CH₃O | CH₃ | |
| 4-CN | —N(CH₃)₂ | CH₃ | CH₃O | CH₃ | |
| 4-N(CH₃)₂ | —N(CH₃)₂ | CH₃ | CH₃O | CH₃ | |
| 4-SCH₃ | —N(CH₃)₂ | CH₃ | CH₃O | CH₃ | |
| 4-SO₂CH₃ | —N(CH₃)₂ | CH₃ | CH₃O | CH₃ | |
| 4-NH₂ | —N(CH₃)₂ | CH₃ | CH₃O | CH₃ | |
| 4-NHC(O)CH₃ | —N(CH₃)₂ | CH₃ | CH₃O | CH₃ | |
| 4-NHC(O)NHCH₃ | —N(CH₃)₂ | CH₃ | CH₃O | CH₃ | |
| 4-NHCOCH₃ | —N(CH₃)₂ | CH₃ | CH₃O | CH₃ | |
| H | —N(CH₃)₂ | CH₃ | CH₃O | CH₃O | |
| H | —N(CH₃)₂ | CH₃ | CH₃ | CH₃ | |
| H | —N(CH₃)₂ | CH₃ | H | CH₃ | |
| H | —N(CH₃)₂ | CH₃ | H | CH₃O | |
| H | —N(CH₃)₂ | CH₃ | H | C₂H₅O | |
| H | —N(CH₃)₂ | CH₃ | CH₃ | C₂H₅O | |
| H | —N(CH₃)₂ | CH₃ | CH₃O | C₂H₅O | |

TABLE III

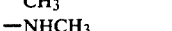

| R₁' | R₁ | R₂ | R₃ | R₄ | R₅ | W | X₁ | Y₁ | m.p.(°C.) |
|---|---|---|---|---|---|---|---|---|---|
| H | H | CH₃ | CH₃ | H | H | O | H | CH₃O | |
| H | H | CH₃ | CH₃ | H | H | O | H | CH₃ | |
| H | H | CH₃ | CH₃ | H | H | O | H | C₂H₅O | |
| H | H | CH₃ | CH₃ | H | H | O | CH₃ | CH₃ | 189–193°(d) |
| H | H | CH₃ | CH₃ | H | H | O | CH₃ | CH₃O | |
| H | H | CH₃ | CH₃ | H | H | O | CH₃O | CH₃O | |
| H | H | CH₃ | CH₃ | CH₃ | H | O | CH₃ | CH₃ | |
| H | H | CH₃ | CH₃ | H | CH₃ | O | CH₃ | CH₃ | |
| H | H | CH₃ | CH₃ | H | H | S | CH₃ | CH₃ | |
| H | H | CH₃CH₂— | H | H | H | O | CH₃ | CH₃ | |
| H | H | —(CH₂)₄— | | H | H | O | CH₃ | CH₃ | |

TABLE III-continued

| $R_1'$ | $R_1$ | $R_2$ | $R_3$ | $R_4$ | $R_5$ | W | $X_1$ | $Y_1$ | m.p.(°C.) |
|---|---|---|---|---|---|---|---|---|---|
| H | 4-Cl | —(CH$_2$)$_4$— | | H | H | O | CH$_3$ | CH$_3$ | |
| H | 4-CF$_3$ | CH$_3$ | CH$_3$ | H | H | O | CH$_3$ | CH$_3$ | |
| H | 4-CH$_3$S(O)$_2$— | CH$_3$ | CH$_3$ | H | H | O | CH$_3$ | CH$_3$ | |
| H | 4-CN | CH$_3$ | CH$_3$ | H | H | O | CH$_3$ | CH$_3$ | |
| H | H | CH$_2$=CHCH$_2$— | CH$_2$=CHCH$_2$— | H | H | O | CH$_3$ | CH$_3$ | |
| H | H | —(CH$_2$)$_2$—O—(CH$_2$)$_2$— | | H | H | O | CH$_3$ | CH$_3$ | |
| H | 4-NO$_2$ | CH$_3$ | CH$_3$ | H | H | O | CH$_3$ | CH$_3$ | |
| H | 4-CH$_3$O | CH$_3$ | CH$_3$ | H | H | O | CH$_3$ | CH$_3$ | |
| H | 4-CH$_3$— | CH$_3$ | CH$_3$ | H | H | O | CH$_3$ | CH$_3$ | |
| H | 3-Cl | CH$_3$ | CH$_3$ | H | H | O | CH$_3$ | CH$_3$ | |
| H | H | n-C$_6$H$_{13}$ | CH$_3$ | H | H | O | CH$_3$ | CH$_3$ | |
| H | H | NCCH$_2$CH$_2$— | NCCH$_2$CH$_2$— | H | H | O | CH$_3$ | CH$_3$ | |
| H | H | CH$_2$CO$_2$CH$_3$ | CH$_2$CO$_2$CH$_3$ | H | H | O | CH$_3$ | CH$_3$ | |
| H | 4-NCO | CH$_3$ | CH$_3$ | H | H | O | CH$_3$O | CH$_3$O | |
| H | 4-NHC(O)CH$_3$ | CH$_3$ | CH$_3$ | H | H | O | CH$_3$O | CH$_3$O | |
| H | 4-NHC(O)CH(CH$_3$)$_2$ | CH$_3$ | CH$_3$ | H | H | O | CH$_3$O | CH$_3$O | |
| H | 4-NH—C(O)NHCH$_3$ | CH$_3$ | CH$_3$ | H | H | O | CH$_3$O | CH$_3$O | |
| H | 4-NHC(O)NHCH(CH$_3$)$_2$ | CH$_3$ | CH$_3$ | H | H | O | CH$_3$O | CH$_3$O | |
| H | 4-NHCOCH$_3$ | CH$_3$ | CH$_3$ | H | H | O | CH$_3$O | CH$_3$O | |
| H | 4-NHCO—i-C$_3$H$_7$ | CH$_3$ | CH$_3$ | H | H | O | CH$_3$O | CH$_3$O | |
| H | 4-C(O)CH$_3$ | CH$_3$ | CH$_3$ | H | H | O | CH$_3$O | CH$_3$O | |
| H | 4-CH$_2$OCH$_3$ | CH$_3$ | CH$_3$ | H | H | O | CH$_3$O | CH$_3$O | |
| H | 4-CH$_2$SCH$_3$ | CH$_3$ | CH$_3$ | H | H | O | CH$_3$O | CH$_3$O | |
| H | 4-CH$_2$SO$_2$CH$_3$ | CH$_3$ | CH$_3$ | H | H | O | CH$_3$O | CH$_3$O | |
| H | H | —CF$_2$CF$_2$H | CH$_3$ | H | H | O | CH$_3$O | CH$_3$O | |
| H | H | H | CH$_3$ | H | H | O | CH$_3$O | CH$_3$ | |
| H | H | H | C$_2$H$_5$ | H | H | O | CH$_3$O | CH$_3$ | |
| H | H | H | n-C$_3$H$_7$ | H | H | O | CH$_3$O | CH$_3$ | |
| H | H | H | i-C$_3$H$_7$ | H | H | O | CH$_3$O | CH$_3$ | |
| H | H | H | n-C$_4$H$_9$ | H | H | O | CH$_3$O | CH$_3$ | |
| H | H | H | t-C$_4$H$_9$ | H | H | O | CH$_3$O | CH$_3$ | |
| H | H | H | sec-C$_4$H$_9$ | H | H | O | CH$_3$O | CH$_3$ | |
| H | H | H | CH$_2$=CHCH$_2$— | H | H | O | CH$_3$O | CH$_3$ | |
| H | H | H | —CH$_2$CO$_2$CH$_3$ | H | H | O | CH$_3$O | CH$_3$ | |
| H | H | H | —n-C$_6$H$_{13}$ | H | H | O | CH$_3$O | CH$_3$ | |
| H | H | C$_6$H$_5$CH$_2$O— | CH$_3$— | H | H | O | CH$_3$O | CH$_3$ | |
| H | H | C$_6$H$_5$CH(CH$_3$)O— | CH$_3$ | H | H | O | CH$_3$O | CH$_3$ | |
| H | H | (2-Cl-C$_6$H$_4$)CH$_2$O— | CH$_3$ | H | H | O | CH$_3$O | CH$_3$ | |
| H | H | (2-CH$_3$-C$_6$H$_4$)CH$_2$O— | CH$_3$ | H | H | O | CH$_3$O | CH$_3$ | |
| H | H | CF$_3$CH$_2$— | CF$_3$CH$_2$— | H | H | O | CH$_3$O | CH$_3$ | |
| H | H | CH$_3$— | CF$_3$CHFCF$_2$— | H | H | O | CH$_3$O | CH$_3$ | |
| H | H | CH$_3$— | HBrFCCF$_2$— | H | H | O | CH$_3$O | CH$_3$ | |
| H | H | CH$_3$— | HClFCCF$_2$— | H | H | O | CH$_3$O | CH$_3$ | |

TABLE III-continued

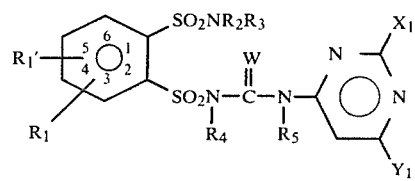

| R₁' | R₁ | R₂ | R₃ | R₄ | R₅ | W | X₁ | Y₁ | m.p.(°C.) |
|---|---|---|---|---|---|---|---|---|---|
| H | H | CH₃— | HCF₂CF₂— | H | H | O | CH₃O | CH₃ | |
| H | H | CH₃— | HCF₂CF₂— | H | H | O | CH₃O | CH₃O | |
| H | H | CH₃— | HCF₂CF₂— | H | H | O | CH₃ | CH₃ | |
| H | 4-NHCOCH₃ | CH₃ | CH₃ | H | H | O | CH₃O | CH₃ | |
| H | 4-NHCO—i-C₃H₇ | CH₃ | CH₃ | H | H | O | CH₃O | CH₃ | |
| H | H | —CH₂C≡CH | CH₃ | H | H | O | CH₃O | CH₃ | |
| H | H | —C(CH₃)₂C≡CH | CH₃ | H | H | O | CH₃O | CH₃ | |
| H | H | —CH₂-cyclopropyl | CH₃ | H | H | O | CH₃O | CH₃ | |
| H | H | —CH₂-(tetrahydrothiopyranyl) | CH₃ | H | H | O | CH₃O | CH₃ | |

TABLE III-a

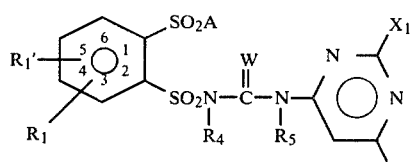

| A | R₁' | R₁ | R₄ | R₅ | W | X₁ | Y₁ | m.p.(°C.) |
|---|---|---|---|---|---|---|---|---|
| CF₃CH₂O— | H | H | H | H | O | CH₃O | CH₃O | |
| CF₃CH₂O— | H | H | H | H | O | CH₃O | CH₃ | |
| CF₃CH₂O— | H | H | H | H | O | CH₃ | CH₃ | |
| C₆H₅—O— | H | H | H | H | O | CH₃O | CH₃O | |
| C₆H₅—O— | H | H | H | H | O | CH₃O | CH₃ | |
| C₆H₅—O— | H | H | H | H | O | CH₃ | CH₃ | |
| CCl₃CH₂O— | H | H | H | H | O | CH₃O | CH₃O | |
| CCl₃CH₂O— | H | H | H | H | O | CH₃O | CH₃ | |
| CCl₃CH₂O— | H | H | H | H | O | CH₃ | CH₃ | |
| CBr₃CH₂O— | H | H | H | H | O | CH₃O | CH₃O | |
| HCF₂CH₂O— | H | H | H | H | O | CH₃O | CH₃O | |
| HCF₂CF₂CH₂O— | H | H | H | H | O | CH₃O | CH₃O | |
| CF₃CF₃CH₂O— | H | H | H | H | O | CH₃O | CH₃O | |
| CF₃(CF₂)₂CH₂O— | H | H | H | H | O | CH₃O | CH₃O | |
| CF₃CHO—\|CH₃ | H | H | H | H | O | CH₃O | CH₃O | |
| (CF₃)₂CHO— | H | H | H | H | O | CH₃O | CH₃O | |
| (CF₃)₂CHO— | H | H | H | H | O | CH₃O | CH₃ | |
| (CF₃)₂CHO— | H | H | H | H | O | CH₃ | CH₃ | |
| Cl—C₆H₄—O— | H | H | H | H | O | CH₃O | CH₃O | |
| CH₃—C₆H₄—O— | H | H | H | H | O | CH₃O | CH₃O | |
| CH₃O—C₆H₄—O— | H | H | H | O | O | CH₃O | CH₃O | |
| O₂N—C₆H₄—O— | H | H | H | H | O | CH₃O | CH₃O | |
| CF₃CH₂O | H | 4-Cl | H | H | O | CH₃O | CH₃O | |
| CF₃CH₂O | H | 4-CF₃ | H | H | O | CH₃O | CH₃O | |
| CF₃CH₂O | H | 4-CH₃O | H | H | O | CH₃O | CH₃O | |

TABLE III-a-continued

| A | $R_1'$ | $R_1$ | $R_4$ | $R_5$ | W | $X_1$ | $Y_1$ | m.p.(°C.) |
|---|---|---|---|---|---|---|---|---|
| $CF_3CH_2O$ | H | 4-$NO_2$ | H | H | O | $CH_3O$ | $CH_3O$ | |
| $CF_3CH_2O$ | H | 4-CN | H | H | O | $CH_3O$ | $CH_3O$ | |
| $CF_3CH_2O$ | H | 4-F | H | H | O | $CH_3O$ | $CH_3O$ | |
| $CF_3CH_2O$ | H | 4-$CH_3$ | H | H | O | $CH_3O$ | $CH_3O$ | |

TABLE IV

| $R_1'$ | $R_1$ | $R_2$ | $R_3$ | $R_4$ | $R_5$ | W | $X_1$ | $Y_1$ | m.p.(°C.) |
|---|---|---|---|---|---|---|---|---|---|
| H | H | $CH_3$ | $CH_3$ | H | H | O | H | $CH_3O$ | |
| H | H | $CH_3$ | $CH_3$ | H | H | O | H | $CH_3$ | |
| H | H | $CH_3$ | $CH_3$ | H | H | O | H | $C_2H_5O$ | |
| H | H | $CH_3$ | $CH_3$ | H | H | O | $CH_3$ | $CH_3$ | glass |
| H | H | $CH_3$ | $CH_3$ | H | H | O | $CH_3$ | $CH_3O$ | |
| H | H | $CH_3$ | $CH_3$ | H | H | O | $CH_3O$ | $CH_3O$ | |
| H | H | $CH_3$ | $CH_3$ | $CH_3$ | H | O | $CH_3$ | $CH_3$ | |
| H | H | $CH_3$ | $CH_3$ | H | $CH_3$ | O | $CH_3$ | $CH_3$ | |
| H | H | $CH_3$ | $CH_3$ | H | H | S | $CH_3$ | $CH_3$ | |
| H | H | $C_2H_5$ | $C_2H_5$ | H | H | O | $CH_3$ | $CH_3$ | |
| H | H | —$(CH_2)_4$— | | H | H | O | $CH_3$ | $CH_3$ | |
| H | 4-Cl | —$(CH_2)_4$— | | H | H | O | $CH_3$ | $CH_3$ | |
| H | 4-$CF_3$ | $C_2H_5$ | $C_2H_5$ | H | H | O | $CH_3$ | $CH_3$ | |
| H | 4-$CH_3S(O)_2$— | $CH_3$ | $CH_3$ | H | H | O | $CH_3$ | $CH_3$ | |
| H | 4-CN | $CH_3$ | $CH_3$ | H | H | O | $CH_3$ | $CH_3$ | |
| H | H | $CH_2$=$CHCH_2$— | $CH_2$=$CHCH_2$— | H | H | O | $CH_3$ | $CH_3$ | |
| H | H | —$(CH_2)_2$—O—$(CH_2)_2$— | | H | H | O | $CH_3$ | $CH_3$ | |
| H | 4-$NO_2$ | $CH_3$ | $CH_3$ | H | H | O | $CH_3$ | $CH_3$ | |
| H | 4-$CH_3$— | $CH_3$ | $CH_3$ | H | H | O | $CH_3$ | $CH_3$ | |
| H | 4-$CH_3O$ | $CH_3$ | $CH_3$ | H | H | O | $CH_3$ | $CH_3$ | |
| H | 3-Cl | $CH_3$ | $CH_3$ | H | H | O | $CH_3$ | $CH_3$ | |
| H | H | n-$C_6H_{13}$ | $CH_3$ | H | H | O | $CH_3$ | $CH_3$ | |
| H | H | $NCCH_2CH_2$— | $NCCH_2CH_2$— | H | H | O | $CH_3$ | $CH_3$ | |
| H | H | $CH_2CO_2CH_3$ | $CH_2CO_2CH_3$ | H | H | O | $CH_3$ | $CH_3$ | |
| H | 4-NCO | $CH_3$ | $CH_3$ | H | H | O | $CH_3O$ | $CH_3O$ | |
| H | 4-$NHC(O)CH_3$ | $CH_3$ | $CH_3$ | H | H | O | $CH_3O$ | $CH_3O$ | |
| H | 4-$NHC(O)CH(CH_3)_2$ | $CH_3$ | $CH_3$ | H | H | O | $CH_3O$ | $CH_3O$ | |
| H | 4-$NHC(O)NHCH_3$ | $CH_3$ | $CH_3$ | H | H | O | $CH_3O$ | $CH_3O$ | |
| H | 4-$NHC(O)NHCH(CH_3)_2$ | $CH_3$ | $CH_3$ | H | H | O | $CH_3O$ | $CH_3O$ | |
| H | 4-$NHCOCH_3$ | $CH_3$ | $CH_3$ | H | H | O | $CH_3O$ | $CH_3O$ | |
| H | 4-NHCO—i-$C_3H_7$ | $CH_3$ | $CH_3$ | H | H | O | $CH_3O$ | $CH_3O$ | |
| H | 4-$C(O)CH_3$ | $CH_3$ | $CH_3$ | H | H | O | $CH_3O$ | $CH_3O$ | |
| H | 4-$CH_2OCH_3$ | $CH_3$ | $CH_3$ | H | H | O | $CH_3O$ | $CH_3O$ | |
| H | 4-$CH_2SCH_3$ | $CH_3$ | $CH_3$ | H | H | O | $CH_3O$ | $CH_3O$ | |
| H | 4-$CH_2SO_2CH_3$ | $CH_3$ | $CH_3$ | H | H | O | $CH_3O$ | $CH_3O$ | |
| H | H | H | $CH_3$ | H | H | O | $CH_3O$ | $CH_3$ | |
| H | H | H | $C_2H_5$ | H | H | O | $CH_3O$ | $CH_3$ | |
| H | H | H | n-$C_3H_7$ | H | H | O | $CH_3O$ | $CH_3$ | |
| H | H | H | i-$C_3H_7$ | H | H | O | $CH_3O$ | $CH_3$ | |

TABLE IV-continued

Structure: cyclohexane ring with R1' at 5, R1 at 4, SO2NR2R3 at 6/1, SO2N(R4)-C(=W)-N(R5)-pyrimidine(X1,Y1)

| R1' | R1 | R2 | R3 | R4 | R5 | W | X1 | Y1 | m.p.(°C.) |
|---|---|---|---|---|---|---|---|---|---|
| H | H | H | n-C4H9 | H | H | O | CH3O | CH3 | |
| H | H | H | t-C4H9 | H | H | O | CH3O | CH3 | |
| H | H | H | sec-C4H9 | H | H | O | CH3O | CH3 | |
| H | H | H | CH2=CHCH2— | H | H | O | CH3O | CH3 | |
| H | H | H | —CH2CO2CH3 | H | H | O | CH3O | CH3 | |
| H | H | H | —n-C6H13 | H | H | O | CH3O | CH3 | |
| H | H | C6H5-CH2O— | CH3 | H | H | O | CH3O | CH3 | |
| H | H | C6H5-CH(CH3)O— | CH3 | H | H | O | CH3O | CH3 | |
| H | H | (Cl-C6H4)-CH2O— | CH3 | H | H | O | CH3O | CH3 | |
| H | H | (CH3-C6H4)-CH2O— | CH3 | H | H | O | CH3O | CH3 | |
| H | H | CF3CH2— | CF3CH2— | H | H | O | CH3O | CH3 | |
| H | H | CH3— | CF3CHFCF2— | H | H | O | CH3O | CH3 | |
| H | H | CH3— | HBrFCCF2— | H | H | O | CH3O | CH3 | |
| H | H | CH3— | HClFCCF2— | H | H | O | CH3O | CH3 | |
| H | H | CH3— | HCF2CF2— | H | H | O | CH3O | CH3 | |
| H | H | CH3— | HCF2CF2— | H | H | O | CH3O | CH3O | |
| H | H | CH3— | HCF2CF2— | H | H | O | CH3 | CH3 | |
| H | H | —CF2CF2H | CH3 | H | H | O | CH3O | CH3O | |
| H | 4-NHCOCH3 | CH3 | CH3 | H | H | O | CH3O | CH3 | |
| H | 4-NHCO—i-C3H7 | CH3 | CH3 | H | H | O | CH3O | CH3 | |
| H | H | —CH2C≡CH | CH3 | H | H | O | CH3O | CH3 | |
| H | H | —C(CH3)2C≡CH | CH3 | H | H | O | CH3O | CH3 | |
| H | H | —CH2-cyclopropyl | CH3 | H | H | O | CH3O | CH3 | |
| H | H | —CH2-(tetrahydrothiopyranyl) | CH3 | H | H | O | CH3O | CH3 | |

TABLE IV-a

Structure: cyclohexane ring with R1' at 5, R1 at 4, SO2A at 6/1, SO2N(R4)-C(=W)-N(R5)-pyrimidine(X1,Y1)

| A | R1' | R1 | R4 | R5 | W | X1 | Y1 | m.p.(°C.) |
|---|---|---|---|---|---|---|---|---|
| CF3CH2O— | H | H | H | H | O | CH3O | CH3O | |
| CF3CH2O— | H | H | H | H | O | CH3O | CH3 | |
| CF3CH2O— | H | H | H | H | O | CH3 | CH3 | |
| C6H5-O— | H | H | H | H | O | CH3O | CH3O | |
| C6H5-O— | H | H | H | H | O | CH3O | CH3 | |
| C6H5-O— | H | H | H | H | O | CH3 | CH3 | |
| CCl3CH2O— | H | H | H | H | O | CH3O | CH3O | |
| CCl3CH2O— | H | H | H | H | O | CH3O | CH3 | |
| CCl3CH2O— | H | H | H | H | O | CH3 | CH3 | |
| CBr3CH2O— | H | H | H | H | O | CH3O | CH3O | |
| HCF2CH2O— | H | H | H | H | O | CH3O | CH3O | |

TABLE IV-a-continued

| R1' | R1 | R4 | R5 | W | X1 | Y1 |
|---|---|---|---|---|---|---|
| HCF2CF2CH2O— | H | H | H | H | O | CH3O | CH3O |
| CF3CF3CH2O— | H | H | H | H | O | CH3O | CH3O |
| CF3(CF2)2CH2O— | H | H | H | H | O | CH3O | CH3O |
| CF3CH(CH3)O— | H | H | H | H | O | CH3O | CH3O |
| (CF3)2CHO— | H | H | H | H | O | CH3O | CH3 |
| (CF3)2CHO— | H | H | H | H | O | CH3 | CH3 |
| 4-Cl-C6H4-O— | H | H | H | H | O | CH3O | CH3O |
| 4-CH3-C6H4-O— | H | H | H | H | O | CH3O | CH3O |
| 4-CH3O-C6H4-O— | H | H | H | O | O | CH3O | CH3O |
| 4-O2N-C6H4-O— | H | H | H | H | O | CH3O | CH3O |
| CF3CH2O | H | 4-Cl | H | H | O | CH3O | CH3O |
| CF3CH2O | H | 4-CF3 | H | H | O | CH3O | CH3O |
| CF3CH2O | H | 4-CH3O | H | H | O | CH3O | CH3O |
| CF3CH2O | H | 4-NO2 | H | H | O | CH3O | CH3O |
| CF3CH2O | H | 4-CN | H | H | O | CH3O | CH3O |
| CF3CH2O | H | 4-F | H | H | O | CH3O | CH3O |
| CF3CH2O | H | 4-CH3 | H | H | O | CH3O | CH3O |

TABLE V

| R1' | R1 | A | W | νN=C=W (cm⁻¹) |
|---|---|---|---|---|
| H | H | —N(CH3)2 | O | 2220 |
| H | H | —N(C2H5)2 | O | 2210 |
| H | H | —N(CH3)C2H5 | O | |
| H | H | —N(CH3)-i-C3H7 | O | |
| H | H | —N(CH3)-n-C4H9 | O | |
| H | H | —N(CH3)-n-C3H7 | O | |
| H | H | —N(pyrrolidinyl) | O | |
| H | H | —N(CH3)CF2CF2H | O | 2230 |
| H | H | —N(CF2CF2H)2 | O | |
| H | 4-Cl | —N(CH3)2 | O | 2250 |
| H | 4-CF3 | —N(CH3)2 | O | 2220 |
| H | 4-CH3O— | —N(CH3)2 | O | 2230 |
| H | 4-F— | —N(CH3)2 | O | 2250 |
| H | 4-CH3— | —N(CH3)2 | O | 2240 |
| H | 4-NO2— | —N(CH3)2 | O | |
| H | 4-Br— | —N(CH3)2 | O | 2280 |
| H | 4-C2H5O— | —N(CH3)2 | O | 2250 |
| H | 4-CN | —N(CH3)2 | O | |

TABLE V-continued

| $R_1'$ | $R_1$ | A | W | $\nu N=C=W$ (cm$^{-1}$) |
|---|---|---|---|---|
| H | 4-$(CH_3)_2N$ | —$N(CH_3)_2$ | O | |
| H | 4-$SCH_3$ | —$N(CH_3)_2$ | O | |
| H | 4-$SO_2CH_3$ | —$N(CH_3)_2$ | O | |
| H | H | —$N(CH_3)_2$ | S | |
| 5-$CH_3$ | 4-$CH_3$ | —$N(CH_3)_2$ | O | |
| 5-$CH_3O$ | 4-$CH_3O$ | —$N(CH_3)_2$ | O | |
| 5-F | 4-Cl | —$N(CH_3)_2$ | O | |
| 5-Cl | 4-Cl | —$N(CH_3)_2$ | O | |
| H | 3-Cl | —$N(CH_3)_2$ | O | |
| H | 5-Cl | —$N(CH_3)_2$ | O | |
| H | 6-Cl | —$N(CH_3)_2$ | O | |
| H | H | —$N(CH_3)(CH_2CN)$ | O | |
| H | H | —$N(CH_3)(CH_2CO_2CH_3)$ | O | |
| H | H | —$N(CH_3)(CH_2\text{-Ph})$ | O | |
| H | H | —$N(CH_3)(OCH_2\text{-Ph})$ | O | |
| H | H | —$O$-Ph | O | |
| H | H | —$OCH_2CF_3$ | O | |
| H | 4-$CCH_3$ (C=O) | —$N(CH_3)_2$ | O | |
| H | 4-$C$-$i$-$C_3H_7$ (C=O) | —$N(CH_3)_2$ | O | |
| H | 4-$CH_2OCH_3$ | —$N(CH_3)_2$ | O | |
| H | 4-$CH_3O$—$i$-$C_3H_7$ | —$N(CH_3)_2$ | O | |
| H | H | $N(CH_3)(CH_2C\equiv CH)$ | O | |
| H | H | $N(CH_3)(C(CH_3)_2C\equiv CH)$ | O | |
| H | 4-$CH_2SCH_3$ | $N(CH_3)_2$ | O | |
| H | 4-$CH_2SO_2CH_3$ | $N(CH_3)_2$ | O | |
| H | 4-$CH_2S(=O)CH_3$ | $N(CH_3)_2$ | O | |
| H | H | $N(CH_3)$-cyclopropyl | O | |
| H | H | $N(CH_3)(CH_2\text{-thienyl})$ | O | |

Formulations

Useful formulations of the compounds of Formula I can be prepared in conventional ways. They include dusts, granules, pellets, suspensions, emulsions, wettable powders, emulsifiable concentrates and the like. Many of them can be applied directly. Sprayable formulations can be extended in suitable media and used at spray volumes of from a few liters to several hundred liters per hectare. High strength compositions are used primarily as concentrates which are to be diluted prior to ultimate use. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the approximate proportions set forth in Table VI.

TABLE VI

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions (including Emulsifiable Concentrates | 5–50 | 40–95 | 0–15 |
| Aqueous Suspensions | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active Ingredient plus at least one of a Surfactant or a Diluent equals 100 weight percent.

Lower or higher levels of active ingredient can be present, depending on the intended use and the physical properties of the compound. Higher ratios of surfactant to active ingredient are sometimes desirable, and are achieved by incorporation into the formulation, or by tank mixing.

Some typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide", 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending, and usually grinding, as in a hammer or fluid energy mill. Suspensions are prepared by wet milling (see, for example, Littler, U.S. Pat. No. 3,060,084). Granules and pellets can be made by spraying the active material on preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Col. 6, line 16 through Col. 7, line 19 and Examples 10 through 41.

R. W. Luckenbaugh, U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182.

H. Gysin and E. Knusli, U.S. Pat. No. 2,891,855, Col. 3, line 66 through Col. 5, line 17 and Examples 1–4.

G. C. Klingman, "Weed Control as a Science", John Wiley & Sons, Inc., New York, 1961, pp. 81–96.

J. D. Fryer and S. A. Evans, "Weed Control Handbook", 5th Ed., Blackwell Scientific Publications, Oxford, 1968, pp. 101–103.

Unless indicated otherwise, all parts are by weight in the following examples.

EXAMPLE 41

| Wettable Powder | |
|---|---|
| N'-[(4,6-Dimethoxypyrimidin-2-yl)aminocarbonyl]-N,N-dimethyl-1,2-benzenedisulfonamide | 90% |
| dioctyl sodium sulfosuccinate | 0.1% |
| sodium ligninsulfonate | 1% |
| synthetic fine silica | 8.9% |

The ingredients are blended and ground in a hammer mill to produce particles almost all of which ~99% are below 100 microns in size. The product is sifted through a U.S.S. No. 50 screen and packaged.

EXAMPLE 42

| Granule | |
|---|---|
| wettable powder of Example 41 | 10% |
| attapulgite granules (U.S.S. #20–40; 0.84–0.42 mm) | 90% |

A slurry of wettable powder containing 50% solids is sprayed on the surface of attapulgite granules in a double-cone blender. The granules are dried and packaged.

EXAMPLE 43

| Wettable Powder | |
|---|---|
| N'-[(4,6-Dimethoxy-1,3,5-triazin-2-yl)aminocarbonyl]-N,N-dimethyl-1,2-benzenedisulfonamide | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

EXAMPLE 44

| Granule | |
|---|---|
| wettable powder of Example 43 | 25% |
| gypsum | 64% |
| potassium sulfate | 11% |

The ingredients are blended in a rotating mixer and water sprayed onto the tumbling mixture to accomplish granulation. When most of the material has reached the desired range of 1.0 to 0.42 mm (U.S.S. #18–40 sieves), the granules are removed, dried, and screened. Oversize material is crushed to produce additional material in the desired range. These granules contain 10% active ingredient.

EXAMPLE 45

| Wettable Powder | |
|---|---|
| N'-[(4-Methoxy-6-methylpyrimidin-2-yl)aminocarbonyl]-N,N-dimethyl-1,2-benzenedisulfonamide | 80% |
| sodium alkylnaphthalenesulfonate | 2% |
| sodium ligninsulfonate | 2% |
| synthetic amorphous silica | 3% |

-continued

| Wettable Powder | |
|---|---|
| kaolinite | 13% |

The ingredients are blended and coarsely ground in a hammer mill to produce particles essentially all below 100 microns in size. The material is then reblended, sifted through a U.S.S. No. 50 sieve (0.3 mm opening) and packaged.

EXAMPLE 46

| Wettable Powder | |
|---|---|
| N'-[(4,6-Dimethoxypyrimidin-2-yl)aminocarbonyl]-N,N-dimethyl-1,2-benzenedisulfonamide | 65% |
| dodecylphenol polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying onto the solid ingredients in the blender. After grinding in a hammer mill to produce particles essentially all below 100 microns, the material is reblended, sifted through a U.S.S. No. 50 sieve (0.3 mm opening) and packaged.

EXAMPLE 47

| Wettable Powder | |
|---|---|
| N'-[(4,6-Dimethoxy-1,3,5-triazin-2-yl)aminocarbonyl]-N,N-dimethyl-1,2-benzenedisulfonamide | 50% |
| sodium alkylnaphthalenesulfonate | 2% |
| low viscosity methyl cellulose | 2% |
| diatomaceous earth | 46% |

The ingredients are blended, coarsely hammer milled and then air milled to produce particles of active essentially all below 10 microns in diameter. The product is reblended before packaging.

EXAMPLE 48

| Oil Suspension | |
|---|---|
| N'-[(4-Methoxy-6-methylpyrimidin-2-yl)aminocarbonyl]-N,N-dimethyl-1,2-benzenedisulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting suspension may be applied directly, but preferably after being extended with oils or emulsified in water.

EXAMPLE 49

| Aqueous Suspension | |
|---|---|
| N'-[(4,6-Dimethoxypyrmindin-2-yl)aminocarbonyl]-N,N-dimethyl-1,2-benzenedisulfonamide | 25% |
| hydrated attapulgite | 3% |
| crude calcium ligninsulfonate | 10% |
| sodium dihydrogen phosphate | 0.5% |
| water | 61.5% |

The ingredients are ground together in a ball or roller mill until the solid particles have been reduced to diameters under 10 microns, and then packaged.

EXAMPLE 50

| Extruded Pellet | |
|---|---|
| N'-[(4,6-Dimethoxy-1,3,5-triazin-2-yl)aminocarbonyl]-N,N-dimethyl-1,2-benzenedisulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer milled and then moistened with about 12% water. The mixture is extruded as cyclinders about 3 mm diameter which are cut to product pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 51

| Solution | |
|---|---|
| N'-[(4-Methoxy-6-methylpyrimidin-2-yl)aminocarbonyl]-N,N-dimethyl-1,2-benzenedisulfonamide | 5% |
| dimethylformamide | 95% |

The ingredients are combined and stirred to produce a solution, which can be used for low volume applications.

Utility

The compounds of the present invention are highly active herbicides. They have utility for broad spectrum pre- and/or post-emergence weed control in areas where complete control of all vegetation is desired, such as around fuel storage tanks, ammunition depots, industrial storage areas, oil well sites, drive-in theaters, around billboards, highway and railroad structures. Alternatively, some of the subject compounds are useful for the selective pre- or post-emergence weed control in crops, such as corn, wheat and rice. By properly selecting rate and time of application, compounds of this invention may be used also to modify plant growth beneficially.

The precise amount of the compound of Formula I to be used in any given situation will vary according to the particular end result desired, including their use as selective or general herbicides, the crop species involved, the amount of foliage present, the species of weeds to be controlled, the soil type, the formulation and mode of application, weather conditions, etc. Since so many variables play a role, it is not possible to state a rate of application suitable for all situations. Broadly speaking, the compounds of this invention are used at levels of about 0.001 to 10 kg/ha with a preferred range of 0.03 to 5 kg/ha. In general, the higher rates of application from within this range will be selected for adverse conditions, where extended persistence in soil is desired, or for nonselective weed control purposes.

The compounds of Formula I may be combined with other herbicides and are particularly useful in combination with substituted urea herbicides such as 3-(3,4- dichlorophenyl)-1,1-dimethyl urea; the triazines such as 2-chloro-4-(ethylamino)-6-(isopropylamino)-s-triazine: the uracils such as 5-bromo-3-sec-butyl-6-methyluracil; N-(phosponomethyl)glycine; 3-cyclohexyl-1-methyl-6-dimethylamino-s-triazine-2,4(1H,3H)-dione; N,N-dimethyl-2,2-diphenylacetamide; 2,4-dichlorophenoxyacetic acid (and closely related compounds; 4-chloro-2-butynyl-3-chlorophenylcarbamate; diisopropylthiolcarbamic acid; ester with 2,3-dichloroallyl alcohol; diisopropylthiolcarbamic acid, S-(2,3,3-trichloroallyl)ester; ethyl-N-benzoyl-N-(3,4-dichlorophenyl)-2-aminopropionate; 1,2-dimethyl-3,5-diphenylpyrazolium methylsulfate; methyl 2-[4-(2,4-dichlorophenoxy)-phenoxy]propanoate; 4-amino-6-tert-butyl-3-(methylthio)-1,2,4-triazin-5(4H)-one; 3-(3,4-dichlorophenyl)-1-methoxy-1-methylurea; 3-isopropyl-1H-2,1,3-benzothiodiazin-(4)-3H-one-2,2-dioxide; $\alpha,\alpha,\alpha$-trifluoro-2,6-dinitro-N,N-dipropyl-p-toluidine; 1,1'-dimethyl-4,4'-bipyridinium ion; monosodium methanearsonate; 2-chloro-2',6'-diethyl(methoxymethyl)acetanilide; and 1,1-dimethyl-3-($\alpha,\alpha,\alpha$-trifluoro-m-tolyl)-urea.

The activity of these compounds was discovered in greenhouse tests. The tests are described and the data resulting from them are shown below.

Test Procedure A

Seeds of crabgrass (Digitaria spp.), barnyardgrass (*Echinochloa crusgalli*), wild oats (*Avena fatua*), cassia (*Cassia tora*), morningglory (Ipomoea spp.), cocklebur (Xanthium spp.), sorghum, corn, soybean, rice, wheat and nutsedge tubers (*Cyperus rotundus*) were planted in a growth medium and treated pre-emergence with a nonphytotoxic solvent solution of the compounds. At the same time, cotton having five leaves (including cotyledonary ones), bush beans with the third trifoliate leaf expanding, crabgrass with two leaves, barnyardgrass with two leaves, wild oats with two leaves, cassia with three leaves (including cotyledonary ones), morningglory with four leaves (including the cotyledonary ones), cocklebur with four leaves (including cotyledonary ones), sorghum with four leaves, corn with four leaves, soybean with two cotyledonary leaves, rice with three leaves, wheat with one leaf, and nutsedge with three-five leaves were sprayed with a nonphytotoxic solvent solution of the compounds. Other containers of the above mentioned weeds and crops were treated pre- or post-emergence with the same nonphytotoxic solvent so as to provide a solvent control. A set of untreated control plants was also included for comparison. Pre-emergence and post-emergence treated plants and controls were maintained in a greenhouse for sixteen days, then all treated plants were compared with their respective controls and rated visually for response to treatment using the following rating system and symbols:

TABLE A

| Structure | Rate kg/ha | Bush-bean | Cotton | Morning-glory | Cockle-bur | Cassia | Nut-sedge | Crab-grass | Barn-yard grass | Wild Oats | Wheat | Corn | Soy-bean | Rice | Sor-ghum |
|---|---|---|---|---|---|---|---|---|---|---|---|---|---|---|---|
| CH₃O-pyrimidine-C(O)-NH-C(O)-NH-SO₂-C₆H₄-SO₂-N(CH₃)₂ (structure 1) | 0.4 | 9C | 9C | 10C | 9C | 8C | 8G | 5C,9G | 9C | 9C | 9C | 9C | 9C | 5C,9G | 9C |
| (structure 2, triazine variant) | 0.4 | 9C | 9C | 10C | 4C,9G | 9C | 2C,9G | 5C,9G | 9C | 8C | 4C,7G | 9C | 5C,8G | 5C,9G | 9C |
| (structure 3, methyl pyrimidine) | 0.4 | 3C,9G,6Y | 9C | 10C | 5C,9G | 5C,9G | 8G | 4C,9G | 4C,9G | 4C,7G | 3C,6G | 6U,9G | 5C,9G | 5C,9G | 3U,9G |
| (structure 4, OCH₃/CH₃ triazine sulfonyl) | 0.1 | 9D,9G | 9C | 10C | 10C | 9C | 8G | 9C | 9C | 9C | 4C,8G | 10C | 9C | 9C | 9C |
| (structure 5, CH₃/CH₃ triazine sulfonyl) | 0.1 | 9D,9G | 9C | 10C | 9C | 5C,9G | 6C,9G | 9C | 10C | 9C | 5C,9G | 9C | 9C | 9C | 10C |

POST-EMERGENCE

TABLE A-continued

| Structure | 0.1 | | | | | | | | | | | | | | | | |
|---|---|---|---|---|---|---|---|---|---|---|---|---|---|---|---|---|---|
| Structure with CH₃, N, CH₃ triazine; SO₂NH-C(=O)-NH; SO₂N(CH₃)₂ | 0.1 | 9C | 9C | 9C | 10C | 9C | 9C | 7G | 9C | 9C | 10C | 10C | 10C | 9C | 9C | 10C | |
| Structure with OCH₃, N, OCH₃ triazine; SO₂NH-C(=O)-NH; SO₂N(C₂H₅)₂ | 0.1 | 5C,9G | 2U,4C,9G | 9C | 9C | 9C | 2C,8G | 6G | 9C | 1C,5G | 0 | 9C | 3C,9G | 2C,7G | 2C,8G | |
| Structure with OCH₃, CH, OCH₃ triazine; SO₂NH-C(=O)-NH; SO₂N(C₂H₅)₂ | 0.1 | 4G,8G,6Y | 4C,8G | 9C | 2C,9G | 5C,9G | 2C,9G | 9C | 5C,9H | 3C,8G | 5U,9G | 5C,9G | 5C,9G | | |
| Structure with OCH₃, N, OCH₃ triazine; SO₂NH-C(=O)-NH; SO₂N(C₂H₅)₂ | 0.1 | 4C,9G,6Y | 5C,9G | 5C,9G | 5C,9G | 10C | 1C,8G | 5G | 5C,9H | 1C,6G | 2C,4G | 2C,9H | 2C,9G | 5C,9G | | |
| Structure with OCH₃, CH, OCH₃ triazine; SO₂NH-C(=O)-NH; SO₂N(C₂H₅)₂ | 0.1 | 2C,8G,6Y | 3C,6G | 5C,9G | 5C,9G | 4C,6G | 6G | 2G | 2G,9H | 2C,9H | 2C,5G | 6H | 2C,9H | 5C,9G | | |
| Structure with CH₃, N, CH₃ triazine; SO₂NH-C(=O)-NH; SO₂N(C₂H₅)₂ | 0.1 | 5C,7G,6Y | 3C,4H | 9C | 3C,7G | 0 | 2C,9G | 10C | 2C,9G | 5C,8G | 10C | 10C | 3C,9G | 5C,9G | 4C,9G | |
| Structure with OCH₃, N, CH₃ triazine; SO₂NH-C(=O)-NH; SO₂N(C₂H₅)₂ | 0.1 | | | | | | | | | | | | 3C,9G | 6C,9G | 6C,9G | |

TABLE A-continued

| Structure | | | | | | | | | | | | | | | | |
|---|---|---|---|---|---|---|---|---|---|---|---|---|---|---|---|---|
| Structure 1 (SO₂NH-C(=O)-NH-pyrimidine-(CH₃)₂, with SO₂N(C₂H₅)₂) | 0.1 | 3C,5G,6Y | 4C,6H | 5C,9G | 5C,9G | 4C | 1C,3G | 4G | 2C,9H | 2C,6G | 3C | 9C | 2C,8H | 5C,9G | 9C |
| Structure 2 (CF₃-phenyl, SO₂NH-C(=O)-NH-pyrimidine-(OCH₃)₂, SO₂N(CH₃)₂) | 0.1 | 9C | 1U,3C,9G | 9C | 9C | 8C | 2C,9G | 0 | 1C,5H | 2C,4G | 2C,3G | 2H,6G | 2C,9G | 2C,6G | 2U,9G |
| Structure 3 (Cl-phenyl, SO₂NH-C(=O)-NH-pyrimidine-(OCH₃)(CH₃), SO₂N(CH₃)₂) | 0.1 | 9D,9G,6Y | 5C,9G | 3C,9G | 3C,9G | 5C,9G | 5C,9G | 2C,5G | 3C,9H | 1C,6G | 2C,7G | 2C,9H | 3C,9H | 4C,8G | 2U,9G |
| Structure 4 (phenyl, SO₂NH-C(=O)-NH-pyrimidine-(OCH₃)₂, SO₂OCH₂CF₃) | 0.1 | 9D,9G,6Y | 9C | 10C | 4C,9G | 5C,9G | 2C,9G | 3C | 6C,9H | 0 | 0 | 2G | 9C | 6G | 2H,9G |
| Structure 5 (phenyl, SO₂NH-C(=O)-NH-pyrimidine-(OCH₃)(CH₃), SO₂OCH₂CF₃) | 0.1 | 9D,9G,6Y | 2H,5C,9G | 10C | 9C | 3C,8H | 5G | 2C,5G | 2C,5H | 0 | 0 | 2U,9G | 3C,9G | 1C,5G | 2C,9G |
| Structure 6 (phenyl, SO₂NH-C(=O)-NH-pyrimidine-(CH₃)(OCH₃), SO₂OCH₂CF₃) | 0.1 | 4C,9G,6Y | 6C,9G | 10C | 5C,9G | 2C,5H | 2C,8G | 2G | 2C,9H | 0 | 0 | 9H | 3C,9G | 1C,2G | 1C,9H |

TABLE A-continued
| | | | | | | | | | | | | | | |
|---|---|---|---|---|---|---|---|---|---|---|---|---|---|---|
| structure | 0.1 | 9D,9G,6Y | 6C,9G | 9C | 9C | 5C,9G | 2C,6H | 4G | 3G | 4C,9H | 0 | 2U,9G | 3C,9G | 7G | 5C,9G |
| structure | 0.1 | 9D,9G,6Y | 9C | 10C | 5C,9G | 6C,9G | 9G | 5C,9G | 4C,9H | 2C,9G | 2C,9G | 9C | 6C,9G | 3C,9G |
| structure | 0.1 | 9C | 9C | 9C | 5C,9G | 9G | 9G | 6C,9G | 2C,9G | 3C,9G | 2C,9G | 9C | 6C,9G | 1C,9G |
| structure | 0.1 | 7C,9G,6Y | 6C,9G | 10C | 5C,9G | 9C | 9G | 4C,9G | 5C,9G | 2C,9G | 2C,9G | 5C,9G | 5C,9G | 2C,9G |
| | PRE-EMERGENCE | | | | | | | | | |
|---|---|---|---|---|---|---|---|---|---|---|
| | Morning-glory | Cockle-bur | Cas-sia | Nut-sedge | Crab-grass | Barn-yard-grass | Wild Oats | Wheat | Corn | Soy-bean | Rice | Sor-ghum |
| | 9G | 8G | 9G | 10E | 2C,9G | 10H | 2G,6G | 9H | 9G | 9H | 10E | 10H |

TABLE A-continued

| Structure | | | | | | | | | | | | | |
|---|---|---|---|---|---|---|---|---|---|---|---|---|---|
| CH₃O—pyrimidine(OCH₃)—C(O)—NH—SO₂—phenyl—(CH₃)₂N—SO₂ | 9G | 8G | 9G | 10E | 5C,9G | 5C,9H | 3C,7G | 9H | 10E | 9H | 10E | 10E |
| CH₃O—pyrimidine(CH₃)—C(O)—NH—SO₂—phenyl—(CH₃)₂N—SO₂ | 9G | 9G | 9G | 10E | 5C,9G | 3C,9H | 4C,8G | 9H | 9G | 9H | 10E | 10E |
| (OCH₃/CH₃ pyrimidine)—C(O)—NH—SO₂NHCH₃, SO₂N(CH₃)₂ phenyl | 3C,9H | 9H | 2C,9G | 10E | 2C,9H | 2C,9G | 2C,9G | 9H | 1C,9G | 9H | 10E | 10H |
| (CH₃/CH₃ pyrimidine)—C(O)—NH—SO₂NHCH₃, SO₂N(CH₃)₂ phenyl | 9G | 9H | 3C,9G | 10E | 4C,9H | 5C,9H | 3C,9G | 9H | 9G | 9H | 10E | 10H |
| (CH₃/OCH₃ pyrimidine)—C(O)—NH—SO₂NHCH₃, SO₂N(CH₃)₂ phenyl | 1C,9G | 9H | 2C,9G | 1C,8G | 9H | 1C,9H | 3C,9H | 9H | 9H | 9H | 10E | 10H |
| (OCH₃/OCH₃ pyrimidine)—C(O)—NH—SO₂NHC₂H₅, SO₂N(C₂H₅) phenyl | 8G | 9H | 2C,8G | 8G | 9H | 9H | 1C,9G | 9G | 9G | 6H | 10E | 9G |

TABLE A-continued

| Structure | | | | | | | | | | | |
|---|---|---|---|---|---|---|---|---|---|---|---|
| Ph-SO2NH-C(=O)-NH-triazine(OCH3,OCH3), ortho SO2N(C2H5)2 | 5C,9G | 9H | 5C,8G | 7G | 1C,7G | 9H | 8G | 8G | 9G | 2C,4H | 10E | 2C,9H |
| Ph-SO2NH-C(=O)-NH-triazine(OCH3,CH3), ortho SO2N(C2H5)2 | 9G | 9H | 4C,9G | 9G | 1C,9G | 1C,9H | 1C,8G | 8G | 1C,9G | 2C,8H | 10E | 9H |
| Ph-SO2NH-C(=O)-NH-triazine(CH3,CH3), ortho SO2N(C2H5)2 | 3C,9G | 9H | 2C,6G | 2G | 5G | 9H | 7G | 5G | 9H | 1C,4G | 9H | 9H |
| Ph-SO2NH-C(=O)-NH-triazine(OCH3,CH3), ortho SO2N(C2H5)2 | 5C,9G | 9H | 5C,7G | 7G | 8G | 2C,9H | 8G | 8G | 9G | 2C,3G | 10E | 9H |
| Ph-SO2NH-C(=O)-NH-triazine(OCH3,CH3), ortho SO2N(C2H5)2 | 2C,9G | 9H | 5C,6G | 1C,9G | 2C,8G | 1C,9H | 2C,7G | 8G | 9G | 1C,1H | 10E | 9H |
| 4-CF3, 2-SO2N(CH3)2-Ph-SO2NH-C(=O)-NH-pyrimidine(OCH3,OCH3) | 9G | 9H | 2G | 10E | 2C,8H | | 1C,7G | | 1C,8G | 9H | — | 1C,9H |

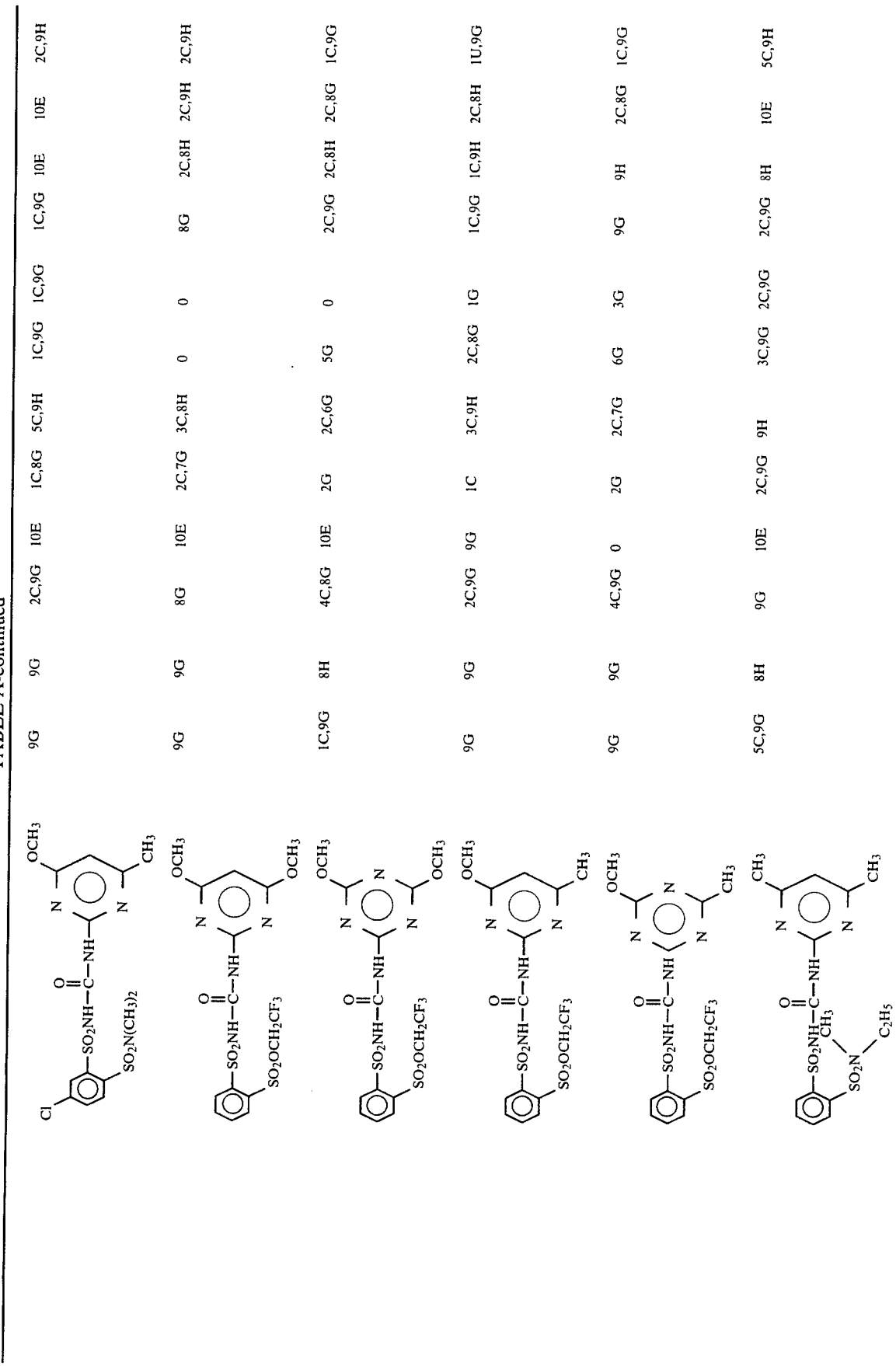

TABLE A-continued

| Structure | | | | | | | | | | | |
|---|---|---|---|---|---|---|---|---|---|---|---|
| ![structure 1: phenyl-SO2NH-C(=O)-NH-pyrimidine(OCH3,CH3) with SO2N(CH3)(C2H5)] | 9G | 9H | 9G | 10E | 4C,9G | 9H | 4C,9G | 2C,9G | 1C,9G | 10E | 6C,9H |
| ![structure 2: phenyl-SO2NH-C(=O)-NH-pyrimidine(OCH3,OCH3) with SO2N(CH3)(C2H5)] | 9G | 9H | 9G | 10E | 4C,9G | 9H | 2C,8G | 1C,7G | 9G | 8H | 9H |

0 = no effect
10 = maximum effect
C = chlorosis or necrosis
D = defoliation
E = emergence inhibition
G = growth retardation
H = formative effects
U = unusual pigmentation
6Y = abscised buds or flowers

Test Procedure B

Two plastic bulb pans were filled with fertilized and limed Fallsington silt loam soil. One pan was planted with corn, sorghum, Kentucky bluegrass and several grassy weeds. The other pan was planted with cotton, soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pennsylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugarbeets. The above four containers were treated pre-emergence with several test compounds within the scope of the invention.

Twenty-eight days after treatment, the plants were evaluated and visually rated for response to the chemical treatments utilizing the rating system described previously for Test A. The data are summarized in Test B.

Test B

|  | Compound 1 | | Compound 2 | |
|---|---|---|---|---|
| Rate kg/ha | 0.06 | 0.25 | 0.06 | 0.25 |
| Crabgrass | 9C,9G | 10C | 9C,9G | 9C,9G |
| Barnyardgrass | 10C | 10C | 10C | 10C |
| Sorghum | 10E | 10E | 10E | 10C |
| Wild Oats | 4C,6G | 9C,6G | 3C,5G | 8C,6G |
| Johnsongrass | 9C,9G | 10C | 9C,9G | 9C,9G |
| Dallisgrass | 3C,8G | 6C,9G | 4G | 6G |
| Giant Foxtail | 10C | 10C | 9C,9G | 10C |
| Ky. bluegrass | 10C | 10C | 10C | 10C |
| Cheatgrass | 10C | 10C | 6C,8G | 10C |
| Sugarbeets | 8E,8G | 10C | 10C | 10C |
| Corn | 9C,8G | 10C | 10C | 10E |
| Mustard | 10C | 10C | 10C | 9C,9G |
| Cocklebur | 7G | 7G | 8G | 8G |
| Pigweed | 10E | 10E | 10E | 10E |
| Nutsedge | 8E,8G | 10E | 6G | 8G |
| Cotton | 8G | 8C,9G | 8G | 8G |
| Morningglory | 8G | 6C,8G | 8C,8G | 10C |
| Cassia | 7C,8G | 9C,9G | 5C,8G | 7C,9G |
| Teaweed | 10C | 10C | 8C,7G | 6C,7G |
| Velvetleaf | 10C | 10C | 10C | 10C |
| Jimsonweed | 3C,8G | 2C,8G | 3C,8G | 5C,8G |
| Soybean | 7H,7G | 8C,8G | 8C,8G | 8C,8G |
| Rice | 10C | 10E | 10E | 10E |
| Wheat | 4C,7G | 10E | 6G | 5C,6G |

| Rate kg/ha | 0.008 | 0.03 | 0.06 | 0.25 |
|---|---|---|---|---|
| Crabgrass | 3H,7G | 7C,9G | 10C | 10C |
| Barnyardgrass | 10C | 10C | 10C | 10C |
| Sorghum | 10C | 10C | 10E | 10E |
| Wild Oats | 5C,7G | 8C,7G | 8C,6G | 9C,7G |
| Johnsongrass | 8C,9G | 9C,9G | 9C,9G | 10C |
| Dallisgrass | 6G | 5H,9G | 7C,9G | 10C |
| Giant Foxtail | 9C,9G | 10C | 10C | 10C |
| Ky. bluegrass | 10C | 10C | 10C | 10C |
| Cheatgrass | 10C | 10C | 10E | 10E |
| Sugarbeets | 7C,8G | 10C | 8C,9G | 10C |
| Corn | 6C,8G | 10C | 10C | 10C |
| Mustard | 10C | 10C | 10C | 10C |
| Cocklebur | 5H,7G | 7H,8G | 8G | 3C,8G |
| Pigweed | — | — | 10E | 10E |
| Nutsedge | 9G | 10E | 8E,9G | 10E |
| Cotton | 8G | 8G | 3H,7G | 8C,9G |
| Morningglory | 4C,8G | 10C | 5C,8G | 10C |
| Cassia | 5C,6G | 5C,8G | 6C,8G | 7C,8G |
| Teaweed | 5C,7G | 10C | 9C,8G | 9C,8G |

-continued

| Test B | | | | |
|---|---|---|---|---|
| Velvetleaf | 3G | 10C | 9C,8G | 10C |
| Jimsonweed | 3C,7G | 7C,8G | 6C,8G | 8C,8G |
| Soybean | — | — | 3C,8G | 8C,8G |
| Rice | 10E | 10E | 10E | 10E |
| Wheat | 6C,8G | 10C | 8C,8G | 10C |

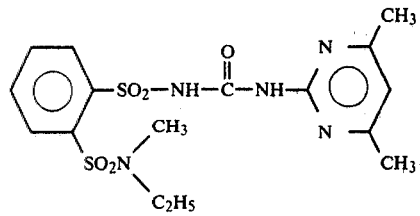

| Rate kg/ha | 0.03 | 0.12 |
|---|---|---|
| Crabgrass | 4G | 7G |
| Barnyardgrass | 7G,3C | 8G,6C |
| Sorghum | 10C | 10C |
| Wild Oats | 5G,3C | 6G,4C |
| Johnsongrass | 8G,3H | 8G,5C |
| Giant foxtail | 6G,3C | 10C |
| Ky. bluegrass | 7G,3C | 8G,6C |
| Cheatgrass | 8G,8C | 9G,9C |
| Sugarbeets | 6G,4C | 8G,6C |
| Corn | 6G,5H | 8G,5U |
| Mustard | 8G,9C | 9G,9C |
| Cocklebur | 6G,5H | 7G,5H |
| Nutsedge | 8G | 9G |
| Cotton | 8G | 8G |
| Morningglory | 8G | 8G,4C |
| Cassia | 5G | 8G,7C |
| Teaweed | 3C | 8C |
| Velvetleaf | 5G,5C | 7G,7C |
| Jimsonweed | 5G,6C | 8G,9C |
| Soybean | 0 | 2G,1C |
| Rice | 10E | 10E |
| Wheat | 5G,3C | 7G,5C |

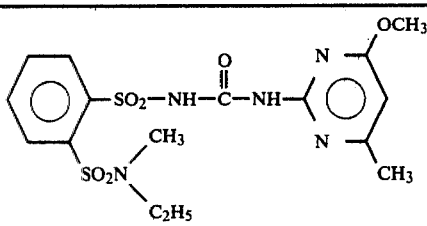

| Rate kg/ha | 0.03 | 0.12 |
|---|---|---|
| Crabgrass | 7G,2C | 8G,4C |
| Barnyardgrass | 7G,5C | 8G,7C |
| Sorghum | 10C | 10C |
| Wild Oats | 5G,3C | 6G,3C |
| Johnsongrass | 7G,5H | 8G,5C |
| Giant foxtail | 8G,3C | 9G,8C |
| Ky. bluegrass | 7G | 7G,4C |
| Cheatgrass | 7G,7C | 10E |
| Sugarbeets | 7G,5C | 7G,5C |
| Corn | 6G,5H | 7G,3H |
| Mustard | 9G,9C | 10C |
| Cocklebur | 8G,5H | 8G,5H |
| Nutsedge | 7G | 5G |
| Cotton | 5G | 5G |
| Morningglory | 8G,3C | 8G,4C |
| Cassia | 4G | 8G,7C |
| Teaweed | 3C | 3C |
| Velvetleaf | 4G,5C | 7G,7C |
| Jimsonweed | 6G,6C | 8G,8C |
| Soybean | 1C | 5G,4C |
| Rice | 7G,7C | 10E |
| Wheat | 5G,2C | 6G,4C |

Test B

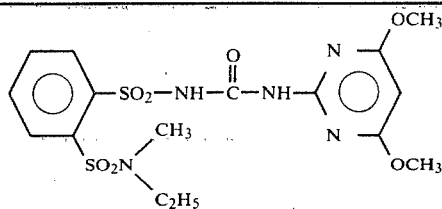

| Rate kg/ha | 0.03 | 0.12 |
|---|---|---|
| Crabgrass | 6G,2C | 8G,3C |
| Barnyardgrass | 7G,2C | 8G,5C |
| Sorghum | 10C | 10E |
| Wild Oats | 5G,3C | 5G,3C |
| Johnsongrass | 8G,3H | 8G,5H |
| Giant foxtail | 6G,3C | 10C |
| Ky. bluegrass | 7G | 8G,5C |
| Cheatgrass | 7G,3C | 8G,8C |
| Sugarbeets | 6G,4C | 8G,6C |
| Corn | 5G,3H | 7G,5H |
| Mustard | 9G,9C | 10C |
| Cocklebur | 5G | 7G |
| Nutsedge | 9G | 9G |
| Cotton | 5G | 8G |
| Morningglory | 7G,5C | 8G,5C |
| Cassia | 6G | 8G,8C |
| Teaweed | 0 | 4C |
| Velvetleaf | 4G,3H | 7G,6C |
| Jimsonweed | 6G,5C | 5G,5C |
| Soybean | 0 | 2G |
| Rice | 10E | 10E |
| Wheat | 4G,2C | 5G,3C |

Test Procedure C

Twenty-five cm diameter plastic pots filled with Fallsington silt loam were planted to soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pennsylvanicum*), crabgrass (*Digitaria spp.*), nutsedge (*Cyperus rotundus*), barnyardgrass (*Echinochloa crusgalli*), giant foxtail (*Setaria faberii*) and wild oats (*Avena fatua*). Approximately 2½ weeks after planting, the young plants and the soil around them were sprayed overall with the test chemicals dissolved in a nonphytotoxic solvent. Fourteen days after treatment, all species were compared to untreated controls and visually rated for response to treatment. The rating system was as described previously for test A. The data are presented in Test C. It is obvious that some of the compounds have utility for selective weed control in crops such as wheat and rice.

Test C

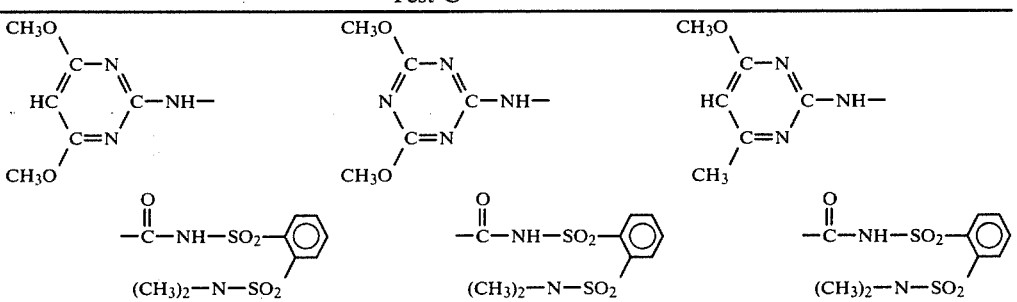

| Rate kg/ha | 0.06 | 0.25 | 0.06 | 0.25 | 0.06 | 0.25 |
|---|---|---|---|---|---|---|
| Soybeans | 9C,10G | 9C,10G | 9C,10G | 9C,10G | 9C,10G | 9C,10G |
| Velvetleaf | 10C | 10C | 10C | 10C | 10C | 10C |
| Sesbania | 10C | 10C | 10C | 10C | 10C | 10C |
| Cassia | 8C,10G | 10C | 8C,10G | 9C,10G | 8C,10G | 8C,10G |
| Cotton | 9C,10G | 10C | 10C | 10C | 9C,10G | 9C,10G |
| Morningglory | 10C | 10C | 10C | 10C | 10C | — |
| Alfalfa | 10C | 10C | 10C | 10C | 10C | 10C |
| Jimsonweed | 10C | 10C | 7C,10G | 10C | 9C,10G | 10C |
| Cocklebur | 10C | 10C | 9C,10G | 9C,10G | 10C | 10C |
| Corn | 10C | 10C | 10C | 10C | 10C | 10C |
| Crabgrass | 4C,10G | 10C | 5C,10G | 10C | 6C,10G | 4C,8G |
| Rice | 8C,10G | 7C,10G | 7C,10G | 8C,10G | 5C,10G | 4C,10G |
| Nutsedge | 7C,10G | 7C,10G | 5G | 2C,8G | 4G | 4G |
| Barnyardgrass | 9C,10G | 8C,10G | 8C,10G | 9C,10G | 8C,10G | 9C,10G |
| Wheat | 8C,10G | 6C,10G | 6C,10G | 6C,10G | 6C,10G | 6C,10G |

Test C-continued

| | | | | | | | |
|---|---|---|---|---|---|---|---|
| Giant Foxtail | 9C,10G | 10C | 9C,10G | 10C | 2C | 7C,10G | |
| Wild Oats | 9C,10G | 8C,10G | 8C,10G | 9C,10G | 9C,10G | 9C,10G | |
| Sorghum | 9C,10G | 10C | 10C | 9C,10G | 8C,10G | 9C,10G | |

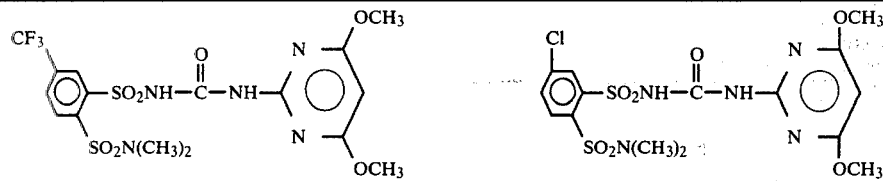

| Rate kg/ha | 0.25 | 0.12 | 0.06 | 0.03 | 0.015 | 0.007 | 0.003 | 0.25 | 0.06 | 0.015 |
|---|---|---|---|---|---|---|---|---|---|---|
| Soybeans | 10G,8C | 10C | 10G,6C | 10C | 10C | 10G,7C | 6G,7C | 10G,7C | 10G,4C | 10G,3C |
| Velvetleaf | 10C | 10C | 10C | 10C | 10C | 10C | 10C | 9C | 9C | 8G,4C |
| Sesbania | 10G,9C | 10C | 10C | 10C | 10C | — | — | 9C | 10C | 8C |
| Cassia | 10G,9C | 10C | 10C | 10C | 10G,9C | 10G,7C | 9G,4C | 10G,6C | 10G,7C | 10G,5C |
| Cotton | 10C | 10G,7C | 10G,9C | 10G,5C | 9G,3C | 10C | 9G,5C | 10G,8C | 10G,7C | 10G,7C |
| Morningglory | 10G,8C | 10C | 10C | 10C | 10G,9C | 9G,3C | 9G,4C | 10G,8C | 10G,8C | 10G,7C |
| Alfalfa | — | 10C | 10G,7C | 9C | 8C | 8C | 9C | 8C | 8C | 8C |
| Jimsonweed | — | — | 10G,7C | — | — | 7G,3C | 7G,2C | — | — | — |
| Cocklebur | 10G,9C | 10G,9C | 10G,9C | 10G,9C | 10G,7C | 8G,6C | — | 9C | 10G,6C | 9G,4C |
| Corn | 2G,1C | 1C | 0 | 0 | 0 | 0 | 0 | 4G,1C | 1G | 0 |
| Crabgrass | 9G | 0 | 2G | 0 | — | 5G,1C | 0 | 4G | 5G | 4G |
| Rice | 6G,1C | 4G | — | 2G | 0 | 1C | 0 | 8G,2C | 8G,2C | 6G,1C |
| Nutsedge | 8G,1C | 9G | 5G | 9G | 7G | 6G | 7G | 7G | 7G | 5G,1C |
| Barnyardgrass | — | 8G,2C | 4G | 5G | 3G | 2G | 2G | 7G,2C | 5G | 5G |
| Wheat | 7G,1C | 5G | 0 | 2G | 1G | 0 | 0 | 9G,1C | 8G | 7G |
| Giant Foxtail | 2G | — | 0 | — | — | — | — | — | — | — |
| Wild Oats | 1G | 5G,1C | 0 | 0 | 0 | 1G | 2G | 8G,2C | 3G | 2G |
| Sorghum | 7G,2C | 8G,3C | 9G,2C | 4G,1C | 4G | 2G,1C | 2G,1C | 8G,2C | 9G,3C | 7G,2C |

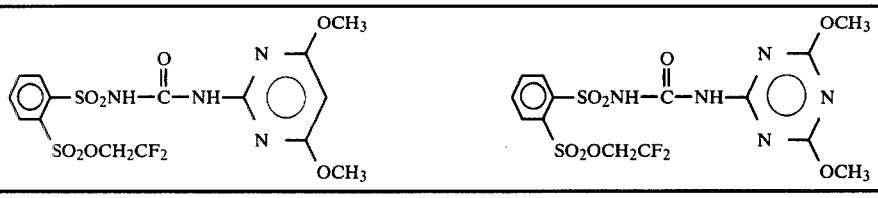

| Rate kg/ha | 0.12 | 0.06 | 0.03 | 0.015 | 0.12 | 0.06 | 0.03 | 0.015 |
|---|---|---|---|---|---|---|---|---|
| Soybeans | 10G,8C | 10G,6C | 8G,6C | 8G,5C | 9G,6C | 10G,7C | 8G,4H | 8G,5C |
| Velvetleaf | — | 9G,6C | — | 3G,2C | — | 9G,6H | — | 6G,3C |
| Sesbania | — | 10G,7C | — | 7G,3C | — | 8G,4C | — | 5G,3C |
| Cassia | 10C | 10G,5C | 10G,6C | 7G,3C | 9G,5C | 8G,3C | 9G,5C | 7G,3C |
| Cotton | 8G,3C | 9G,6C | — | 1C | 10G,4C | 8G,3C | 9G,3C | 4G,3C |
| Morningglory | — | 10G,9C | — | 7G,3C | — | 10G,8C | 8G,3C | 9G,6C |
| Alfalfa | 9G,6C | 9G,3C | 9G,6C | 5G,2C | 9G,6C | 3G | 8G,4C | 0 |
| Jimsonweed | 0 | 3G | — | 0 | — | 5G | — | 0 |
| Cocklebur | 9G,3C | 10G,6C | 10G,7C | 9G,2C | 10G,8C | 10G,6C | 10G,8C | 10G,4C |
| Corn | 0 | 2G | 1G | 0 | 7G,2C | 9G,3C | 6G,1C | 9G,4H |
| Crabgrass | 4G,3C | 1C | 4C | 1G | 10G,5C | 8G | 10G,3C | 7G |
| Rice | 7G,2C | 3G,1C | — | 0 | 0 | 6G,1C | — | 2G |
| Nutsedge | 9G | 9G | 8G,1C | 5G | 6G | 3G | 6G | 0 |
| Barnyardgrass | 9G,2C | 7G,2C | 8G,2C | 1G | 6G | 7G | 5G | 5G |
| Wheat | 0 | 0 | 0 | 0 | 0 | 0 | 0 | 0 |
| Giant Foxtail | — | — | — | — | — | — | — | — |
| Wild Oats | 2G | 0 | 1G | 0 | 1G | 3G | 0 | 1G |
| Sorghum | 6G,2C | 7G,2C | 6G,2C | 2G | 8G,3C | 9G,3C | 9G,3C | 4G,1C |

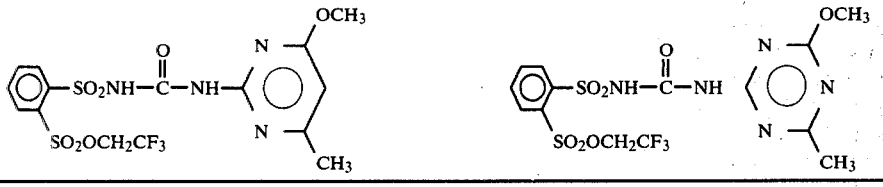

| Rate kg/ha | 0.12 | 0.06 | 0.03 | 0.015 | 0.12 | 0.06 | 0.03 | 0.015 |
|---|---|---|---|---|---|---|---|---|
| Soybeans | 9G,4C | 9G,5C | 8G,5C | 8G,4C | 10G,3H | 10G,7C | 9G,3H | 8G,5C |
| Velvetleaf | — | 9G,5C | — | 4G,3C | — | 9G,5C | — | 8G,3C |
| Sesbania | — | 7G,3C | — | 3G,2C | — | 9G,4C | — | 7G,3C |
| Cassia | 9G,3C | 8G,3C | — | 6G,2C | 10G,8C | 7G,3C | 10G,7C | 7G,3C |
| Cotton | 10C | 8G,3C | 9G,5C | 6G,3C | 9G,6C | 8G,3C | 7G,3C | 6G,3C |
| Morningglory | 9G,3C | 10G,7C | 9G,3C | 10G,4C | 9G,3C | 10G,8C | — | 10G,7C |
| Alfalfa | 10G,7C | 9G,3C | 10G,7C | 7G,2C | 10G,7C | 9G,3C | 10G,5C | 7G,2C |
| Jimsonweed | — | 6G | — | 2G | — | 7G,1C | — | 5G |
| Cocklebur | 10G,8C | 9G,4C | 9G,6C | 9G,6H | 10G,8C | 10G,7C | 8G,6C | 9G,4C |
| Corn | 3G | 5G | 1G | 2G | 8G,2C | 8G,2C | 8G,2C | 7G,2C |
| Crabgrass | 9G,4C | 7G,1C | 5G,3C | 5G,2C | 10G,4C | 3G,1C | 10G,4C | 1G,1C |

Test C-continued

| | | | | | | | | |
|---|---|---|---|---|---|---|---|---|
| Rice | 4G,1C | 5G,1C | 4G,1C | 4G,1C | 2G,1C | 4G,2C | 0 | 3G,1C |
| Nutsedge | 7G,3C | 9G,2C | 5G,3C | 7G,1C | 4G | 0 | 2G | 0 |
| Barnyardgrass | 9G,2C | 8G | 8G,1C | 7G | — | 2G,1C | 6G | 1G |
| Wheat | 1G | 0 | 1G | 0 | 0 | 0 | 0 | 0 |
| Giant Foxtail | — | — | — | — | — | — | — | — |
| Wild Oats | 1G | 7G,1C | 1G | 5G | 5G,3C | 2G | 5G,3C | 0 |
| Sorghum | 9G,2C | 10G,3C | 9G,2C | 9G,3C | 9G,2C | 9G,2C | 10G,2C | 8G,2C |

Test Procedure D

Purple nutsedge (*Cyperus rotundus*) tubers were planted about 2 cm deep in Fallsington silt loam soil contained in 10 cm diameter plastic pots. Five tubers were planted in each pot. Compounds of this invention were dissolved in an non-phytotoxic diluent and sprayed at 560 l/ha in four methods of application: soil surface, tuber/soil, soil incorporated, and post-emergence. The soil surface spray consisted of spraying the compound on the surface of the firmed covering soil. The tuber/soil spray consisted of spraying the compound on exposed tubers and subtending soil before adding the untreated covering soil. Soil incorporated treatment consisted in mixing the compound with the covering soil before using it to cover the tubers. The post-emergence treatment was sprayed on nutsedge foliage and the surrounding soil surface when nutsedge had emerged and grown to a height of about 12 cm. Pots receiving the post-emergence treatments were placed directly in the greenhouse. Pots receiving the other treatments were misted with about 0.3 cm water before being transferred to the greenhouse. Response ratings assessed after four weeks are recorded in Test D, based on the same rating system as described in procedure A.

TEST D

Nutsedge Control

| Compound | Rate kg/ha | Pre-Emergence Soil Surface | Tuber Spray | Soil Incorp. | Post-Emergence |
|---|---|---|---|---|---|
| Compound 1 (CH3O/CH3O pyrimidine) | 0.008 | 8G | 5C,8G | 5E,8G | 5C,6G |
|  | 0.03 | 9E,9G | 10E | 10E | 8C,10G |
|  | 0.12 | 10E | 10E | 10E | 10C |
| Compound 2 (CH3O/CH3O triazine) | 0.008 | 7G | 7G | 7G | 2G |
|  | 0.03 | 2C,7G | 2C,7G | 2C,7G | 3C,5G |
|  | 0.12 | 8G | 2C,8G | 2C,8G | 3C,3G |
| Compound 3 (CH3O/CH3 pyrimidine) | 0.008 | 2C,6G | 8G | 5E,8G | 4G |
|  | 0.03 | 9G | 5E,9G | 9E,9G | 3C,5G |
|  | 0.12 | 10E | 10E | 10E | 9C |

Test Procedure E

Twenty-five cm diameter plastic pots filled with Fallsington silt loam were planted with corn (*Zea mays*), nutsedge (*Cyperus rotundus*), barnyardgrass (*Echinochloa crusgalli*), johnsongrass (*Sorghum halepense*), sorghum (*Sorghum vulgare*), crabgrass (*Digitaria sanguinalis*), cassia (*Cassia tora*), cocklebur (*Xanthium pennsylvanicum*), morningglory (*Ipomoea hederacea*), field bindweed (*Convolvulus arvensis*), jimsonweed (*Datura stramonium*) and velvetleaf (*Abutilon theophrasti*). Approximately 2½ weeks after planting, the young plants and the soil around them were sprayed overall with the test chemicals dissolved in a non-phytotoxic solvent. Fourteen days after treatment, all species were compared to untreated controls and visually rated for response to treatment. The rating system was as described previously for Test A. The data are presented in Test E. It is obvious that these compounds have utility for selective weed control in corn.

TEST E
OVER-THE-TOP SOIL/FOLIAGE TREATMENTS

| Compound | Rate kg/ha | Corn | Nut- sedge | Barn- yard- grass | John- son- grass | Sor- ghum | Crab- grass | Cassia | Cockle- bur | Morning- glory | Field Bind- weed | Jimson- weed | Vel- vet- leaf |
|---|---|---|---|---|---|---|---|---|---|---|---|---|---|
| CF₃-C₆H₃(SO₂N(CH₃)₂)-SO₂-NH-C(O)-NH-[pyrimidine(OCH₃)₂] | 0.03 | 0 | | | 6G | 7G,3C | 3G | 10G,9C | 10C | 10C | 10C | 10G,6C | 10C |
| | 0.06 | 0 | 9G | 4G,4C | 6G | 7G,3C | 0 | 10C | 10G,9C | 10C | 10C | 10C | 10C |
| | 0.12 | 0 | 9G | 4G | 7G | 9G,2C | 7G | 10C | 10C | 10C | 10C | 10C | 10C |
| | 0.25 | 1G | 8G | 5G,4C | | | | 10C | 10C | 10C | 10C | 10C | 10C |
| C₆H₄(SO₂OCH₂CF₃)-SO₂-NH-C(O)-NH-[pyrimidine(OCH₃)₂] | 0.03 | 0 | 6G | 0 | 0 | 0 | 0 | 9G,8C | 10C | 10C | 9G,3C | 0 | 10C |
| | 0.06 | 0 | 9G | 2G | 4G | 3G | — | 8G,6C | 9G,5C | 10C | — | 3G | 10C |
| | 0.12 | 0 | 8G | 2G | 4G | 3G | 0 | 10G,7C | 9G,5H | 10C | 9G,2C | 0 | 10C |
| C₆H₄(SO₂N(C₂H₅)₂)-SO₂-NH-C(O)-NH-[pyrimidine(CH(CH₃))₂] | 0.015 | 0 | | 0 | 5G,2C | 8G,1C | 0 | 9G,3C | 8G,4C | 10C | 9G,3C | 3G | 10C |
| | 0.03 | 0 | 5G | 0 | 8G,1C | 9G,1C | 0 | 9G,5C | 10C | 10C | 10G,5C | 4G | 10C |
| | 0.06 | | | | | | | 10G,7C | 8G,2C | 10C | 10G,6C | 7G | 10C |
| | 0.12 | | | | | | | 10G,9C | 10C | 10C | 10C | 8G | 10C |

What is claimed is:
1. A compound of the formulae

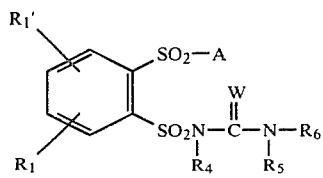

wherein
A is $NR_2R_3$, $OCH_2CCl_3$, $OCH_2CBr_3$ or

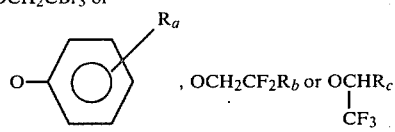, $OCH_2CF_2R_b$ or $OCHR_c$ where $R_a$ is H, Cl, $CH_3$, $OCH_3$ or $NO_2$ and $R_b$ is H, F or $C_1$-$C_2$ alkyl with 0-5F and $R_c$ is $CH_3$ or $CF_3$;
$R_1$ is H, Cl, Br, F, $C_1$-$C_3$ alkyl, $NO_2$, $OCH_3$,
$\overset{O}{\underset{\|}{C}}$-$R_d$, $CH_2OR_d$, $CF_3$, $NH_2$, N=C=O, NH-$\overset{O}{\underset{\|}{C}}$-$R_d$,
NH-$\overset{O}{\underset{\|}{C}}$-$NHR_d$ or NH-$\overset{O}{\underset{\|}{C}}$-$OR_d$ where $R_d$ is $C_1$-$C_3$ alkyl, or $R_1$ is $N(CH_3)_2$, CN, $CH_2S(O)_nCH_3$ or $S(O)_nCH_3$, where n is 0, 1 or 2;
$R_1'$ is H, Cl, F, Br, $CH_3$ or $OCH_3$;
$R_2$ is H, $C_1$-$C_6$ alkyl, $C_3$-$C_4$ alkenyl, $C_3$-$C_6$ cycloalkyl, $C_4$-$C_7$ cycloalkylalkyl, $C_5$-$C_6$ cycloalkenyl, $C_3$-$C_5$ alkynyl, $C_3$-$C_6$ cycloalkyl substituted with 1-2 $CH_3$ groups, $CF_2CF_2H$, $CF_2CHFCl$, $CF_2CHFBr$, $CF_2CHFCF_3$, $C(CH_3)_2CN$, $(CH_2)_mCN$, where m is 1 or 2, $CH_2CH_2OCH_3$, $CH_2CH(CH_3)OCH_3$, $(CH_2)_3OCH_3$, $CHR_7CO_2R_8$ or $CHR_7CON(R_8)_2$, where $R_7$ is H or $CH_3$ and $R_8$ is $C_1$-$C_3$ alkyl, $OCH_3$,

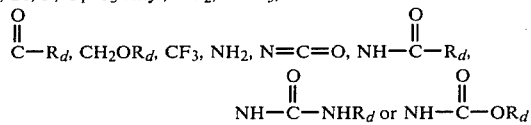

where
$R_9$ is H, $CH_3$, Cl, Br or F;
$R_3$ is $C_1$-$C_4$ alkyl, $C_3$-$C_4$ alkenyl, $CH_2CH_2OCH_3$, $CH_2CH(CH)_3OCH_3$, $CH_2CF_3$, or $(CH_2)_mCN$, where m is 1 or 2, or $CHR_7CO_2R_8$,
$NR_2R_3$ taken together are

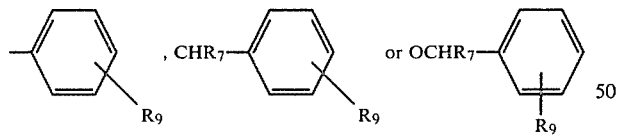

$R_4$ and $R_5$ are independently H or $CH_3$, but $R_4$ and $R_5$ cannot both be $CH_3$;
$R_6$ is

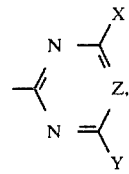

wherein
X is H, $CH_3$, $CH_3O$ or $CH_3CH_2O$;
Y is Cl, Br, H, $C_1$-$C_3$ alkyl, $CF_3$, $NHCH_3$ $N(CH_3)_2$, $OCH_2CF_3$, $OCH_3$, $OC_2H_5$, $SCH_3$, $O(CH_2)_pOR_{10}$, where p is 2 or 3 and $R_{10}$ is $CH_3$ or $C_2H_5$, $CH_2CH_2OCH_3$, $CH_2OCH_3$, $CH_2OCH_2CH_3$, $OCHR_7CO_2R_{11}$, $OCHR_7CON(R_8)_2$, $CO_2R_{11}$ and $CH_2CO_2R_{11}$, where $R_{11}$ is H or $C_1$-$C_3$ alkyl, $CH_2CN$, $NCH_3(CH_2CN)$, $CH_2CH_2CN$, $CH_2Cl$, $N_3$, $OCH_2CH=CH_2$ or $OCH_2C\equiv CH$;
provided that:
(1) when $R_2$ is $OCH_3$, $R_3$ is $CH_3$;
(2) when $R_2$ is $CF_2CHFCl$, $CF_2CHFBr$, $CF_2CF_2H$ or $CF_2CHFCF_3$, then $R_3$ is $C_1$-$C_4$ alkyl;
and their agriculturally suitable salts.
2. The compounds of claim 1 wherein $R_4=R_5=H$.
3. The compounds of claim 2 wherein W=O.
4. The compounds of claim 3 wherein $R_1'=H$.
5. The compounds of claim 3 wherein A is $OCH_2CF_3$ or $NR_2R_3$ and $R_2$ is $C_1$-$C_6$ alkyl, $C_3$-$C_4$ alkenyl, $OCH_3$, $CH_2CH_2OCH_3$, $CH_2CH(CH_3)OCH_3$ or $(CH_2)_3OCH_3$, or $NR_2R_3$ taken together are

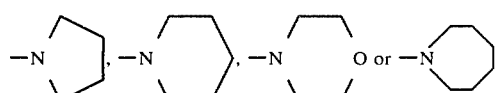

6. The compounds of claim 3 wherein $R_3$ is $C_1$-$C_4$ alkyl or where $NR_2R_3$ taken together are

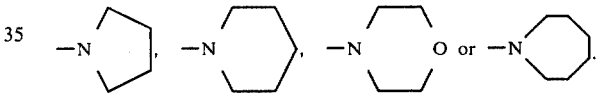

7. The compounds of claim 5 wherein $R_3$ is $C_1$-$C_4$ alkyl or where $NR_2R_3$ taken together are

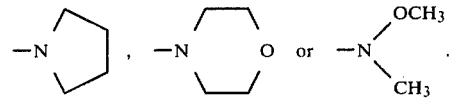

8. The compounds of claim 7 wherein $R_1$ is H, Cl, $CF_3$, $NO_2$, $CH_3$ or $OCH_3$.
9. The compounds of claim 8 wherein $R_2$ is $C_1$-$C_4$ alkyl or $NR_2R_3$ taken together are

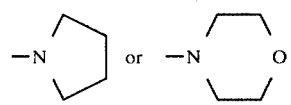

10. The compounds of claim 9 in which
X is $CH_3$, $OCH_3$ or $OCH_2CH_3$; and

Y is H, CH$_3$, CH$_3$CH$_2$, OCH$_2$CF$_3$, OCH$_3$, OC$_2$H$_5$, OCH$_2$CH$_2$OCH$_3$, CH$_2$OCH$_3$, CH$_2$CH$_2$OCH$_3$, N(CH$_3$)CH$_2$CN, OCH$_2$CH=CH$_2$, or OCH$_2$C≡CH.

11. The compounds of claim 10 in which
X is CH$_3$, OCH$_3$ or OCH$_2$CH$_3$; and
Y is CH$_3$, OCH$_2$CF$_3$, OCH$_3$ or OCH$_2$CH$_3$.

12. The compound of claim 1, N'-[(4,6-Dimethoxypyrimidin-2-yl)aminocarbonyl]-N,N-dimethyl-1,2-benzenedisulfonamide.

13. The compound of claim 1, N'-[(4-Methoxy-6-methylpyrimidin-2-yl)aminocarbonyl]-N,N-dimethyl-1,2-benzenedisulfonamide.

14. The compound of claim 1, N'-[(4,6-Dimethylpyrimidin-2-yl)aminocarbonyl]-N,N-dimethyl-1,2-benzenedisulfonamide.

15. The compound of claim 1, N'-[(4-Methoxy-6-methylpyrimidin-2-yl)aminocarbonyl]-N,N-diethyl-1,2-benzenedisulfonamide.

16. The compound of claim 1, N'-[(4,6-Dimethoxypyrimidin-2-yl)aminocarbonyl]-N,N-diethyl-1,2-benzenedisulfonamide.

17. The compound of claim 1, N'-[(4,6-Dimethylpyrimidin-2-yl)aminocarbonyl]-N,N-diethyl-1,2-benzenedisulfonamide.

18. The compound of claim 1, N$^2$[(4,6-Dimethoxypyrimidin-2-yl)aminocarbonyl]-N$^1$,N$^1$-dimethyl-4-(trifluoromethyl)-1,2-benzenesulfonamide.

19. The compound of claim 1, 4-Chloro-N$^2$-[(4-methoxy-6-methylpyrimidin-2-yl)aminocarbonyl]-N$^1$,N$^1$-dimethyl-1,2-benzenedisulfonamide.

20. The compound of claim 1, (2,2,2-Trifluoroethyl) 2-[[(4,6-dimethoxypyrimidin-2-yl)aminocarbonyl]aminosulfonyl]benzenesulfonoate.

21. The compound of claim 1, (2,2,2-Trifluoroethyl) 2-[[(4-methoxy-6-methylpyrimidin-2-yl)aminocarbonyl]aminosulfonyl]benzenesulfonoate.

22. The compound of claim 1, N'[(4,6-Dimethylpyrimidin-2-yl)aminocarbonyl]-N-ethyl-N-methyl-1,2-benzenedisulfonamide.

23. The compound of claim 1, N-Ethyl-N'-[(4-methoxy-6-methylpyrimidin-2-yl)aminocarbonyl]-N-methyl-1,2-benzenedisulfonamide.

24. The compound of claim 1, N'-[(4,6-Dimethoxypyrimidin-2-yl)aminocarbonyl]-N-ethyl-N-methyl-1,2-benzenedisulfonamide.

25. The compound of claim 1, N-Methyl-N(1-methylethyl)-N'-[(4,6-dimethoxypyrimidin-2-yl)aminocarbonyl]-1,2-benzenedisulfonamide.

26. The compound of claim 1, N-Methyl-N(1-methylethyl)-N'-[(4-methyl-6-methoxypyrimidin-2-yl)aminocarbonyl]-1,2-benzenedisulfonamide.

27. A composition for the control of undesirable vegetation consisting essentially of a compound of claim 1 and at least one of (a) a surface-active agent and (b) a solid or liquid diluent.

28. A composition for the control of undesirable vegetation consisting essentially of a compound of claim 2 and at least one of (a) a surface-active agent and (b) a solid or liquid diluent.

29. A composition for the control of undesirable vegetation consisting essentially of a compound of claim 3 and at least one of (a) a surface-active agent and (b) a solid or liquid diluent.

30. A composition for the control of undesirable vegetation consisting essentially of a compound of claim 4 and at least one of (a) a surface-active agent and (b) a solid or liquid diluent.

31. A method for the control of undesirable vegetation comprising applying to the locus of such undesirable vegetation a herbicidally effective amount of a compound of claim 1.

32. A method for the control of undesirable vegetation comprising applying to the locus of such undesirable vegetation a herbicidally effective amount of a compound of claim 2.

33. A method for the control of undesirable vegetation comprising applying to the locus of such undesirable vegetation a herbicidally effective amount of a compound of claim 3.

34. A method for the control of undesirable vegetation comprising applying to the locus of such undesirable vegetation a herbicidally effective amount of a compound of claim 4.

* * * * *

UNITED STATES PATENT OFFICE
CERTIFICATE OF CORRECTION

PATENT NO. : 4,310,346
DATED : January 12, 1982
INVENTOR(S) : George Levitt and Richard F. Sauers It is certified that error appears in the above-identified patent and that said Letters Patent are hereby corrected as shown below:

Column 116, after line 19, insert -- Z is CH; and W is O or S; --.

Signed and Sealed this

Eleventh Day of January 1983

[SEAL]

Attest:

GERALD J. MOSSINGHOFF

Attesting Officer  Commissioner of Patents and Trademarks